United States Patent
Peterson et al.

(10) Patent No.: US 11,859,257 B2
(45) Date of Patent: Jan. 2, 2024

(54) **COMPOSITIONS AND METHODS FOR DETECTING *STAPHYLOCOCCUS AUREUS***

(71) Applicant: Gen-Probe Incorporated, San Diego, CA (US)

(72) Inventors: Patrick Peterson, San Marcos, CA (US); Paul Darby, San Diego, CA (US); Matthias Jost, San Diego, CA (US); Siobhan Miick, San Diego, CA (US); Matthew Brentnall, Escondido, CA (US); JoAnn Jackson, Lakeside, CA (US)

(73) Assignee: Gen-Probe Incorporated, San Diego, CA (US)

( * ) Notice: Subject to any disclaimer, the term of this patent is extended or adjusted under 35 U.S.C. 154(b) by 17 days.

(21) Appl. No.: 16/637,237

(22) PCT Filed: Aug. 9, 2018

(86) PCT No.: PCT/US2018/045975
§ 371 (c)(1),
(2) Date: Feb. 6, 2020

(87) PCT Pub. No.: WO2019/032809
PCT Pub. Date: Feb. 14, 2019

(65) Prior Publication Data
US 2020/0392565 A1   Dec. 17, 2020

Related U.S. Application Data

(60) Provisional application No. 62/544,491, filed on Aug. 11, 2017.

(51) Int. Cl.
*C12Q 1/68* (2018.01)
*C12Q 1/689* (2018.01)

(52) U.S. Cl.
CPC ......... *C12Q 1/689* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 6,156,507 A | 12/2000 | Hiramatsu et al. | |
| 9,777,335 B2 | 10/2017 | Huletsky et al. | |
| 2008/0015349 A1* | 1/2008 | Skrzypczynski | C07H 21/04 536/25.3 |
| 2008/0160524 A1* | 7/2008 | Ma | C12N 9/1252 435/5 |
| 2008/0227087 A1* | 9/2008 | Huletsky | C12Q 1/689 435/6.15 |
| 2013/0266942 A1 | 10/2013 | Menard et al. | |

FOREIGN PATENT DOCUMENTS

| | | | |
|---|---|---|---|
| WO | WO 2002/099034 A2 | 12/2002 | |
| WO | WO 2007/044873 A2 | 4/2007 | |
| WO | WO-2008140612 A2 * | 11/2008 | ............. C12Q 1/689 |

OTHER PUBLICATIONS

Huletsky et al. Journal of Clinical Microbiology, May 2004, p. 1875-1884 (Year: 2004).*
NEB Catalog (1996/1997), p. 111 (Year: 1997).*
Rothstein et al. (1994) PNAS USA 91: 4155-4159 (Year: 1994).*
Becker et al. (J Clin Microbiol 54:180-184) (Year: 2016).*
Garcia et al. (Lancet Infect Dis 2011; 11: 595-603, plus 16 pages of webappendix) (Year: 2011).*
GenBank NG_047938.1 obtained from https://www.ncbi.nlm.nih.gov/nuccore/NG_047938.1 on Jan. 29, 2022, 2 pages. (Year: 2016).*
HF569166.1 obtained from https://www.ncbi.nlm.nih.gov/nuccore/hf569116.1 on Jan. 29, 2022, 15 pages. (Year: 2014).*
Alignment of GenBank NG_047938.1 and HF569166.1. Obtained from https://blast.ncbi.nlm.nih.gov/Blast.cgi#alnHdr_452754752 on Jan. 13, 2022. 3 pages. (Year: 2022).*
Becker et al. "Detection of mecA- and mecC-Positive Methicillin-Resistant *Staphylococcus aureus* (MRSA) Isolates by the New Xpert MRSA Gen 3 PCR Assay," Journal of Clinical Microbiology, 54(1): 2016.
Becker et al. "Methicillin resistance in *Staphylococcus* isolates: The "mec alphabet" with specific consideration of mecC, a mec homolog associated with zoonotics *S. aureus* lineages," International Journal of Medical Microbiology, 304: 794-801 (2014).
Bitrus et al. "In vitro transfer of methicillin resistance determinants mecA from methicillin resistant *Staphylococcus aureus* (MRSA) to methicillin susceptible *Staphylococcus aureus* (Mssa)," BMC Microbiology, 17; (2017).
Database Accession No. AB781447, "*Staphylococus aureus* subsp. Aureus 3989 DNA, SCCmec type V staphylococcal cassette chromosome mec region," 8 pages, Apr. 14, 2014.
Database Accession No. KX529089, "*Staphylococus aureus* strain UPM01 Orfx (orfx) gene, partial cds," 1 page, Jul. 28, 2016.
Huletsky et al. "New Real-Time PCR Assay for Rapid Detection of Methicillin-Resistant *Staphylococcus aureus* Directly from Specimens Containing a Mixture of Staphylococci," Journal of Clinical Microbiology, 42(5): 1875-1884 (2004).

(Continued)

Primary Examiner — Juliet C Switzer
(74) Attorney, Agent, or Firm — Adam M. Breier; Michael J. Gilly

(57) ABSTRACT

Provided herein are compositions, kits, and methods for detecting methicillin-resistant *Staphylococcus aureus* (MRSA) nucleic acids. In some embodiments, the compositions, kits, and methods can be used to detect one or more of type i, ii, iii, iv, v, vi, vii, viii, ix, xii, xiii, xiv, xv, or xxi SCCmec right extremity junction (MREJ) MRSA nucleic acids and one or more of mecA, mecC, and/or an additional *S. aureus*-specific gene.

16 Claims, 5 Drawing Sheets

Specification includes a Sequence Listing.

(56) References Cited

OTHER PUBLICATIONS

International Search Report and Written Opinion, PCT Application No. PCT/US2018/045975, dated Jan. 4, 2019, 30 pages.

Preliminary Report on Patentability, PCT Application No. PCT/US2018/045975, dated Feb. 20, 2020, 15 pages.

Shambat et al. "Clonal complexes and virulence factor of *Staphylococcus aureus* from several cities in India," *BMC Microbiology*, 12: 64 (2012).

Shore et al. "Detection of Staphylococcal Cassette Chromosome mec Type XI Carrying Highly Divergent mecA, mecI, mecR1, blaZ, and ccr Genes in Human Clinical Isolates of Clonal Complex 130 Methicillin-Resistant *Staphylococcus aureus*," *Antimicrobial Agents and Chemotherapy*, 55(8); 3765- 3773 (2011).

Van Der Zee et al. "Detection of novel chromosome-SCCmec variants in Methicillin Resistant *Staphylococcus aureus* and their inclusion in PCR based screening," *BMC Research Notes*, 4: 150, 6 pages (2011).

* cited by examiner

| | This Disclosure | | | | | | Cepheid Xpert SA Nasal Complete | | | | | |
|---|---|---|---|---|---|---|---|---|---|---|---|---|
| Isolate ID | CFU/mL Tested | orfX/SCCmec | mecA/C | GAPDH | MRSA Call | SA Call | CFU/mL Tested | SCC | mec | SPA | MRSA Call | SA Call |
| Bengal Bay Clone | 1,000 | 31.5 | 32.2 | 30.6 | Positive | Positive | 10,000 | 38.2 | 28.2 | 28.8 | Negative | Positive |
| Bengal Bay Clone (PVL neg) | 1,000 | 32.1 | 32.5 | 31.2 | Positive | Positive | 10,000 | 37.4 | 27.7 | 28.1 | Positive | Positive |
| WA MRSA-5 variant | 1,000 | 32.1 | 33.1 | 31.4 | Positive | Positive | 10,000 | 0.0 | 28.3 | 28.5 | Negative | Positive |
| WA MRSA-99 | 1,000 | 32.5 | 33.0 | 31.2 | Positive | Positive | 10,000 | 0.0 | 28.7 | 29.5 | Negative | Positive |
| WA MRSA-117 | 1,000 | 32.8 | 33.6 | 31.7 | Positive | Positive | 10,000 | 0.0 | 27.8 | 28.2 | Negative | Positive |
| WA MRSA-136 | 1,000 | 44.7 | 33.4 | 31.8 | Positive | Positive | 10,000 | 36.9 | 27.4 | 27.8 | Positive | Positive |
| WA MRSA-137 (PVL neg) | 1,000 | 32.3 | 33.1 | 31.4 | Positive | Positive | 10,000 | 35.2 | 26.4 | 26.6 | Positive | Positive |
| WA MRSA-138 | 1,000 | 32.2 | 33.1 | 31.3 | Positive | Positive | 10,000 | 37.8 | 27.1 | 27.4 | Positive | Positive |
| M2885 | 1,000 | 32.0 | 32.9 | 31.4 | Positive | Positive | 10,000 | 0.0 | 26.8 | 26.2 | Negative | Positive |
| M4374 | 1,000 | 32.8 | 33.7 | 32.0 | Positive | Positive | 10,000 | 0.0 | 28.3 | 28.3 | Negative | Positive |
| BL74 | 1000 approx. | 34.7 | 36.3 | 34.3 | Positive | Positive | >10,000,000 approx | 39.4 | 20.8 | 20.5 | Negative | Positive |

Fig. 2

| In-house ID | MREJ | SCCmec Type | CFU/mL* | orfX/SCCmec Positivity | mecA/C Positivity | GAPDH Positivity | IC Positivity | MRSA Positivity | SA Positivity |
|---|---|---|---|---|---|---|---|---|---|
| GP1822 | ii | II | 63 | 61% | 81% | 72% | 100% | 44% | 72% |
| | | | 209 | 97% | 100% | 86% | 100% | 83% | 86% |
| | | | 626 | 100% | 100% | 100% | 100% | 100% | 100% |
| | | | 2087 | 100% | 100% | 100% | 100% | 100% | 100% |
| | | | 6261 | 100% | 100% | 100% | 100% | 100% | 100% |
| GP1826 | xii | V | 20 | 8% | 17% | 6% | 100% | 3% | 6% |
| | | | 67 | 36% | 50% | 39% | 100% | 19% | 39% |
| | | | 202 | 69% | 89% | 78% | 100% | 67% | 78% |
| | | | 673 | 97% | 100% | 100% | 100% | 97% | 100% |
| | | | 2019 | 100% | 100% | 100% | 100% | 100% | 100% |
| CI5708 | xv | V | 10 | 67% | 71% | 83% | 100% | 58% | 83% |
| | | | 30 | 100% | 100% | 100% | 100% | 100% | 100% |
| | | | 100 | 100% | 100% | 100% | 100% | 100% | 100% |
| | | | 300 | 100% | 100% | 100% | 100% | 100% | 100% |
| | | | 1000 | 100% | 100% | 100% | 100% | 100% | 100% |
| GP1827 | xxi | XI | 16 | 19% | 22% | 17% | 100% | 0% | 17% |
| | | | 54 | 69% | 64% | 64% | 100% | 39% | 64% |
| | | | 161 | 86% | 92% | 97% | 100% | 81% | 97% |
| | | | 537 | 100% | 100% | 100% | 100% | 100% | 100% |
| | | | 1611 | 100% | 100% | 100% | 100% | 100% | 100% |

* CFU/mL concentration confirmed by colony count for GP1822, GP1826, and GP1827

Fig. 3

| Condition | Positivity Results | | | | | |
|---|---|---|---|---|---|---|
| | MRSA | SA | OrfX/SCCmec | mecA/C | GAPDH | IC |
| Negative Control | 0% | 0% | 0% | 0% | 0% | 100% |
| Positive Control: (MRSA) at $10^3$ CFU/mL | 100% | 100% | 100% | 100% | 100% | 100% |
| Panel 1: GP1821 S. capitis, GP1994 S. caprae, GP0742 S. epidermidis (MSSE) each at $10^6$ CFU/mL | 0% | 0% | 0% | 0% | 0% | 100% |
| Panel 2: S. epidermidis (MRSE), S. delphini, S. haemolyticus each at 106 CFU/mL | 0% | 0% | 0% | 100% | 0% | 100% |
| Panel 3: S. hominis, S.intermedius, S. lutrae each at $10^6$ CFU/mL | 0% | 0% | 0% | 0% | 0% | 100% |
| Panel 4: S. pseudointermedius, S. saprophyticus, S. schleiferi each at $10^6$ CFU/mL | 0% | 0% | 0% | 0% | 0% | 100% |
| Panel 5: S. simulans, S. warneri, S. xylosus each at $10^6$ CFU/mL | 0% | 0% | 0% | 0% | 0% | 100% |
| Panel 6: S. warneri, S. epidermidis (MRSE), S. schleiferi each at $10^6$ CFU/mL | 0% | 0% | 0% | 100% | 0% | 100% |
| Panel 7: S. pasteuri at $10^6$ CFU/mL | 0% | 0% | 0% | 0% | 0% | 100% |

Fig. 5

SEQUENCE LISTING

<160> NUMBER OF SEQ ID NOS: 126

<210> SEQ ID NO 1
<211> LENGTH: 709
<212> TYPE: DNA
<213> ORGANISM: Staphylococcus aureus

<400> SEQUENCE: 1

```
tacattagaa atacaaggaa agatgctatc ttccgaagga ttggcccaag aattgaacca     60
acgcatgacc caagggcaaa gcgactttgt tttcgtcatt ggcggatcaa acggcctgca    120
caaggacgtc ttacaacgca gtaactacgc actatcattc agcaaaatga cattcccaca    180
tcaaatgatg cgggttgtgt taattgaaca agtgtacaga gcatttaaga ttatgcgagg    240
agaagcttat cataagtaat gaggttcatg atttttgaca tagttagcct ccgcagtctt    300
tcatttcaag taaataatag cgaaatattc tttatactga atacttatag tgaagcaaag    360
ttctagcttt gagaaaattc tttctgcaac taaatatagt aaattacggt aaaatataaa    420
taagtacata ttgaagaaaa tgagacataa tatattttat aataggaggg aatttcaaat    480
gatagacaac tttatgcagg tccttaaatt aattaaagag aaacgtacca ataatgtagt    540
taaaaatct gattgggata aaggtgatct atataaaact ttagtccatg ataagttacc    600
caagcagtta aaagtgcata taaaagaaga taaatattca gttgtaggga aggttgctac    660
tgggaactat agtaaagttc cttggatttc aatatatgat gagaatata    709
```

<210> SEQ ID NO 2
<211> LENGTH: 980
<212> TYPE: DNA
<213> ORGANISM: Staphylococcus aureus

<400> SEQUENCE: 2

```
taaatgtcag gaaatatatca aaaactgcaa aaaatattgg tataataaga gggaacagtg     60
tgaacaagtt aataacttgt ggataactgg aaagttgata acaatttgga ggaccaaacg    120
acatgaaaat caccattttta gctgtaggga aactaaaaga gaaatattgg aagcaagcca    180
tagcagaata tgaaaaacgt ttaggcccat acaccaagat agacatcata gaagttccag    240
```

| acgaaaaagc | accagaaaat | atgagcgaca | aagaaattga | gcaagtaaaa | gaaaagaag  | 300 |
| gccaacgaat | actagccaaa | attaaaccac | aatccacagt | cattacatta | gaaatacaag | 360 |
| gaaagatgct | atcttccgaa | ggattggccc | aagaattgaa | ccaacgcatg | acccaagggc | 420 |
| aaagcgactt | tgtattcgtc | attggcggat | caaacggcct | gcacaaggac | gtcttacaac | 480 |
| gcagtaacta | cgcactatca | ttcagcaaaa | tgacattccc | acatcaaatg | atgcgggttg | 540 |
| tgttaattga | gcaagtgtat | agagcattta | agattatgcg | tggagaagca | tatcataaat | 600 |
| gatgcggttt | tttcagccgc | ttcataaagg | gattttgaat | gtatcagaac | atatgaggtt | 660 |
| tatgtgaatt | gctgttatgt | ttttaagaag | cttatcataa | gtaatgaggt | tcatgatttt | 720 |
| tgacatagtt | agcctccgca | gtctttcatt | tcaagtaaat | aatagcgaaa | tattctttat | 780 |
| actgaatact | tatagtgaag | caaagttcta | gctttgagaa | aattcttttct | gcaactaaat | 840 |
| atagtaaatt | acggtaaaat | ataaataagt | acatattgaa | gaaaatgaga | cataatatat | 900 |
| tttataatag | gagggaattt | caaatgatag | acaactttat | gcaggtcctt | aaattaatta | 960 |
| aagagaaacg | taccaataat |            |            |            |            | 980 |

<210> SEQ ID NO 3
<211> LENGTH: 782
<212> TYPE: DNA
<213> ORGANISM: Staphylococcus aureus

<400> SEQUENCE: 3

| caatgcccac | agagttatcc | acaaatacac | aggttataca | ctaaaaattg | ggcatgaatg | 60  |
| tcagaaaaat | atcaaaaact | gcaaagaata | ttggtataat | aagagggaac | agtgtgaaca | 120 |
| agttaataac | ttgtggataa | ctggaaagtt | gataacaatt | tggaggacca | aacgacatga | 180 |
| aaatcaccat | tttagctgta | gggaaactaa | agagaaaata | ttggaagcaa | gccatagcag | 240 |
| aatatgaaaa | acgtttaggc | ccatacacca | agatagacat | catagaagtt | ccagacgaaa | 300 |
| aagcaccaga | aaatatgagc | gacaaagaaa | ttgagcaagt | aaaagaaaaa | gaaggccaac | 360 |
| gaatactagc | caaaatcaaa | ccacaatcaa | cagtcattac | attagaaata | caaggaaaga | 420 |
| tgctatcttc | cgaaggattg | gcccaagaat | tgaaccaacg | catgacccaa | gggcaaagcg | 480 |
| actttgtatt | cgtcattggc | ggatcaaacg | gcctgcacaa | ggacgtctta | caacgcagta | 540 |
| actacgcact | atcattcagc | aaaatgacat | tcccacatca | aatgatgcgg | ttgtgttaa  | 600 |
| ttgaacaagt | gtacagagca | tttaagatta | tgcgtggaga | agcgtatcat | aaataaaact | 660 |
| aaaaattagg | ttgtgtataa | tttaaaaatt | taatgagatg | tggaggaatt | acatatatga | 720 |
| aatattggat | tataccttgc | aatatcatac | gatgtttata | gagtgtttaa | taaaccattt | 780 |
| tt         |            |            |            |            |            | 782 |

<210> SEQ ID NO 4
<211> LENGTH: 2153
<212> TYPE: DNA
<213> ORGANISM: Staphylococcus aureus

<400> SEQUENCE: 4

| ctgtagggaa | actaaaagag | aaatactgga | agcaagccat | agcagaatat | gaaaaacgtt | 60  |
| taggcccata | caccaagata | gacatcatag | aagttccaga | cgaaaaagca | ccagaaaata | 120 |
| tgagcgacaa | agaaatcgag | caagtaaaag | aaaagaagg  | ccaacgaata | ctagccaaaa | 180 |
| tcaaaccaca | atccacagtc | attacattag | aaatacaagg | aaagatgcta | tcttccgaag | 240 |
| gattggccca | agaattgaac | caacgcatga | cccaagggca | aagcgacttt | gtattcgtca | 300 |

```
ttggcggatc aaacggcctg cacaaggacg tcttacaacg cagtaactac gcactatcat    360
tcagcaaaat gacattccca catcaaatga tgcgggttgt gttaattgaa caagtgtaca    420
gagcatttaa gattatgcgt ggagaagcgt accacaaatg atgcggtttt ttatccagtt    480
ttttgtttaa tgaacaaggt aaattacgag ataatatttg aagaaaacaa taaagtagag    540
atggatttcc atatcctctt tagtagcggt ttttatctgt aaggtttatt aataattaaa    600
taaataggcg ggatagttat atatagctta ttaatgaaag aatatgatta ttaatttagt    660
attatatttt aatattaaaa agaagatatg aataaattat tcataccttc caccttacaa    720
taattagttt tcaatcgaat attaagatta ttagtagtct taaaagttaa gacttcctta    780
tattaatgac ctaatttatt atttgcctca tgaattatct ttttatttct ttgatatgtc    840
ccaaaccaca tcgtgatata cactacaata aatattatga tgaaactaat aatattctca    900
aagttcagat ggaaccaacc tgctagaata gcgagtggga agaataggat tatcatcaat    960
ataaagtgaa ctacagtctg ttttgttata ctccaatcgg tatctgtaaa tatcaaatta   1020
ccataagtaa acaaaattcc aatcaatgcc catagtgcta cacatattag cataataacc   1080
gcttcattaa agttttcata ataaatttta cccataaaag aatctggata tagtggtaca   1140
tatttatccc ttgaaaaaaa taagtgaagt aatgacagaa atcataagac cagtgaacgc   1200 accttttga acagcgtgga ataattttt catagtgaga tggaccattc catttgtttc   1260
taacttcaag tgatcaatgt aatttagatt gataatttct gattttgaaa tacgcacgaa   1320
tattgaaccg acaagctctt caatttggta aagtcgctga taaagttta aagctttatt   1380 attcattgtt atcgcatacc tgtttatctt ctactatgaa ctgtgcaatt tgttctagat   1440
caattgggta aacatgatgg ttctgttgca aagtaaaaaa atatagctaa ccactaattt   1500
atcatgtcag tgttcgctta acttgctagc atgatgctaa tttcgtggca tggcgaaaat   1560
ccgtagatct gatgagacct gcggttcttt ttatatagag cgtaaataca ttcaatacct   1620
tttaaagtat tctttgctgt attgatactt tgataccttg tctttcttac tttaatatga   1680
cggtgatctt gctcaatgag gttattcaaa tatttcgatg tacaatgaca gtcaggttta   1740
agtttaaaag ctttaattac tttagccatt gctaccttcg ttgaaggtgc ctgatctgta   1800
attacctttt gaggtttacc aaattgttta atgagacgtt taataaacgc atatgctgaa   1860
tgattatctc gttgcttacg caaccaaata tctaatgtat gtccctctgc atcaatggca   1920
cgatataaat agctccattt tccttttatt ttgatgtacg tctcatcaat acgccatttg   1980
taataagctt ttttatgctt tttcttccaa atttgatata aaattggggc atattcttga   2040
acccaacggt agaccgttga atgatgaacg tttacaccac gtccccttaa tatttcagat   2100
atatcacgat aactcaatgc atatcttaga tagtagccaa cggctacagt gat          2153
```

<210> SEQ ID NO 5
<211> LENGTH: 1696
<212> TYPE: DNA
<213> ORGANISM: Staphylococcus aureus

<400> SEQUENCE: 5

```
aaagagaaat attggaagca agccatagca gaatatgaaa aacgtttagg cccatacacc     60
aagatagaca tcatagaagt tccagacgaa aaagcaccag aaaatatgag tgacaaagaa    120
attgagcaag taaagaaaaa agaaggccaa cgaatactag ccaaaatcaa accacaatcc    180
acagtcatta cattagaaat acaaggaaag atgctatctt ccgaaggatt ggcccaagaa    240
```

```
ttgaaccaac gcatgaccca agggcaaagc gactttgttt tcgtcattgg cggatcaaac    300
ggcctgcaca aggacgtctt acaacgcagt aactacgcac tatcattcag caaaatgaca    360
ttcccacatc aaatgatgcg ggttgtgtta attgaacaag tgtacagagc atttaagatt    420
atgcgaggag aagcatatca taaatgatgc ggttatttca gccgtaattt tataatataa    480
agcagagttt attaaatttt aatgattact ttttattaag aattaattct agttgatata    540
ttataatgtg aaacacaaaa taataatttg taattgttag tttataggca tctgtatttg    600
gaattttttg tagactattt aaaaaatagt gtatataagt attgagttca tgtattaact    660
gtctttttc atcgttcatc aagtataagg atgtagagat ttgttggata atttcttcgg    720
atgtttttaa aattatcatt aaattagatg gtatctgatc ttgagtttg ttttagtgt     780
atgtatattt taaaaatttt ttgattgttg ttatttgact ctcttttaat ttgacccct    840
catcaataaa tgtgttaaat atatcttcat ttgtacttaa atcatcaaaa tttgccaaca    900
aatatttgaa cgtctctaaa tcattatgtt tgagttccgt tttgctattc cataattcca    960
aaccatttgg tagaaagccc aagctgtgat tttgatctcc ccatatagct gaatttaaat   1020
cagtgagttg attaatttt tcaacacaga aatgtaattt tggaatgagg aatcgaagtt   1080
gttcttctac ttgctgtact tttcttttgt tttcaataaa atttctacac catactgtta   1140
tcaaaccgcc aattattgtg cacaatcctc caatgattgt agataaaatt gacaatatat   1200
tacacacctt tcttagaggt ttattaacat ctattttga atttaaaatt attactttgg   1260
tagcgttata acctatttaa cagattagag aaaaattgaa tgatcgattg aagaatttcc   1320
aaaataccgt cccatatgcg ttgaaggaga tttctatttt cttctgtatt caaatctttg   1380
gctttatcct ttgctttatt caataaatca tctgagtttt tttcaatatt ttttaataca   1440
tctttggcat tttgtttaaa tactttagga tcggaagtta gggcattaga gtttgccaca   1500
ttaatcatat tattattaat catttgaatt tgattatctg ataatatctc tgataaccta   1560
cgctcatcga ggactttatt aacagtgtct tcaacttgtt gttgtgtgat tgtttatct    1620
tgattttgtt taatatctgc aagttgttct ttaatatctg ctatagaagc atttaaagct   1680
tcatctgaat acccat                                                  1696
```

<210> SEQ ID NO 6
<211> LENGTH: 991
<212> TYPE: DNA
<213> ORGANISM: Staphylococcus aureus

<400> SEQUENCE: 6

```
accatttag ctgtagggaa actaaaagag aaatactgga agcaagccat agcagaatat     60
gaaaaacgtt taggcccata caccaagata gacatcatag aagttccaga cgaaaaagca    120
ccagaaaata tgaactacaa agaaattgag caagtaaaag aaaagaagg ccaacgaata    180
ctagccaaaa tcaaaccaca atcaacagtc attacattag aaatacaagg aaagatgcta    240
tcttccgaag gattggccca agaattgaac caacgcatga cccaagggca aagcgacttt    300
gtattcgtca ttggcggatc aaacggcctg cacaaggacg tcttacaacg cagtaactac    360
gcactatcat tcagcaaaat gacattccca catcaaatga tgcgggttgt gttaattgaa    420
caagtgtaca gagcatttaa gattatgcga ggagaagcgt atcataagtg atggtaaaaa    480
atatgagtaa gtagatgaag agtgaaaatc agattaatta ataatatgt atcaaattta     540
aataaagggg ttttaagta tgaatttaag aggtcatgaa aatagactta aatttcatgc    600
gaaatatgat gtgacaccta tcacatttt aaaattatta gaaggtcaaa agaaagacgg    660
```

```
tgaaggcggc atactgacag atagctatta ctgttttcca tacagcttaa aaggtaattc    720
taaaaaagtt ttaggtacgt ttaattgtgg ttatcatatt gctgaagatt tactaaaatt    780
atcaaatcaa gataaattac ctttatttaa cccgtttaaa gtaattaatg aaggtaatca    840
attgcagggc gtaacgaata aaggtaattt aaatattaat aggcaaagaa aacagtataa    900
tgaagtggct ttacagcttt caaatgctat taatttaatc ataatttgtt atgaggataa    960
tattaaagaa ccactttcaa cgataaaata c                                   991
```

<210> SEQ ID NO 7
<211> LENGTH: 1108
<212> TYPE: DNA
<213> ORGANISM: Staphylococcus aureus

<400> SEQUENCE: 7

```
accattttag ctgtagggaa actaaaagag aaatattgga agcaagccat agcagaatat     60
gaaaaacgtt taggcccata caccaagata gacatcatag aagttccaga cgaaaaagca    120
ccagaaaata tgagcgacaa agaaattgag caagtaaaag aaaagaagg ccaacgaata     180 ctagccaaaa tcaaaccaca atccacagtc attacattag aaatacaagg aaagatgcta    240
tcttccgaag gattggccca agaattgaac caacgcatga cccaagggca aagcgacttt    300
gtattcgtca ttggcggatc aaacggcctg cacaaggacg tcttacaacg cagtaactat    360
gcactatcat ttagcaaaat gacattccca catcaaatga tgcgggttgt gttaattgaa    420
caagtgtata gagcatttaa gattatgcgt ggagaagcgt accacaaata aaactaaaaa    480
atatgagaaa attattaaat tagctcaaat ctttgaagaa taaaaagtga atattaagtt    540
tgataattta ggtacaagta aagattaaga atttccatta tttaatacat ggtgtgtaaa    600
tcgacttctt tttgtattag atgtttgcag taagcgatgt aaagaagatg ctaataaata    660
tgtgaggaat gattacgata ctagataagc ggctaatgaa attttttaaa gtacatatat    720
agacatattt ttcatttagt aaaattttga atttcacttt gctaagacta gtgtctagaa    780
atttataatg atttattaac acctatttga aacttaagta taataaatga ttcggatttt    840 attttaata aagacaaact tgaacgtagc aaagtagttt ttatgataaa taataagttt     900
taataatgtg acgcttttat ataagcacat tattatgaac aatgtgaatt gagcatctac    960
aattacatta ataaatatat aaatgatgat ttaaattcac atatatttat aatacacata   1020
ctatatgaaa gttttgatta tccgaataaa tgctaaaatt aataaaataa ttaaaggaat   1080
catacttatt atacgtatac gtttagct                                      1108
```

<210> SEQ ID NO 8
<211> LENGTH: 1256
<212> TYPE: DNA
<213> ORGANISM: Staphylococcus aureus

<400> SEQUENCE: 8

```
gctgtaggga actaaaagag aaatattggg aagcaagcca tagcagaata tgaaaaacgt     60
ttaggcccat acaccaagat agacatcata gaagttccag acgaaaaagc accagaaaat    120
atgagcgaca aagaaattga gcaagtaaaa gaaaagaag ccaacgaat actagccaaa     180 attaaaccac aatccacagt cattacatta gaaatacaag gaaagatgct atcttccgaa    240
ggattgggcc aagaattgaa ccaacgcatg acccaagggc aaagcgactt tgtattcgtc    300
attggcggat caaacggcct gcacaaggac gtcttacaac gcagtaacta cgcactatca    360
```

-continued

| | | | | |
|---|---|---|---|---|
| ttcagcaaaa | tgacattccc | acatcaaatg | atgcggttg | tgttaattga gcaagtgtat | 420 |
| agagcattta | agattatgcg | tggagaagca | tatcataaat | gatgcggttt tttcagccgc | 480 |
| ttcataaagg | gattttgaat | gtatcagaac | atatgaggtt | tatgtgaatt gctgttatgt | 540 |
| ttttaagaag | catatcataa | gtgatgcggt | ttttattaat | tagttgctaa aaaatgaagt | 600 |
| atgcaatatt | aattattatt | aaattttgat | atatttaaag | aaagattaag tttagggtga | 660 |
| atgaatggct | tatcaaagtg | aatatgcatt | agaaaatgaa | gtacttcaac aacttgagga | 720 |
| attgaactat | gaaagagtaa | atatacataa | tattaaatta | gaaattaatg aatatctcaa | 780 |
| agaactagga | gtgttgaaaa | atgaataagc | agacaaatac | tccagaacta agatttccag | 840 |
| agtttgatga | ggaatggaaa | aaaggaaat | taggtgaagt | agtaaattat aaaaatggtg | 900 |
| gttcatttga | aagtttagtg | aaaaaccatg | gtgtatataa | actcataact cttaaatctg | 960 |
| ttaatacaga | aggaaagttg | tgtaattctg | gaaaatatat | cgatgataaa tgtgttgaaa | 1020 |
| cattgtgtaa | tgatactta | gtaatgatac | tgagcgagca | agcaccagga ctagttggaa | 1080 |
| tgactgcaat | tatacctaat | aataatgagt | atgtactaaa | tcaacgagta gcagcactag | 1140 |
| tgcctaaaca | atttatagat | agtcaatttc | tatctaagtt | aattaataga aaccagaaat | 1200 |
| atttcagtgt | gagatctgct | ggaacaaaag | tgaaaaatat | ttctaaagga catgta | 1256 |

<210> SEQ ID NO 9
<211> LENGTH: 1125
<212> TYPE: DNA
<213> ORGANISM: Staphylococcus aureus

<400> SEQUENCE: 9

| | | | | |
|---|---|---|---|---|
| accattttag | ctgtagggaa | actaaaagag | aaatattgga | agcaagccat agcagaatat | 60 |
| gaaaaacgtt | taggcccata | caccaagata | gacatcatag | aagttccaga cgaaaaagca | 120 |
| ccagaaaata | tgagcgacaa | agaaattgag | caagtaaaag | aaaagaagg ccaacgaata | 180 |
| ctagccaaaa | tcaaaccaca | atccacagtc | attacattag | aaatacaagg aaagatgcta | 240 |
| tcttccgaag | gattggccca | agaattgaac | caacgcatga | cccagggca agcgacttt | 300 |
| gtattcgtca | ttggcggatc | aaacggcctg | cacaaggacg | tcttacaacg cagtaactat | 360 |
| gcactatcat | ttagcaaaat | gacattccca | catcaaatga | tgcgggttgt gttaattgaa | 420 |
| caagtgtata | gagcattaa | gattatgcgt | ggagaggcgt | atcataaata aaactaaaaa | 480 |
| acggattgtg | tataatatat | tttaaatata | aaaaggattg | attttatgtt aaataaatta | 540 |
| gaaaatgtta | gttataaatc | attcgataat | tacactagtg | aagatgattt gactaaagta | 600 |
| aatatatttt | ttggaagaaa | tgggagtgga | aaaagctcat | taagtgaatg gttaagaaga | 660 |
| ctagataatg | aaaaaagtgt | tatctttaat | actggttact | taaaaaataa tattgaagaa | 720 |
| gttgaagaaa | tagatggtgt | gaatttggtt | attggagaag | aatctataaa tcatagtgac | 780 |
| caaattaagc | atttaaatag | cgctataaat | agtttagaaa | attttattac tcggaaaaat | 840 |
| agtgaactta | agcattcaaa | agaaagaatt | tacaataaaa | tgaatatcag actaaatgaa | 900 |
| gctagagaaa | gatttgaaat | aggtagtaat | gtggttaagc | agaagaggaa tgctgacaaa | 960 |
| gatccagtta | atgcttttta | tagttggaag | aaaaatgcta | acgatataat tcaagagatg | 1020 |
| actattgaat | ctttagatga | attagaagaa | agaataacaa | gaaagaagt cttattaaat | 1080 |
| aatataaaaa | caccaatttt | agcttttgat | tataatgatt | ttagt | 1125 |

<210> SEQ ID NO 10
<211> LENGTH: 1380

```
<212> TYPE: DNA
<213> ORGANISM: Staphylococcus aureus

<400> SEQUENCE: 10 accatttag ctgtagggaa actaaaagag aaatattgga agcaagccat agcagaatat      60
gaaaaacgtt taggcccata caccaagata gacatcatag aagttccaga cgaaaaagca     120
ccagaaaata tgagcgacaa agaaattgag caagtaaaag aaaagaagg ccaacgaata      180 ctagccaaaa ttaaaccaca atccacagtc attacattag aaatacaagg aaagatgcta    240
tcttccgaag gattggccca agaattgaac caacgcatga cccaagggca aagcgacttt    300
gtattcgtca ttggcggatc aaacggcctg cacaaggacg tcttacaacg cagtaactac    360
gcactatcat tcagcaaaat gacattccca catcaaatga tgcgggttgt gttaattgag    420
caagtgtata gagcatttaa gattatgcgt ggagaagcat atcataagtg atgcggtttt    480
tattaattag ttgctaaaaa atgaagtatg caatattaat tattattaaa ttttgatata    540
tttaaagaaa gattaagttt agggtgaatg aatggcttat caaagtgaat atgcattaga    600
aaatgaagta cttcaacaac ttgaggaatt gaactatgaa agagtaaata tacataatat    660
taaattagaa attaatgaat atctcaaaga actaggagtg ttgaaaaatg aataagcaga    720
caaatactcc agaactaaga tttccagagt ttgatgagga atggaaaaaa aggaaattag    780
gtgaagtagt aaattataaa aatggtggtt catttgaaag tttagtgaaa aaccatggtg    840
tatataaact cataactctt aaatctgtta atacagaagg aaagttgtgt aattctggaa    900
aatatatcga tgataaatgt gttgaaacat tgtgtaatga tactttagta atgatactga    960
gcgagcaagc accaggacta gttggaatga ctgcaattat acctaataat aatgagtatg   1020
tactaaatca acgagtagca gcactagtgc ctaaacaatt tatagatagt caatttctat   1080
ctaagttaat taatagaaac cagaaatatt tcagtgtgag atctgctgga acaaaagtga   1140
aaaatatttc taaggacat gtagaaaact ttaattttt atctcctaat tacactgaac     1200
aacaaaaaat aggtaatttc ttcagcaaac tcgaccgcca gattgagtta aagaagaga    1260 aacttgaact cttagagcaa caaaagcgtg gatatattca aagatttttt tctcaagatt   1320
taagatttaa agatgaaaat ggaaacagtt atcctgattg gtctattaaa aagattgaag   1380

<210> SEQ ID NO 11
<211> LENGTH: 1200
<212> TYPE: DNA
<213> ORGANISM: Staphylococcus aureus

<400> SEQUENCE: 11 accatttag ctgtagggaa actaaaagag aaatattgga agcaagccat agcagaatat      60
gaaaaacgtt taggcccata caccaagata gacatcatag aagttccaga cgaaaaagca     120
ccagaaaata tgagcgacaa agaaattgag caagtaaaag aaaagaagg ccaacgaata      180 ctagccaaaa ttaaaccaca atccacagtc attacattag aaatacaagg aaagatgcta    240
tcttccgaag gattggccca agaattgaac caacgcatga cccaagggca aagcgacttt    300
gtattcgtca ttggcggatc aaacggcctg cacaaggacg tcttacaacg cagtaactac    360
gcactatcat tcagcaaaat gacattccca catcaaatga tgcgggttgt gttaattgag    420
caagtgtata gagcatttaa gattatgcgt ggagaagcat atcataaatg atgcggtttt    480
ttcagccgct tcataaaggg attttgaatg tatcagaaca tatgaggttt atgtgaattg    540
ctgttatgtt tttaagaagc atatcataaa tgatgcggtt ttttcagccg cttcataaag   600
```

```
ggattttgaa tgtatcagaa catatgaggt ttatgtgaat tgctgttatg tttttaagaa      660
gcatatcata agtgatgcgg tttttattaa ttagttgcta aaaaatgaag tatgcaatat      720
taattattat taaattttga tatatttaaa gaaagattaa gtttagggtg aatgaatggc      780
ttatcaaagt gaatatgcat tagaaaatga agtacttcaa caacttgagg aattgaacta      840
tgaaagagta aatatacata atattaaatt agaaattaat gaatatctca agaactagg       900 agtgttgaaa atgaataag cagacaaata ctccagaact aagatttcca gagtttgatg       960
aggaatggaa aaaaggaaa ttaggtgaag tagtaaatta taaaaatggt ggttcatttg      1020
aaagtttagt gaaaaaccat ggtgtatata aactcataac tcttaaatct gttaatacag     1080
aaggaaagtt gtgtaattct ggaaaatata tcgatgataa atgtgttgaa acattgtgta     1140
atgatacttt agtaatgata ctgagcgagc aagcaccagg actagttgga atgactgcaa    1200
```

<210> SEQ ID NO 12
<211> LENGTH: 1017
<212> TYPE: DNA
<213> ORGANISM: Staphylococcus aureus

<400> SEQUENCE: 12

```
aacgtttagg cccatacacc aagatagaca tcatagaagt tccagacgaa aaagcaccag       60
aaaatatgag cgacaaagaa atcgagcaag taaaagaaaa agaaggccaa cgaatactag      120
ccaaaatcaa accacaatcc acagtcatta cattagaaat acaaggaaag atgctatctt      180
ccgaaggatt ggcccaagaa ttgaaccaac gcatgaccca agggcaaagc gactttgtat      240
tcgtcattgg cggatcaaac ggcctgcaca aggacgtctt acaacgcagt aactacgcac      300
tatcattcag caaaatgaca ttcccacatc aaatgatgcg ggttgtgtta attgaagcaa      360
gtgtatagag cgtttaagat tatgcgcgga gaagcgtatc acaaatgatg cggttttttt      420 aacctctta cgtatgaggt ttatgagaat tgccgttatg ttttgcgaga gttatcaatc       480 ttttgatag taagaaagta catagaaact aaaagagtat ttttatctac aatagcattt       540
ataatttatt ctattattgt atacttattt taattattag tatcattgct gagatgttac      600
ttgatattct atgtctattt tttaggaaat tctatactat taaaattatg gtattttata      660
cgcaataaag gactaatcta ttttatacag attagtcctt tattgtagtc tttaaaaact      720
agttactcat taatatttt tagtacaatt tcagcaacct cacttactat tttgtcatta       780
ggtttaccat cttttctatc tttatttgta aatatcacca gaattatagg tttatcttgt      840
ccatctggat aaacaaagcg aacatcgttt cttgaaccgt atgttagtgc ttgaccgctc      900
ttatccataa cttttaaagtt tgaaggtgca ccatccttaa ttaatgtatc gccactttta    960
tttttgaaca ttagattaag taagaaatct ttgtttgctt tgctaagatc tccatca       1017
```

<210> SEQ ID NO 13
<211> LENGTH: 2207
<212> TYPE: DNA
<213> ORGANISM: Staphylococcus aureus

<400> SEQUENCE: 13

```
ccttctacac ctccatatca caaaaattat aacattattt tgacataaat actacatttg       60
taatatacta caaatgtagt cttatataag gaggatattg atgaaaaaga taaaaattgt      120
tccacttatt ttaatagttg tagttgtcgg gtttggtata tatttttatg cttccaaaga      180
taaagaaatt aataatacta ttgatgcaat tgaagataaa aatttcaaac aagttttataa     240 agatagcagt tatatttcta aaagcgataa tggtgaagta gaaatgactg aacgtccgat      300
```

```
aaaaatatat aatagtttag gcgttaaaga tataaacatt caggatcgta aaataaaaaa      360
agtatctaaa aataaaaaac gagtagatgc tcaatataaa attaaaacaa actacggtaa      420
cattgatcgc aacgttcaat ttaattttgt taaagaagat ggtatgtgga agttagattg      480
ggatcatagc gtcattattc caggaatgca gaaagaccaa agcatacata ttgaaaattt      540
aaaatcagaa cgtggtaaaa ttttagaccg aaacaatgtg gaattggcca atacaggaac      600
agcatatgag ataggcatcg ttccaaagaa tgtatctaaa aaagattata aagcaatcgc      660
taaagaacta agtatttctg aagactatat caaacaacaa atggatcaaa attgggtaca      720
agatgatacc ttcgttccac ttaaaaccgt taaaaaatg gatgaatatt taagtgattt       780
cgcaaaaaaa tttcatctta caactaatga aacagaaagt cgtaactatc ctctaggaaa      840
agcgacttca catctattag gttatgttgg tcccattaac tctgaagaat taaaacaaaa      900
agaatataaa ggctataaag atgatgcagt tattggtaaa aagggactcg aaaaacttta      960
cgataaaaag ctccaacatg aagatggcta tcgtgtcaca atcgttgacg ataatagcaa     1020
tacaatcgca catacattaa tagagaaaaa gaaaaaagat ggcaaagata ttcaactaac     1080
tattgatgct aaagttcaaa agagtattta taacaacatg aaaaatgatt atggctcagg     1140
tactgctatc caccctcaaa caggtgaatt attagcactt gtaagcacac cttcatatga     1200
cgtctatcca tttatgtatg gcatgagtaa cgaagaatat aataaattaa ccgaagataa     1260
aaaagaacct ctgctcaaca agttccagat tacaacttca ccaggttcaa ctcaaaaaat     1320
attaacagca atgattgggt taaataacaa aacattagac gataaaacaa gttataaaat     1380
cgatggtaaa ggttggcaaa aagataaatc ttggggtggt tacaacgtta caagatatga     1440
agtggtaaat ggtaatatcg acttaaaaca agcaatagaa tcatcagata acattttctt     1500
tgctagagta gcactcgaat taggcagtaa gaaatttgaa aaaggcatga aaaaactagg     1560
tgttggtgaa gataaccaa gtgattatcc attttataat gctcaaattt caaacaaaaa      1620
tttagataat gaaatattat tagctgattc aggttacgga caaggtgaaa tactgattaa     1680
cccagtacag atcctttcaa tctatagcgc attagaaaat aatggcaata ttaacgcacc     1740
tcacttatta aaagacacga aaacaaagt ttggaagaaa aatattattt ccaaagaaaa      1800
tatcaatcta ttaactgatg gtatgcaaca agtcgtaaat aaaacacata agaagatat      1860 ttatagatct tatgcaaact taattggcaa atccggtact gcagaactca aaatgaaaca     1920
aggagaaact ggcagacaaa ttgggtggtt tatatcatat gataaagata atccaaacat     1980
gatgatggct attaatgtta aagatgtaca agataaagga atggctagct acaatgccaa     2040
aatctcaggt aaagtgtatg atgagctata tgagaacggt aataaaaaat acgatataga     2100
tgaataacaa aacagtgaag caatccgtaa cgatggttgc ttcactgttt tattatgaat     2160
tattaataag tgctgttact tctcccttaa atacaatttc ttcattt                   2207
```

<210> SEQ ID NO 14
<211> LENGTH: 1998
<212> TYPE: DNA
<213> ORGANISM: Staphylococcus aureus

<400> SEQUENCE: 14

```
atgaaaaaaa tttatattag tgtgctagtt cttttactaa ttatgattat aataacttgg       60
ttattcaaag atgacgatat tgagaaaaca attagttcta ttgaaaaagg aaactataac      120
gaagtatata aaaatagttc agaaaaatct aaactggcat atggagaaga agaaattgta      180
```

```
gataggaata aaaaaattta caaagattta agtgtcaata acttaaaaat tactaatcat    240
gaaattaaaa aaactggaaa agataaaaag caagttgatg ttaaatataa catatataca    300
aaatatggaa ctatacgacg taatacacaa ttaaacttta tttatgaaga taagcattgg    360
aaattagatt ggagaccaga cgtaatagta cctggtttga aaaatggaca gaaaattaat    420
atagaaacat taaaatcaga gcgaggcaaa ataaaagata gaaatggtat agaattagct    480
aaaactggaa atacatatga aatcggtatt gtccctaaca aaacacccaa agaaaaatat    540
gatgatattg ctcgtgactt acaaattgat acaaaagcta taaccaataa agttaatcaa    600
aaatgggttc agccagattc atttgtacca attaaaaaga taaataaaca agatgaatat    660
atagacaaat taattaaatc atacaattta caaataaaca ctataaaaag ccgtgtttat    720
ccattgaacg aagcaacagt acaccttttta ggttatgtgg gtccaattaa ttctgacgag    780
ttaaaaagta agcaatttag aaactatagc aaaaatactg ttattggaaa aaaaggctta    840
gaacgcctct atgataaaca attgcaaaac actgatggtt ttaaggtatc cattgcaaat    900
acttatgaca ataaaccttt agacacatta ttggagaaaa aggctgaaaa cggaaaagat    960
cttcatttaa ctatagatgc tagagtacaa gaaagtattt ataaacatat gaaaaatgac   1020
gatggatctg gtacagcatt acaaccaaaa actggagaaa ttttagcttt ggtaagtacc   1080
ccatcgtacg atgtttatcc attcatgaat ggattaagca ataatgacta ccgtaaatta   1140
actaacaata aaaaagagcc tttgctcaac aaatttcaaa tcactacatc accaggttca   1200
acccaaaaaa tattaacatc tattatagcc ttaaaagaaa ataaactaga caaaaatact   1260
aattttgata tttatggtaa gggttggcaa aaagatgcat catgggggaa ttataatatc   1320
acaagattta agtagtaga cggcaatatc gatttaaagc aagcaataga atcatcagac   1380
aacatatttt tgcccgcat tgcattagca ttaggagcca aaaaatttga gcaaggtatg   1440
caagatttgg gaatcggtga aaatatcccg agtgattatc ccttttataa agcacaaatc   1500
tcaaatagta atttaaaaaa tgaaatatta ttagcagatt caggatatgg ccaaggcgag   1560
atactagtaa acccctataca aatttttatca atatacagtg ctttagaaaa taacggaaat   1620
atacaaaatc ctcatgttttt acgtaaaaca aaatctcaaa tatggaaaaa agatattata   1680
cctaaaaaag acatagatat attaactaat ggtatggaac gtgtagttaa taaaacacat   1740
agggatgata tatacaaaaa ttatgcccga attattggta atctggcac agcagaatta   1800 aaaatgaatc aaggggaaac tggaagacaa ataggttggt ttgtttcata taataaaaat   1860
aatcctaata tgttaatggc gattaatgtt aaagacgttc aaaataaagg gatggccagc   1920
tataatgcta ctatatctgg aaaagtttat gatgatttgt atgataatgg aaaaactcaa   1980
tttgatatag atcagtaa                                                1998

<210> SEQ ID NO 15
<211> LENGTH: 1011
<212> TYPE: DNA
<213> ORGANISM: Staphylococcus aureus

<400> SEQUENCE: 15
atggcagtaa aagtagcaat taatggtttt ggtagaattg gtcgtttagc attcagaaga     60
attcaagaag tagaaggtct tgaagttgta gcagtaaacg acttaacaga tgacgacatg    120
ttagcgcatt tattaaaata tgacactatg caaggtcgtt tcacaggtga agtagaggta    180
gttgatggtg gtttccgcgt aaatggtaaa gaagttaaat cattcagtga accagatgca    240
agcaaattac cttggaaaga cttaaatatc gatgtagtat tagaatgtac tggttttctac    300
```

```
actgataaag ataaagcaca agctcatatt gaagcaggcg ctaaaaaagt attaatctca    360
gcaccagcta ctggtgactt aaaaacaatc gtattcaaca ctaaccacca agagttagac    420
ggttctgaaa cagttgtttc aggtgcttca tgtactacaa actcattagc accagttgct    480
aaagttttaa acgatgactt tggtttagtt gaaggtttaa tgactacaat tcacgcttac    540
acaggtgatc aaaatacaca agacgcacct cacagaaaag gtgacaaacg tcgtgctcgt    600
gcagcggcag aaaacatcat ccctaactca acaggtgctg ctaaagctat cggtaaagtt    660
attcctgaaa tcgatggtaa attagatggt ggtgcacaac gtgttcctgt agctacaggt    720
tcattaactg aattaacagt agtattgaa aaacaagacg taacagttga acaagttaac    780
gaagctatga aaaatgcttc aaacgaatca ttcggttaca ctgaagacga aatcgtttct    840
tcagacgttg taggtatgac ttacggttca ttattcgacg ctacacaaac tcgtgtaatg    900
tcagttggcg accgtcaatt agttaaagtt gcagcttggt atgataacga aatgtcatat    960
actgcacaat tagttcgtac attagcatac ttagctgaac tttctaaata a    1011
```

<210> SEQ ID NO 16
<211> LENGTH: 356
<212> TYPE: DNA
<213> ORGANISM: Staphylococcus aureus

<400> SEQUENCE: 16

```
aacgtttagg cccatacacc aagatagaca tcatagaagt tccagacgaa aaagcaccag     60
aaaatatgag cgacaaagaa atcgagcaag taaagaaaa agaaggccaa cgaatactag    120
ccaaaatcaa accacaatcc acagtcatta cattagaaat acaggaaag atgctatctt    180 ccgaaggatt ggcccaagaa ttgaaccaac gcatgaccca agggcaaagc gactttgtat    240
tcgtcattgg cggatcaaac ggcctgcaca aggacgtctt acaacgcagt aactacgcac    300
tatcattcag caaaatgaca ttcccacatc aaatgatgcg ggttgtgtta attgaa       356
```

<210> SEQ ID NO 17
<211> LENGTH: 819
<212> TYPE: DNA
<213> ORGANISM: Staphylococcus aureus

<400> SEQUENCE: 17

```
aacgtttagg cccatacacc aagatagaca tcatagaagt tccagacgaa aaagcaccag     60
aaaatatgag cgacaaagaa atcgagcaag taaagaaaa agaaggccaa cgaatactag    120
ccaaaatcaa accacaatcc acagtcatta cattagaaat acaggaaag atgctatctt    180 ccgaaggatt ggcccaagaa ttgaaccaac gcatgaccca agggcaaagc gactttgtat    240
tcgtcattgg cggatcaaac ggcctgcaca aggacgtctt acaacgcagt aactacgcac    300
tatcattcag caaaatgaca ttcccacatc aaatgatgcg ggttgtgtta attgaacaag    360
tgtatagagc atttaagatt atgcgaggag aagcgtatca caaataaaac taaaaaatag    420
attgtgtata atataaaagg aagggattta tattaaaatt ttgaattcaa aaattattga    480
aagggaagct accttagaaa ttgaatctat ggccactaat acattgaaaa taaacccaga    540
cattaattct tactatacag aaatgtcttt cgatggagaa ttggaagtgt atgatcctga    600
aaatttgaat aaaaaatttc gttggaaaaa tacaagttca agttaaagga aagaagtag    660 ctaaaagagg aggtaagatt attcgtcgaa gtaatgggtt ctgttgcaaa gtaaaaaaat    720
atagctaacc actaatttat catgtcagtg ttcgcttaac gatataaata gctccatttt    780
```

```
ccttttattt tgatgtacgt ctcatcaata cgccatttg                            819
```

<210> SEQ ID NO 18
<211> LENGTH: 868
<212> TYPE: DNA
<213> ORGANISM: Staphylococcus aureus

<400> SEQUENCE: 18

```
accattttag ctgtagggaa actaaaagag aaatattgga agcaagccat agcagaatat     60
gaaaaacgtt taggcccata caccaagata gacatcatag aagttccaga cgaaaaagca    120
ccagaaaata tgagtgacaa agaaattgag caagtaaaag aaaagaagg  ccaacgaata    180
ctagccaaaa tcaaaccaca atccacagtc attacattag aaatacaagg aaagatgcta    240
tcttccgaag gattggccca agaattgaac caacgcatga cccaagggca aagcgacttt    300
gttttcgtca ttggcggatc aaacggcctg cacaaggacg tcttacaacg cagtaactac    360
gcactatcat tcagcaaaat gacattccca catcaaatga tgcgggttgt gttaattgaa    420
caagtgtaca gagcatttaa gattatgcga ggagaagcgt atcacaaata aaactaaaaa    480
atagattgtg tataatataa aaggagcgga tttatattaa aactttgaat tcaaaaatta    540
ttgaaaggga agctaccta  gaaattgaat ctatggcaac taatacattg aaaataaacc    600
cggatattaa ttcaaacgat acaaaaatgt ctttcgatgg agaattggaa gtgtatgatt    660
ctgaaaattt gagtaaaaaa aatttcgttg gaaaaatcaa agttcaagtt aaaggaaagg    720
aagtagctaa agaggaggt  aaggttattc atcgaagtaa tgtcaaaatg aatgatttaa    780
aggcatacca acgagaaggt ggtgtgtatt actttgtcgt gtatttaatc gttgagaata    840
aaaaagttgt tgagaagcag gtttatgg                                       868
```

<210> SEQ ID NO 19
<211> LENGTH: 36
<212> TYPE: DNA
<213> ORGANISM: Artificial Sequence
<220> FEATURE:
<223> OTHER INFORMATION: GAPDH FRET Cassette
<220> FEATURE:
<221> NAME/KEY: misc_feature
<222> LOCATION: (1)..(1)
<223> OTHER INFORMATION: Cal Fluor Red 610 labeled
<220> FEATURE:
<221> NAME/KEY: misc_feature
<222> LOCATION: (4)..(4)
<223> OTHER INFORMATION: Black Hole Quencher 2-dT
<220> FEATURE:
<221> NAME/KEY: misc_feature
<222> LOCATION: (35)..(35)
<223> OTHER INFORMATION: 3'-terminal Hexanediol

<400> SEQUENCE: 19

```
tcttagccgg ttttccggct gagactccgc gtccgt                               36
```

<210> SEQ ID NO 20
<211> LENGTH: 24
<212> TYPE: DNA
<213> ORGANISM: Artificial Sequence
<220> FEATURE:
<223> OTHER INFORMATION: GAPDH Forward amplification oligomer

<400> SEQUENCE: 20

```
cgtttcacag gtgaagtaga ggta                                            24
```

<210> SEQ ID NO 21
<211> LENGTH: 29

```
<212> TYPE: DNA
<213> ORGANISM: Artificial Sequence
<220> FEATURE:
<223> OTHER INFORMATION: GAPDH Reverse amplification oligomer
<220> FEATURE:
<221> NAME/KEY: modified_base
<222> LOCATION: (1)..(29)
<223> OTHER INFORMATION: n = 5'-methyl-2'deoxycytosine
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t

<400> SEQUENCE: 21
cnagtanatt ntaatantan atngatatt                                          29

<210> SEQ ID NO 22
<211> LENGTH: 30
<212> TYPE: DNA
<213> ORGANISM: Artificial Sequence
<220> FEATURE:
<223> OTHER INFORMATION: GAPDH detection oligomer
<220> FEATURE:
<221> NAME/KEY: misc_feature
<222> LOCATION: (30)..(30)
<223> OTHER INFORMATION: 3'-terminal Hexanediol

<400> SEQUENCE: 22
acggacgcgg agagttgatg gtggtttccg                                         30

<210> SEQ ID NO 23
<211> LENGTH: 32
<212> TYPE: DNA
<213> ORGANISM: Artificial Sequence
<220> FEATURE:
<223> OTHER INFORMATION: GAPDH Forward amplification oligomer

<400> SEQUENCE: 23
cgcgtaaatg gtaaagaagt taaatcattc ag                                      32

<210> SEQ ID NO 24
<211> LENGTH: 27
<212> TYPE: DNA
<213> ORGANISM: Artificial Sequence
<220> FEATURE:
<223> OTHER INFORMATION: GAPDH Reverse amplification oligomer

<400> SEQUENCE: 24
gagcttgtgc tttatcttta tcagtgt                                            27

<210> SEQ ID NO 25
```

```
<211> LENGTH: 30
<212> TYPE: DNA
<213> ORGANISM: Artificial Sequence
<220> FEATURE:
<223> OTHER INFORMATION: GAPDH detection oligomer
<220> FEATURE:
<221> NAME/KEY: misc_feature
<222> LOCATION: (30)..(30)
<223> OTHER INFORMATION: 3'-terminal Hexanediol

<400> SEQUENCE: 25
acggacgcgg aggtgaacca gatgcaagca                                    30

<210> SEQ ID NO 26
<211> LENGTH: 26
<212> TYPE: DNA
<213> ORGANISM: Artificial Sequence
<220> FEATURE:
<223> OTHER INFORMATION: GAPDH Reverse amplification oligomer

<400> SEQUENCE: 26
ctgtttcaga accgtctaac tcttgg                                        26

<210> SEQ ID NO 27
<211> LENGTH: 35
<212> TYPE: DNA
<213> ORGANISM: Artificial Sequence
<220> FEATURE:
<223> OTHER INFORMATION: mecA/C FRET Cassette
<220> FEATURE:
<221> NAME/KEY: misc_feature
<222> LOCATION: (1)..(1)
<223> OTHER INFORMATION: Hexochloro-Fluorescein labeled
<220> FEATURE:
<221> NAME/KEY: misc_feature
<222> LOCATION: (4)..(4)
<223> OTHER INFORMATION: Blackberry Quencher 650 dT
<220> FEATURE:
<221> NAME/KEY: misc_feature
<222> LOCATION: (35)..(35)
<223> OTHER INFORMATION: 3'-terminal Hexanediol

<400> SEQUENCE: 27
tctagccggt tttccggctg agacgtccgt ggcct                              35

<210> SEQ ID NO 28
<211> LENGTH: 43
<212> TYPE: DNA
<213> ORGANISM: Artificial Sequence
<220> FEATURE:
<223> OTHER INFORMATION: mecC detection oligomer
<220> FEATURE:
<221> NAME/KEY: misc_feature
<222> LOCATION: (43)..(43)
<223> OTHER INFORMATION: 3'-terminal Hexanediol

<400> SEQUENCE: 28
acggacgcgg agcatctatt atagccttaa aagaaaataa act                     43

<210> SEQ ID NO 29
<211> LENGTH: 38
<212> TYPE: DNA
<213> ORGANISM: Artificial Sequence
<220> FEATURE:
<223> OTHER INFORMATION: mecA detection oligomer
<220> FEATURE:
<221> NAME/KEY: misc_feature
<222> LOCATION: (38)..(38)
<223> OTHER INFORMATION: 3'-terminal Hexanediol

<400> SEQUENCE: 29
```
acggacgcgg agtcgatttt ataacttgtt ttatcgtc                                38

<210> SEQ ID NO 30
<211> LENGTH: 25
<212> TYPE: DNA
<213> ORGANISM: Artificial Sequence
<220> FEATURE:
<223> OTHER INFORMATION: mecA/C Forward amplification oligomer

<400> SEQUENCE: 30
ttatcttttt gccaaccttt accat                                              25

<210> SEQ ID NO 31
<211> LENGTH: 29
<212> TYPE: DNA
<213> ORGANISM: Artificial Sequence
<220> FEATURE:
<223> OTHER INFORMATION: mecA/C Reverse amplification oligomer

<400> SEQUENCE: 31
tcaccaggtt caactcaaaa aatattaac                                          29

<210> SEQ ID NO 32
<211> LENGTH: 43
<212> TYPE: DNA
<213> ORGANISM: Artificial Sequence
<220> FEATURE:
<223> OTHER INFORMATION: mecC detection oligomer
<220> FEATURE:
<221> NAME/KEY: misc-feature
<222> LOCATION: (43)..(43)
<223> OTHER INFORMATION: 3'-terminal Hexanediol

<400> SEQUENCE: 32
aggccacgga cgcatctatt atagccttaa aagaaaataa act                          43

<210> SEQ ID NO 33
<211> LENGTH: 38
<212> TYPE: DNA
<213> ORGANISM: Artificial Sequence
<220> FEATURE:
<223> OTHER INFORMATION: mecA detection oligomer
<220> FEATURE:
<221> NAME/KEY: misc_feature
<222> LOCATION: (38)..(38)
<223> OTHER INFORMATION: 3'-terminal Hexanediol

<400> SEQUENCE: 33
aggccacgga cgtcgatttt ataacttgtt ttatcgtc                                38

<210> SEQ ID NO 34
<211> LENGTH: 23
<212> TYPE: DNA
<213> ORGANISM: Artificial Sequence
<220> FEATURE:
<223> OTHER INFORMATION: mecA/C Forward amplification oligomer
<220> FEATURE:
<221> NAME/KEY: mod_base
<222> LOCATION: (1)..(23)
<223> OTHER INFORMATION: n = 5'-methyl-2'deoxycytosine
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (10)..(11)
<223> OTHER INFORMATION: n is a, c, g, or t
<220> FEATURE:

```
<221> NAME/KEY: misc_feature
<222> LOCATION: (14)..(15)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t

<400> SEQUENCE: 34 atnttttgn naanntttan nat                                           23

<210> SEQ ID NO 35
<211> LENGTH: 29
<212> TYPE: DNA
<213> ORGANISM: Artificial Sequence
<220> FEATURE:
<223> OTHER INFORMATION: mecA/C Reverse amplification oligomer
<220> FEATURE:
<221> NAME/KEY: mod_base
<222> LOCATION: (1)..(29)
<223> OTHER INFORMATION: n = 5'-methyl-2'deoxycytosine
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t

<400> SEQUENCE: 35
tnannaggtt naantnaaaa aatattaac                                    29

<210> SEQ ID NO 36
<211> LENGTH: 35
<212> TYPE: DNA
<213> ORGANISM: Artificial Sequence
<220> FEATURE:
<223> OTHER INFORMATION: mecA/C Forward amplification oligomer

<400> SEQUENCE: 36
gcaaagaaaa tgttgtctga tgattctatt gcttg                             35

<210> SEQ ID NO 37
<211> LENGTH: 30
<212> TYPE: DNA
<213> ORGANISM: Artificial Sequence
<220> FEATURE:
<223> OTHER INFORMATION: mecA/C Forward amplification oligomer

<400> SEQUENCE: 37
gaaaatgttg tctgatgatt ctattgcttg                                   30

<210> SEQ ID NO 38
<211> LENGTH: 30
<212> TYPE: DNA
<213> ORGANISM: Artificial Sequence
<220> FEATURE:
<223> OTHER INFORMATION: mecA Reverse amplification oligomer
```

```
<400> SEQUENCE: 38
cttggggtgg ttacaacgtt acaagatatg                                     30

<210> SEQ ID NO 39
<211> LENGTH: 26
<212> TYPE: DNA
<213> ORGANISM: Artificial Sequence
<220> FEATURE:
<223> OTHER INFORMATION: mecA/C Forward amplification oligomer

<400> SEQUENCE: 39
cctgaatctg ctaataatat ttcatt                                         26

<210> SEQ ID NO 40
<211> LENGTH: 22
<212> TYPE: DNA
<213> ORGANISM: Artificial Sequence
<220> FEATURE:
<223> OTHER INFORMATION: mecA forward amplification oligomer

<400> SEQUENCE: 40
gtgtctttta ataagtgagg tg                                             22

<210> SEQ ID NO 41
<211> LENGTH: 29
<212> TYPE: DNA
<213> ORGANISM: Artificial Sequence
<220> FEATURE:
<223> OTHER INFORMATION: mecA detection oligomer
<220> FEATURE:
<221> NAME/KEY: misc_feature
<222> LOCATION: (29)..(29)
<223> OTHER INFORMATION: 3'-terminal Hexanediol

<400> SEQUENCE: 41
aggccacgga cgcgtaacct gaatcagct                                      29

<210> SEQ ID NO 42
<211> LENGTH: 26
<212> TYPE: DNA
<213> ORGANISM: Artificial Sequence
<220> FEATURE:
<223> OTHER INFORMATION: mecA Invader

<400> SEQUENCE: 42
gggttaatca gtatttcacc ttgtca                                         26

<210> SEQ ID NO 43
<211> LENGTH: 28
<212> TYPE: DNA
<213> ORGANISM: Artificial Sequence
<220> FEATURE:
<223> OTHER INFORMATION: mecA detection oligomer
<220> FEATURE:
<221> NAME/KEY: misc_feature
<222> LOCATION: (28)..(28)
<223> OTHER INFORMATION: 3'-terminal Hexanediol

<400> SEQUENCE: 43
aggccacgga cgcaccttgt ccgtaacc                                       28

<210> SEQ ID NO 44
<211> LENGTH: 28
<212> TYPE: DNA
<213> ORGANISM: Artificial Sequence
<220> FEATURE:
```

```
<223> OTHER INFORMATION: mecA 449-465 (+) Invader

<400> SEQUENCE: 44
ggatctgtac tgggttaatc agtattta                                          28

<210> SEQ ID NO 45
<211> LENGTH: 20
<212> TYPE: DNA
<213> ORGANISM: Artificial Sequence
<220> FEATURE:
<223> OTHER INFORMATION: mecA reverse amplification oligomer

<400> SEQUENCE: 45
ggtgttggtg aagatatacc                                                   20

<210> SEQ ID NO 46
<211> LENGTH: 24
<212> TYPE: DNA
<213> ORGANISM: Artificial Sequence
<220> FEATURE:
<223> OTHER INFORMATION: mecC Invader

<400> SEQUENCE: 46
atcactcggg atattttcac cgac                                              24

<210> SEQ ID NO 47
<211> LENGTH: 30
<212> TYPE: DNA
<213> ORGANISM: Artificial Sequence
<220> FEATURE:
<223> OTHER INFORMATION: mecC detection oligomer

<400> SEQUENCE: 47
acggacgcgg agttcccaaa tcttgcatac                                        30

<210> SEQ ID NO 48
<211> LENGTH: 26
<212> TYPE: DNA
<213> ORGANISM: Artificial Sequence
<220> FEATURE:
<223> OTHER INFORMATION: mecC reverse amplification oligomer

<400> SEQUENCE: 48
ttaaagcaag caatagaatc atcaga                                            26

<210> SEQ ID NO 49
<211> LENGTH: 21
<212> TYPE: DNA
<213> ORGANISM: Artificial Sequence
<220> FEATURE:
<223> OTHER INFORMATION: mecC reverse amplification oligomer

<400> SEQUENCE: 49
atggtaaggg ttggcaaaaa g                                                 21

<210> SEQ ID NO 50
<211> LENGTH: 20
<212> TYPE: DNA
<213> ORGANISM: Artificial Sequence
<220> FEATURE:
<223> OTHER INFORMATION: MREJ i Reverse amplification oligomer

<400> SEQUENCE: 50
gaaagactgc ggaggctaac                                                   20
```

```
<210> SEQ ID NO 51
<211> LENGTH: 22
<212> TYPE: DNA
<213> ORGANISM: Artificial Sequence
<220> FEATURE:
<223> OTHER INFORMATION: MREJ i Reverse amplification oligomer

<400> SEQUENCE: 51
gctaactatg tcaaaaatca tg                                              22

<210> SEQ ID NO 52
<211> LENGTH: 22
<212> TYPE: DNA
<213> ORGANISM: Artificial Sequence
<220> FEATURE:
<223> OTHER INFORMATION: MREJ i Reverse amplification oligomer

<400> SEQUENCE: 52
gactgcggag gctaactatg tc                                              22

<210> SEQ ID NO 53
<211> LENGTH: 19
<212> TYPE: DNA
<213> ORGANISM: Artificial Sequence
<220> FEATURE:
<223> OTHER INFORMATION: MREJ ii, viii, ix, xiv Reverse amplification
      oligomer

<400> SEQUENCE: 53
aagcggctga aataaccgc                                                  19

<210> SEQ ID NO 54
<211> LENGTH: 19
<212> TYPE: DNA
<213> ORGANISM: Artificial Sequence
<220> FEATURE:
<223> OTHER INFORMATION: MREJ ii, viii, ix, xiv Reverse amplification
      oligomer

<400> SEQUENCE: 54
aagcggctga aaaaccgc                                                   19

<210> SEQ ID NO 55
<211> LENGTH: 18
<212> TYPE: DNA
<213> ORGANISM: Artificial Sequence
<220> FEATURE:
<223> OTHER INFORMATION: MREJ ii Reverse amplification oligomer
<220> FEATURE:
<221> NAME/KEY: mod_base
<222> LOCATION: (1)..(18)
<223> OTHER INFORMATION: n = = 5'-methyl-2'deoxycytosine
<220> FEATURE:
<221> NAME/KEY: misc_feature
<222> LOCATION: (2)..(3)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t

<400> SEQUENCE: 55
cnntttatga agnggntg                                                   18

<210> SEQ ID NO 56
```

```
<211> LENGTH: 19
<212> TYPE: DNA
<213> ORGANISM: Artificial Sequence
<220> FEATURE:
<223> OTHER INFORMATION: MREJ v Reverse amplification oligomer

<400> SEQUENCE: 56
ttacggctga aataaccgc                                                   19

<210> SEQ ID NO 57
<211> LENGTH: 20
<212> TYPE: DNA
<213> ORGANISM: Artificial Sequence
<220> FEATURE:
<223> OTHER INFORMATION: MREJ xxi Reverse amplification oligomer

<400> SEQUENCE: 57
ctctcgcaaa acataacggc                                                  20

<210> SEQ ID NO 58
<211> LENGTH: 33
<212> TYPE: DNA
<213> ORGANISM: Artificial Sequence
<220> FEATURE:
<223> OTHER INFORMATION: orfX/SCCmec junction FRET Cassette
<220> FEATURE:
<221> NAME/KEY: misc_feature
<222> LOCATION: (1)..(1)
<223> OTHER INFORMATION: Fluorescein labeled
<220> FEATURE:
<221> NAME/KEY: misc_feature
<222> LOCATION: (4)..(4)
<223> OTHER INFORMATION: Blackberry Quencher 650 dT labeled
<220> FEATURE:
<221> NAME/KEY: misc_feature
<222> LOCATION: (33)..(33)
<223> OTHER INFORMATION: 3'-terminal Hexanediol

<400> SEQUENCE: 58
tctagccggt tttccggctg agacctcggc gcg                                   33

<210> SEQ ID NO 59
<211> LENGTH: 16
<212> TYPE: DNA
<213> ORGANISM: Artificial Sequence
<220> FEATURE:
<223> OTHER INFORMATION: orfX Forward amplification oligomer

<400> SEQUENCE: 59
cttccgaagg attggc                                                      16

<210> SEQ ID NO 60
<211> LENGTH: 23
<212> TYPE: DNA
<213> ORGANISM: Artificial Sequence
<220> FEATURE:
<223> OTHER INFORMATION: orfX Forward amplification oligomer

<400> SEQUENCE: 60
ccgaaggatt ggcccaagaa ttg                                              23

<210> SEQ ID NO 61
<211> LENGTH: 29
<212> TYPE: DNA
<213> ORGANISM: Artificial Sequence
<220> FEATURE:
<223> OTHER INFORMATION: orfX/SCCmec junction detection oligomer
<220> FEATURE:
<221> NAME/KEY: modified_base
```

```
<222> LOCATION: (12)..(12)
<223> OTHER INFORMATION: I
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (29)..(29)
<223> OTHER INFORMATION: 3'-terminal Hexanediol

<400> SEQUENCE: 61
cgcgccgagg cncaagaatt gaaccaacg                                     29

<210> SEQ ID NO 62
<211> LENGTH: 26
<212> TYPE: DNA
<213> ORGANISM: Artificial Sequence
<220> FEATURE:
<223> OTHER INFORMATION: orfX/SCCmec junction detection oligomer
<220> FEATURE:
<221> NAME/KEY: misc_feature
<222> LOCATION: (26)..(26)
<223> OTHER INFORMATION: 3'-terminal Hexanediol

<400> SEQUENCE: 62
cgcgccgagg gaaccaacgc atgacc                                        26

<210> SEQ ID NO 63
<211> LENGTH: 22
<212> TYPE: DNA
<213> ORGANISM: Artificial Sequence
<220> FEATURE:
<223> OTHER INFORMATION: MREJ iv Reverse amplification oligomer

<400> SEQUENCE: 63
ggatatggaa atccatctct ac                                            22

<210> SEQ ID NO 64
<211> LENGTH: 34
<212> TYPE: DNA
<213> ORGANISM: Artificial Sequence
<220> FEATURE:
<223> OTHER INFORMATION: MREJ iv Reverse amplification oligomer

<400> SEQUENCE: 64
cgctactaaa gaggatatgg aaatccatct ctac                               34

<210> SEQ ID NO 65
<211> LENGTH: 22
<212> TYPE: DNA
<213> ORGANISM: Artificial Sequence
<220> FEATURE:
<223> OTHER INFORMATION: MREJ iv Reverse amplification oligomer
<220> FEATURE:
<221> NAME/KEY: mod_base
<222> LOCATION: (1)..(2)
<223> OTHER INFORMATION: n = 5'-methyl-2'deoxycytosine
<220> FEATURE:
<221> NAME/KEY: misc_feature
<222> LOCATION: (2)..(3)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t
```

<400> SEQUENCE: 65
anngntanta aagaggatat gg                                              22

<210> SEQ ID NO 66
<211> LENGTH: 19
<212> TYPE: DNA
<213> ORGANISM: Artificial Sequence
<220> FEATURE:
<223> OTHER INFORMATION: MREJ v Reverse amplification oligomer
<220> FEATURE:
<221> NAME/KEY: mod_base
<222> LOCATION: (1)..(19)
<223> OTHER INFORMATION: n = 5'-methyl-2'deoxycytosine
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t

<400> SEQUENCE: 66
ttanggntga aataacngc                                                  19

<210> SEQ ID NO 67
<211> LENGTH: 28
<212> TYPE: DNA
<213> ORGANISM: Artificial Sequence
<220> FEATURE:
<223> OTHER INFORMATION: MREJ vi Reverse amplification oligomer

<400> SEQUENCE: 67
ctgattttca ctcttcatct acttactc                                        28

<210> SEQ ID NO 68
<211> LENGTH: 26
<212> TYPE: DNA
<213> ORGANISM: Artificial Sequence
<220> FEATURE:
<223> OTHER INFORMATION: MREJ vi Reverse amplification oligomer

<400> SEQUENCE: 68
gatataggtg tcacatcata tttcgc                                          26

<210> SEQ ID NO 69
<211> LENGTH: 32
<212> TYPE: DNA
<213> ORGANISM: Artificial Sequence
<220> FEATURE:
<223> OTHER INFORMATION: MREJ xiii Reverse amplification oligomer

<400> SEQUENCE: 69
ctctttcata gttcaattcc tcaagttgtt ga                                   32

<210> SEQ ID NO 70
<211> LENGTH: 25
<212> TYPE: DNA
<213> ORGANISM: Artificial Sequence
<220> FEATURE:
<223> OTHER INFORMATION: MREJ xiii Reverse amplification oligomer
<220> FEATURE:
<221> NAME/KEY: mod_base
<222> LOCATION: (1)..(25)
<223> OTHER INFORMATION: n = 5'-methyl-2'deoxycytosine

```
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t

<400> SEQUENCE: 70
gttgaagtan ttnattttnt aatgc                                     25

<210> SEQ ID NO 71
<211> LENGTH: 30
<212> TYPE: DNA
<213> ORGANISM: Artificial Sequence
<220> FEATURE:
<223> OTHER INFORMATION: MREJ xiii Reverse amplification oligomer

<400> SEQUENCE: 71
gccattcatt caccctaaac ttaatctttc                                30

<210> SEQ ID NO 72
<211> LENGTH: 19
<212> TYPE: DNA
<213> ORGANISM: Artificial Sequence
<220> FEATURE:
<223> OTHER INFORMATION: MREJ xiii Reverse amplification oligomer

<400> SEQUENCE: 72
ccattcattc accctaaac                                            19

<210> SEQ ID NO 73
<211> LENGTH: 20
<212> TYPE: DNA
<213> ORGANISM: Artificial Sequence
<220> FEATURE:
<223> OTHER INFORMATION: MREJ iii Reverse amplification oligomer

<400> SEQUENCE: 73
atacacaacc taattttag                                            20

<210> SEQ ID NO 74
<211> LENGTH: 24
<212> TYPE: DNA
<213> ORGANISM: Artificial Sequence
<220> FEATURE:
<223> OTHER INFORMATION: MREJ iii Reverse amplification oligomer

<400> SEQUENCE: 74
gtatgatatt gcaaggtata atcc                                      24

<210> SEQ ID NO 75
<211> LENGTH: 30
<212> TYPE: DNA
<213> ORGANISM: Artificial Sequence
<220> FEATURE:
<223> OTHER INFORMATION: MREJ iii Reverse amplification oligomer

<400> SEQUENCE: 75
cactctataa acatcgtatg atattgcaag                                30

<210> SEQ ID NO 76
```

```
<211> LENGTH: 30
<212> TYPE: DNA
<213> ORGANISM: Artificial Sequence
<220> FEATURE:
<223> OTHER INFORMATION: MREJ vii Reverse amplification oligomer

<400> SEQUENCE: 76
taatggaaat tcttaatctt tacttgtacc                                    30

<210> SEQ ID NO 77
<211> LENGTH: 26
<212> TYPE: DNA
<213> ORGANISM: Artificial Sequence
<220> FEATURE:
<223> OTHER INFORMATION: MREJ vii Reverse amplification oligomer
<220> FEATURE:
<221> NAME/KEY: mod_base
<222> LOCATION: (1)..(26)
<223> OTHER INFORMATION: n = 5'-methyl-2'deoxycytosine
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t

<400> SEQUENCE: 77
ggaaattntt aatntttant tgtanc                                        26

<210> SEQ ID NO 78
<211> LENGTH: 27
<212> TYPE: DNA
<213> ORGANISM: Artificial Sequence
<220> FEATURE:
<223> OTHER INFORMATION: MREJ vii Reverse amplification oligomer

<400> SEQUENCE: 78
caaaaagaag tcgatttaca caccatg                                       27

<210> SEQ ID NO 79
<211> LENGTH: 31
<212> TYPE: DNA
<213> ORGANISM: Artificial Sequence
<220> FEATURE:
<223> OTHER INFORMATION: MREJ vii Reverse amplification oligomer

<400> SEQUENCE: 79
ctttacatcg cttactgcaa acatctaata c                                  31

<210> SEQ ID NO 80
<211> LENGTH: 25
<212> TYPE: DNA
<213> ORGANISM: Artificial Sequence
<220> FEATURE:
<223> OTHER INFORMATION: MREJ xii Reverse amplification oligomer
<220> FEATURE:
<221> NAME/KEY: mod_base
<222> LOCATION: (1)..(25)
<223> OTHER INFORMATION: n = 5'-methyl-2'deoxycytosine
<220> FEATURE:
<221> NAME/KEY: misc_feature
```

```
<222> LOCATION: (7)..(7)
<223> OTHER INFORMATION: n is a, c, g, or t
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (18)..(20)
<223> OTHER INFORMATION: n is a, c, g, or t

<400> SEQUENCE: 80
aatgagnttt ttnnantnnn atttc                                          25

<210> SEQ ID NO 81
<211> LENGTH: 18
<212> TYPE: DNA
<213> ORGANISM: Artificial Sequence
<220> FEATURE:
<223> OTHER INFORMATION: MREJ xii Reverse amplification oligomer
<220> FEATURE:
<221> NAME/KEY: mod_base
<222> LOCATION: (1)..(18)
<223> OTHER INFORMATION: n = 5'-methyl-2'deoxycytosine
<220> FEATURE:
<221> NAME/KEY: misc_feature
<222> LOCATION: (2)..(3)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (7)..(9)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t

<400> SEQUENCE: 81
tnnantnnna tttnttnc                                                  18

<210> SEQ ID NO 82
<211> LENGTH: 22
<212> TYPE: DNA
<213> ORGANISM: Artificial Sequence
<220> FEATURE:
<223> OTHER INFORMATION: MREJ xii Reverse amplification oligomer

<400> SEQUENCE: 82
acttaatgag cttttccac tc                                              22

<210> SEQ ID NO 83
<211> LENGTH: 25
<212> TYPE: DNA
<213> ORGANISM: Artificial Sequence
<220> FEATURE:
<223> OTHER INFORMATION: MREJ xv Reverse amplification oligomer
<220> FEATURE:
<221> NAME/KEY: mod_base
<222> LOCATION: (1)..(25)
<223> OTHER INFORMATION: n = 5'-methyl-2'deoxycytosine
<220> FEATURE:
```

```
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (19)..(21)
<223> OTHER INFORMATION: n is a, c, g, or t

<400> SEQUENCE: 83
caatttntaa ggtagnttnn ntttc                                              25

<210> SEQ ID NO 84
<211> LENGTH: 25
<212> TYPE: DNA
<213> ORGANISM: Artificial Sequence
<220> FEATURE:
<223> OTHER INFORMATION: MREJ xv Reverse amplification oligomer

<400> SEQUENCE: 84
caatttctaa ggtagcttcc ctttc                                              25

<210> SEQ ID NO 85
<211> LENGTH: 12
<212> TYPE: DNA
<213> ORGANISM: Artificial Sequence
<220> FEATURE:
<223> OTHER INFORMATION: orfX/SCCmec junctiondetection oligomer core
      sequence

<400> SEQUENCE: 85
ccgagggaac ca                                                            12

<210> SEQ ID NO 86
<211> LENGTH: 12
<212> TYPE: DNA
<213> ORGANISM: Artificial Sequence
<220> FEATURE:
<223> OTHER INFORMATION: orfX/SCCmec junctiondetection oligomer core
      sequence
<220> FEATURE:
<221> NAME/KEY: mod_base
<222> LOCATION: (8)..(8)
<223> OTHER INFORMATION: I
<220> FEATURE:
<221> NAME/KEY: misc_feature
<222> LOCATION: (8)..(8)
<223> OTHER INFORMATION: n is a, c, g, or t

<400> SEQUENCE: 86
ccgaggcnca ag                                                            12

<210> SEQ ID NO 87
<211> LENGTH: 12
<212> TYPE: DNA
<213> ORGANISM: Artificial Sequence
<220> FEATURE:
<223> OTHER INFORMATION: mecA detection oligomer core sequence

<400> SEQUENCE: 87
cggacgtcga tt                                                            12

<210> SEQ ID NO 88
<211> LENGTH: 12
<212> TYPE: DNA
<213> ORGANISM: Artificial Sequence
```

```
<220> FEATURE:
<223> OTHER INFORMATION: mecA detection oligomer core sequence

<400> SEQUENCE: 88
caacctgttt ta                                                          12

<210> SEQ ID NO 89
<211> LENGTH: 12
<212> TYPE: DNA
<213> ORGANISM: Artificial Sequence
<220> FEATURE:
<223> OTHER INFORMATION: mecA detection oligomer core sequence

<400> SEQUENCE: 89
gcggagtcga tt                                                          12

<210> SEQ ID NO 90
<211> LENGTH: 12
<212> TYPE: DNA
<213> ORGANISM: Artificial Sequence
<220> FEATURE:
<223> OTHER INFORMATION: mecA detection oligomer core sequence

<400> SEQUENCE: 90
cggacgcgta ac                                                          12

<210> SEQ ID NO 91
<211> LENGTH: 12
<212> TYPE: DNA
<213> ORGANISM: Artificial Sequence
<220> FEATURE:
<223> OTHER INFORMATION: mecA detection oligomer core sequence

<400> SEQUENCE: 91
cggacgcacc tt                                                          12

<210> SEQ ID NO 92
<211> LENGTH: 12
<212> TYPE: DNA
<213> ORGANISM: Artificial Sequence
<220> FEATURE:
<223> OTHER INFORMATION: mecC detection oligomer core sequence

<400> SEQUENCE: 92
gcggagcatc ta                                                          12

<210> SEQ ID NO 93
<211> LENGTH: 12
<212> TYPE: DNA
<213> ORGANISM: Artificial Sequence
<220> FEATURE:
<223> OTHER INFORMATION: mecC detection oligomer core sequence

<400> SEQUENCE: 93
gcggagttcc ca                                                          12

<210> SEQ ID NO 94
<211> LENGTH: 12
<212> TYPE: DNA
<213> ORGANISM: Artificial Sequence
<220> FEATURE:
<223> OTHER INFORMATION: mecC detection oligomer core sequence

<400> SEQUENCE: 94
cggacgcatc ta                                                          12
```

```
<210> SEQ ID NO 95
<211> LENGTH: 12
<212> TYPE: DNA
<213> ORGANISM: Artificial Sequence
<220> FEATURE:
<223> OTHER INFORMATION: GAPDH detection oligomer core sequence

<400> SEQUENCE: 95
gcggaggtga ac                                                            12

<210> SEQ ID NO 96
<211> LENGTH: 12
<212> TYPE: DNA
<213> ORGANISM: Artificial Sequence
<220> FEATURE:
<223> OTHER INFORMATION: GAPDH detection oligomer core sequence

<400> SEQUENCE: 96
gcggagagtt ga                                                            12

<210> SEQ ID NO 97
<211> LENGTH: 16
<212> TYPE: DNA
<213> ORGANISM: Artificial Sequence
<220> FEATURE:
<223> OTHER INFORMATION: orfX/SCCmec junctiondetection oligomer
      target-hybridizing sequence

<400> SEQUENCE: 97
gaaccaacgc atgacc                                                        16

<210> SEQ ID NO 98
<211> LENGTH: 19
<212> TYPE: DNA
<213> ORGANISM: Artificial Sequence
<220> FEATURE:
<223> OTHER INFORMATION: orfX/SCCmec junctiondetection oligomer
      target-hybridizing sequence
<220> FEATURE:
<221> NAME/KEY: mod_base
<222> LOCATION: (2)..(2)
<223> OTHER INFORMATION: I
<220> FEATURE:
<221> NAME/KEY: misc_feature
<222> LOCATION: (2)..(2)
<223> OTHER INFORMATION: n is a, c, g, or t

<400> SEQUENCE: 98
cncaagaatt gaaccaacg                                                     19

<210> SEQ ID NO 99
<211> LENGTH: 26
<212> TYPE: DNA
<213> ORGANISM: Artificial Sequence
<220> FEATURE:
<223> OTHER INFORMATION: mecA detection oligomer target-hybridizing
      sequence

<400> SEQUENCE: 99
tcgattttat aacttgtttt atcgtc                                             26

<210> SEQ ID NO 100
<211> LENGTH: 26
<212> TYPE: DNA
<213> ORGANISM: Artificial Sequence
<220> FEATURE:
<223> OTHER INFORMATION: mecA detection oligomer target-hybridizing
      sequence
```

```
<400> SEQUENCE: 100
tcgattttat aacttgtttt atcgtc                                        26

<210> SEQ ID NO 101
<211> LENGTH: 28
<212> TYPE: DNA
<213> ORGANISM: Artificial Sequence
<220> FEATURE:
<223> OTHER INFORMATION: mecA detection oligomer target-hybridizing
      sequence

<400> SEQUENCE: 101
gttttaagtc gatattacca tttaccac                                      28

<210> SEQ ID NO 102
<211> LENGTH: 17
<212> TYPE: DNA
<213> ORGANISM: Artificial Sequence
<220> FEATURE:
<223> OTHER INFORMATION: mecA detection oligomer target-hybridizing
      sequence

<400> SEQUENCE: 102
cgtaacctga atcagct                                                  17

<210> SEQ ID NO 103
<211> LENGTH: 16
<212> TYPE: DNA
<213> ORGANISM: Artificial Sequence
<220> FEATURE:
<223> OTHER INFORMATION: mecA detection oligomer target-hybridizing
      sequence

<400> SEQUENCE: 103
caccttgtcc gtaacc                                                   16

<210> SEQ ID NO 104
<211> LENGTH: 31
<212> TYPE: DNA
<213> ORGANISM: Artificial Sequence
<220> FEATURE:
<223> OTHER INFORMATION: mecC detection oligomer target-hybridizing
      sequence

<400> SEQUENCE: 104
catctattat agccttaaaa gaaaataaac t                                  31

<210> SEQ ID NO 105
<211> LENGTH: 31
<212> TYPE: DNA
<213> ORGANISM: Artificial Sequence
<220> FEATURE:
<223> OTHER INFORMATION: mecC detection oligomer target-hybridizing
      sequence

<400> SEQUENCE: 105
catctattat agccttaaaa gaaaataaac t                                  31

<210> SEQ ID NO 106
<211> LENGTH: 18
<212> TYPE: DNA
<213> ORGANISM: Artificial Sequence
<220> FEATURE:
<223> OTHER INFORMATION: mecC detection oligomer target-hybridizing
      sequence
```

```
<400> SEQUENCE: 106
ttcccaaatc ttgcatac                                                18

<210> SEQ ID NO 107
<211> LENGTH: 18
<212> TYPE: DNA
<213> ORGANISM: Artificial Sequence
<220> FEATURE:
<223> OTHER INFORMATION: GAPDH detection oligomer target-hybridizing
      sequence

<400> SEQUENCE: 107
gtgaaccaga tgcaagca                                                18

<210> SEQ ID NO 108
<211> LENGTH: 18
<212> TYPE: DNA
<213> ORGANISM: Artificial Sequence
<220> FEATURE:
<223> OTHER INFORMATION: GAPDH detection oligomer target-hybridizing
      sequence

<400> SEQUENCE: 108
agttgatggt ggtttccg                                                18

<210> SEQ ID NO 109
<211> LENGTH: 23
<212> TYPE: DNA
<213> ORGANISM: Artificial Sequence
<220> FEATURE:
<223> OTHER INFORMATION: mecC forward amplification oligomer

<400> SEQUENCE: 109 atcttttttgc caacccttac cat                                         23

<210> SEQ ID NO 110
<211> LENGTH: 29
<212> TYPE: DNA
<213> ORGANISM: Artificial Sequence
<220> FEATURE:
<223> OTHER INFORMATION: mecC reverse amplification oligomer

<400> SEQUENCE: 110
tcaccaggtt caacccaaaa aatattaac                                    29

<210> SEQ ID NO 111
<211> LENGTH: 28
<212> TYPE: DNA
<213> ORGANISM: Artificial Sequence
<220> FEATURE:
<223> OTHER INFORMATION: orfX/SCCmec junctiondetection oligomer

<400> SEQUENCE: 111
acggacgcgg aggaaccaac gcatgacc                                     28

<210> SEQ ID NO 112
<211> LENGTH: 36
<212> TYPE: DNA
<213> ORGANISM: Artificial Sequence
<220> FEATURE:
<223> OTHER INFORMATION: mecA detection oligomer

<400> SEQUENCE: 112
cgcgccgagg tcgattttat aacttgttttt atcgtc                           36
```

```
<210> SEQ ID NO 113
<211> LENGTH: 41
<212> TYPE: DNA
<213> ORGANISM: Artificial Sequence
<220> FEATURE:
<223> OTHER INFORMATION: mecC detection oligomer

<400> SEQUENCE: 113
cgcgccgagg catctattat agccttaaaa gaaaataaac t               41

<210> SEQ ID NO 114
<211> LENGTH: 30
<212> TYPE: DNA
<213> ORGANISM: Artificial Sequence
<220> FEATURE:
<223> OTHER INFORMATION: GAPDH detection oligomer

<400> SEQUENCE: 114
aggccacgga cggtgaacca gatgcaagca                             30

<210> SEQ ID NO 115
<211> LENGTH: 28
<212> TYPE: DNA
<213> ORGANISM: Artificial Sequence
<220> FEATURE:
<223> OTHER INFORMATION: orfX/SCCmec junctiondetection oligomer

<400> SEQUENCE: 115
aggccacgga cggaaccaac gcatgacc                               28

<210> SEQ ID NO 116
<211> LENGTH: 38
<212> TYPE: DNA
<213> ORGANISM: Artificial Sequence
<220> FEATURE:
<223> OTHER INFORMATION: mecA detection oligomer

<400> SEQUENCE: 116
acggacgcgg agtcgatttt ataacttgtt ttatcgtc                    38

<210> SEQ ID NO 117
<211> LENGTH: 43
<212> TYPE: DNA
<213> ORGANISM: Artificial Sequence
<220> FEATURE:
<223> OTHER INFORMATION: mecC detection oligomer

<400> SEQUENCE: 117
acggacgcgg agcatctatt atagccttaa aagaaaataa act              43

<210> SEQ ID NO 118
<211> LENGTH: 28
<212> TYPE: DNA
<213> ORGANISM: Artificial Sequence
<220> FEATURE:
<223> OTHER INFORMATION: GAPDH detection oligomer

<400> SEQUENCE: 118
cgcgccgagg gtgaaccaga tgcaagca                               28

<210> SEQ ID NO 119
<211> LENGTH: 12
<212> TYPE: DNA
<213> ORGANISM: Artificial Sequence
<220> FEATURE:
<223> OTHER INFORMATION: orfX/SCCmec junctiondetection oligomer core
      sequence
```

```
<400> SEQUENCE: 119
gcggaggaac ca                                                          12

<210> SEQ ID NO 120
<211> LENGTH: 12
<212> TYPE: DNA
<213> ORGANISM: Artificial Sequence
<220> FEATURE:
<223> OTHER INFORMATION: mecA detection oligomer core sequence

<400> SEQUENCE: 120
ccgaggtcga tt                                                          12

<210> SEQ ID NO 121
<211> LENGTH: 12
<212> TYPE: DNA
<213> ORGANISM: Artificial Sequence
<220> FEATURE:
<223> OTHER INFORMATION: mecC detection oligomer core sequence

<400> SEQUENCE: 121
ccgaggcatc ta                                                          12

<210> SEQ ID NO 122
<211> LENGTH: 12
<212> TYPE: DNA
<213> ORGANISM: Artificial Sequence
<220> FEATURE:
<223> OTHER INFORMATION: GAPDH detection oligomer core sequence

<400> SEQUENCE: 122
cggacggtga ac                                                          12

<210> SEQ ID NO 123
<211> LENGTH: 12
<212> TYPE: DNA
<213> ORGANISM: Artificial Sequence
<220> FEATURE:
<223> OTHER INFORMATION: orfX/SCCmec junctiondetection oligomer core
      sequence

<400> SEQUENCE: 123
cggacggaac ca                                                          12

<210> SEQ ID NO 124
<211> LENGTH: 12
<212> TYPE: DNA
<213> ORGANISM: Artificial Sequence
<220> FEATURE:
<223> OTHER INFORMATION: mecA detection oligomer core sequence

<400> SEQUENCE: 124
gcggagtcga tt                                                          12

<210> SEQ ID NO 125
<211> LENGTH: 12
<212> TYPE: DNA
<213> ORGANISM: Artificial Sequence
<220> FEATURE:
<223> OTHER INFORMATION: mecC detection oligomer core sequence

<400> SEQUENCE: 125
gcggagcatc ta                                                          12
```

```
<210> SEQ ID NO 126
<211> LENGTH: 12
<212> TYPE: DNA
<213> ORGANISM: Artificial Sequence
<220> FEATURE:
<223> OTHER INFORMATION: GAPDH detection oligomer core sequence

<400> SEQUENCE: 126
ccgagggtga ac                                                              12
```

COMPOSITIONS AND METHODS FOR DETECTING *STAPHYLOCOCCUS AUREUS*

CROSS-REFERENCE TO RELATED APPLICATIONS

This application is a national stage entry under 35 U.S.C. § 371 of International Patent Application No. PCT/US2018/045975, which claims the benefit under 35 U.S.C. § 119(e) of U.S. Provisional Application No. 62/544,491, filed Aug. 11, 2017, the disclosures of each of which are hereby incorporated by reference.

SEQUENCE LISTING

The present application is filed with a Sequence Listing in electronic format. The Sequence Listing is provided as a file entitled "2018-08-06_01159-0014-00PCT_Seq_List_ST25.txt" created on Aug. 6, 2018, which is 59,211 bytes in size. The information in the electronic format of the sequence listing is incorporated herein by reference in its entirety.

The embodiments herein are directed to the field of detecting infectious agents, more specifically by using compositions and methods to detect *Staphylococcus* bacteria including methicillin-resistant *Staphylococcus aureus* (MRSA), such as one or more of MRSA comprising a type i, ii, iii, iv, v, vi, vii, viii, ix, xii, xiii, xiv, xv, or xxi SCCmec right extremity junction (MREJ).

*Staphylococcus aureus* is a coagulase-positive opportunistic pathogen responsible for nosocomial infections including of the skin and post-operative wounds, food poisoning, and toxic shock syndrome. It is also known to cause bacteremia, pneumonia, abscesses, osteomyelitis, and infections of the heart (endocarditis, myocarditis, and pericarditis) and central nervous system (cerebritis and meningitis). It can spread easily in hospital settings, including through surface contact.

MRSA is multidrug-resistant and often requires treatment with more costly and/or toxic antibiotics considered the last line of defense, unlike methicillin-sensitive *S. aureus* (MSSA or SA). MRSA carries a mecA or mecC gene, which encode a β-lactam-resistant penicillin-binding protein that confers resistance to β-lactam antibiotics including but not limited to methicillin and penicillin. The mecC gene is also known as $mecA_{LGA251}$. The mecA or mecC gene is located within a mobile genetic element termed SCCmec which also generally contains terminal inverted and direct repeats and a set of site-specific recombinase genes (ccrA, ccrB, and ccrC) that can catalyze the integration of SCCmec into the orfX gene on the *S. aureus* chromosome, thereby transforming MSSA into MRSA (Ito et al., 1999, Antimicrob. Agents Chemother. 43:1449-1458; Katayama et al., 2000, Antimicrob. Agents Chemother. 44:1549-1555; Huletsky et al., US Patent Pub. No. 2008/0227087).

Rapid identification of MRSA is important to facilitate appropriate responses to both treat infected subjects and contain and limit its spread, including antibiotic therapy and other infection control measures such as isolation, disinfection, etc. Thus, compositions and methods for rapid nucleic acid-based detection of MRSA are desirable.

Nucleic acid-based detection of MRSA is, however, complicated by several factors. Other *Staphylococcus* species including coagulase-negative staphylococci (CNS) (e.g., *S. epidermidis*, part of normal human skin flora) can carry a mec gene, so detection of mecA or mecC alone is insufficient to identify MRSA. Indeed, the US Food and Drug Administration has recommended distinguishing other *Staphylococcus* species from MRSA. See "Establishing the Performance Characteristics of Nucleic Acid-Based In vitro Diagnostic Devices for the Detection and Differentiation of Methicillin-Resistant *Staphylococcus aureus* (MRSA) and *Staphylococcus aureus* (SA)," FDA Draft Guidance, Jan. 5, 2011, at pp. 22-23, available from the FDA website at /downloads/MedicalDevices/DeviceRegulationandGuidance/GuidanceDocuments/UCM2388 51.pdf. Detection of an SCCmec sequence alone is also insufficient in that not all SCCmec elements carry mecA or mecC due to an empty cassette or drop-out phenomenon—that is, some MSSA strains appear SCCmec-positive and may register as false positives in MRSA assays that do not detect mecA or mecC gene sequences per se. See, e.g., Rupp et al., *J. Clin. Microbiol.* 44:2317 (2006). And SCCmec itself is highly polymorphic, with at least 21 MREJ types having been described (see US Patent Pub. No. 2013/0266942).

Accordingly, there is a need for compositions and methods that can provide rapid and accurate identification of one or more of the various types of MRSA and/or discriminate them from MSSA, including empty-cassette SCCmec positive MSSA, and/or methicillin-resistant CNS. This disclosure aims to meet these needs, provide other benefits, or at least provide the public with a useful choice.

Provided herein are the following embodiments. Embodiment 1 is a composition or kit comprising at least one orfX amplification oligomer, at least a first SCCmec right extremity junction (MREJ) amplification oligomer, and a plurality of mec amplification oligomers, wherein: the orfX amplification oligomer is configured to specifically hybridize to a site comprising at least one of positions 186 or 192 of SEQ ID NO: 16; the MREJ amplification oligomer is configured to specifically hybridize to an SCCmec sequence; the orfX amplification oligomer and the MREJ amplification oligomer are configured to produce an orfX/SCCmec junction amplicon of a length ranging from about 200 nucleotides to about 2000 nucleotides; the plurality of mec amplification oligomers comprises first and second mecA/mecC amplification oligomers; the first mecA/mecC amplification oligomer is configured to specifically hybridize to a site comprising: position 1394 of SEQ ID NO: 13 and position 1285 of SEQ ID NO: 14, or position 1484 of SEQ ID NO: 13 and position 1376 of SEQ ID NO: 14; the second mecA/mecC amplification oligomer is configured to specifically hybridize to a site comprising position 1312 of SEQ ID NO: 13 and position 1203 of SEQ ID NO: 14; and the first and second mecA/mecC amplification oligomers are configured to produce a mec amplicon.

Embodiment 2 is a composition or kit comprising at least one orfX amplification oligomer, at least a first MREJ amplification oligomer, and at least first and second GAPDH amplification oligomers, wherein: the orfX amplification oligomer is configured to specifically hybridize to a site comprising at least one of positions 186 or 192 of SEQ ID NO: 16; the MREJ amplification oligomer is configured to specifically hybridize to an SCCmec sequence; the orfX amplification oligomer and the MREJ amplification oligomer are configured to produce an orfX/SCCmec junction amplicon of a length ranging from about 200 nucleotides to about 2000 nucleotides; the first GAPDH amplification oligomer is configured to specifically hybridize to a site comprising position 169 or 212 of SEQ ID NO: 15; the second GAPDH amplification oligomer is configured to specifically hybridize to a site comprising position 279, 312, or 421 of SEQ ID NO: 15; and the first and second GAPDH amplification oligomers are configured to produce a GAPDH amplicon.

Embodiment 3 is a method of detecting MRSA nucleic acid comprising: preparing a composition according to embodiment 1 or embodiment 2, wherein the composition further comprises a sample comprising or suspected of comprising MRSA nucleic acid; subjecting the composition to amplification conditions; and detecting the presence or absence of the orfX/SCCmec junction amplicon and at least one of the mec amplicon and the GAPDH amplicon.

Embodiment 4 is a composition or kit comprising: an orfX amplification oligomer configured to specifically hybridize to a site comprising at least one of positions 186 or 192 of SEQ ID NO: 16; at least one detection oligomer comprising a target-hybridizing sequence configured to hybridize specifically to a site comprising position 201 or 210 of SEQ ID NO: 16; and at least first and second MREJ amplification oligomers, wherein: the orfX amplification oligomer and the first MREJ amplification oligomer are configured to produce a first orfX/SCCmec junction amplicon of a length ranging from about 200 nucleotides to about 2000 nucleotides from a MRSA of one or more first MREJ types; and the orfX amplification oligomer and the second MREJ amplification oligomer are configured to produce a second orfX/SCCmec junction amplicon of a length ranging from about 200 nucleotides to about 2000 nucleotides from a MRSA of one or more second MREJ types different from the one or more first MREJ types.

Embodiment 5 is the composition, kit, or method of anyone of the preceding embodiments, wherein the MREJ amplification oligomer is configured to hybridize specifically to an SCCmec sequence of at least one of MREJ types i, ii, iii, iv, v, vi, vii, viii, ix, xii, xiii, xiv, xv, or xxi.

Embodiment 6 is a composition or kit comprising: an orfX amplification oligomer configured to specifically hybridize to a site comprising at least one of positions 186 or 192 of SEQ ID NO: 16; and at least a first MREJ amplification oligomer, wherein the first MREJ amplification oligomer is configured to specifically hybridize to a site comprising position 491 of SEQ ID NO: 17 and position 555 of SEQ ID NO: 18, wherein: the orfX amplification oligomer and the first MREJ amplification oligomer are configured to produce a first orfX/SCCmec junction amplicon from a MRSA of MREJ type xv.

Embodiment 7 is the composition, kit, or method of anyone of the preceding embodiments, wherein the composition or kit further comprises at least second and third MREJ amplification oligomers each configured to hybridize specifically to at least one of an SCCmec sequence of at least one of MREJ types i, ii, iii, iv, v, vi, vii, viii, ix, xii, xiii, xiv, xv, or xxi which are different from each other and from the MREJ type(s) to which the first MREJ amplification oligomer is configured to specifically hybridize and to produce orfX/SCCmec junction amplicons of lengths ranging from about 50 nucleotides to about 2000 nucleotides.

Embodiment 8 is the composition, kit, or method of anyone of the preceding embodiments, wherein the composition or kit further comprises a plurality of MREJ amplification oligomers configured to hybridize specifically to at least one of an SCCmec sequence of at least one of MREJ types i, ii, iii, iv, v, vi, vii, viii, ix, xii, xiii, xiv, xv, or xxi, wherein the at least one orfX primer and the MREJ amplification oligomers of the kit or composition collectively are configured to produce orfX/SCCmec junction amplicons from at least 7, 8, 9, 10, 11, 12, 13, or 14 of MREJ types i, ii, iii, iv, v, vi, vii, viii, ix, xii, xiii, xiv, xv, or xxi, wherein the orfX/SCCmec junction amplicons are of lengths ranging from about 200 nucleotides to about 2000 nucleotides.

Embodiment 9 is a method of detecting MRSA nucleic acid comprising: preparing a composition according to any one of embodiments 4 to 8, wherein the composition further comprises a sample comprising or suspected of comprising MRSA nucleic acid; subjecting the composition to amplification conditions; and detecting the presence or absence of at least one orfX/SCCmec junction amplicon using the at least one detection oligomer.

Embodiment 10 is the composition, kit, or method of anyone of the preceding embodiments, wherein the kit or composition comprises at least one MREJ amplification oligomer configured to specifically hybridize to an MREJ type i nucleic acid at a site comprising at least one of positions 277, 287, or 293 of SEQ ID NO: 1. Embodiment 11 is the composition, kit, or method of any one of the preceding embodiments, wherein the kit or composition comprises at least one MREJ amplification oligomer configured to specifically hybridize to an MREJ type ii nucleic acid at a site comprising at least one of positions 613, 622, 721, 731, or 737 of SEQ ID NO: 2. Embodiment 12 is the composition, kit, or method of any one of the preceding embodiments, wherein the kit or composition comprises at least one MREJ amplification oligomer configured to specifically hybridize to an MREJ type ix nucleic acid at a site comprising position 473 or 654 of SEQ ID NO: 8. Embodiment 13 is the composition, kit, or method of any one of the preceding embodiments, wherein the kit or composition comprises at least one MREJ amplification oligomer configured to specifically hybridize to an MREJ type xiv nucleic acid at a site comprising position 482, 584, or 765 of SEQ ID NO: 11. Embodiment 14 is the composition, kit, or method of any one of the preceding embodiments, wherein the kit or composition comprises at least one MREJ amplification oligomer configured to specifically hybridize to at least one of MREJ types i, ii, viii, ix, and xiv, and comprising the sequence of one of SEQ ID NOs: 50-55 or 69-72, with up to two mismatches. Embodiment 15 is the composition, kit, or method of any one of the preceding embodiments, wherein the kit or composition comprises at least one MREJ amplification oligomer comprising the sequence of one of SEQ ID NOs: 52, 53, or 55. Embodiment 16 is the composition, kit, or method of any one of the preceding embodiments, wherein the kit or composition comprises at least one MREJ amplification oligomer comprising the sequence of SEQ ID NO: 50. Embodiment 17 is the composition, kit, or method of any one of the preceding embodiments, wherein the kit or composition comprises at least one MREJ amplification oligomer comprising the sequence of SEQ ID NO: 51. Embodiment 18 is the composition, kit, or method of any one of the preceding embodiments, wherein the kit or composition comprises at least one MREJ amplification oligomer comprising the sequence of SEQ ID NO: 53 or 54. Embodiment 19 is the composition, kit, or method of any one of the preceding embodiments, wherein the kit or composition comprises at least one MREJ amplification oligomer comprising the sequence of SEQ ID NO: 69-72. Embodiment 20 is the composition, kit, or method of any one of the preceding embodiments, wherein the kit or composition comprises at least one MREJ amplification oligomer configured to specifically hybridize to an MREJ type iii nucleic acid at a site comprising at least one of positions 668, 738, or 750 of SEQ ID NO: 3. Embodiment 21 is the composition, kit, or method of any one of the preceding embodiments, wherein the kit or composition comprises at least one MREJ amplification oligomer configured to specifically hybridize to an MREJ type iii nucleic acid and comprising the sequence of one of SEQ ID NOs: 73-75, with up to two mismatches. Embodiment 22 is the composition, kit, or method of any one of the preceding embodiments, wherein the kit or composition comprises at least one MREJ amplification oligomer comprising the sequence of one of SEQ ID NOs: 73-75.

Embodiment 23 is the composition, kit, or method of anyone of the preceding embodiments, wherein the kit or composition comprises an MREJ amplification oligomer configured to specifically hybridize to an MREJ type iv nucleic acid at a site comprising at least one of positions 545, 551, or 559 of SEQ ID NO: 4. Embodiment 24 is the composition, kit, or method of any one of the preceding embodiments, wherein the kit or composition comprises at least one MREJ amplification oligomer configured to specifically hybridize to an MREJ type iv nucleic acid and comprising the sequence of one of SEQ ID NOs: 63-65, with up to two mismatches. Embodiment 25 is the composition, kit, or method of any one of the preceding embodiments, wherein the kit or composition comprises at least one MREJ amplification oligomer comprising the sequence of one of SEQ ID NOs: 63-65. Embodiment 26 is the composition, kit, or method of any one of the preceding embodiments, wherein the kit or composition comprises an MREJ amplification oligomer configured to specifically hybridize to an MREJ type v nucleic acid at a site comprising position 458 of SEQ ID NO: 5. Embodiment 27 is the composition, kit, or method of any one of the preceding embodiments, wherein the kit or composition comprises at least one MREJ amplification oligomer configured to specifically hybridize to an MREJ type v nucleic acid and comprising the sequence of SEQ ID NO: 56, with up to two mismatches. Embodiment 28 is the composition, kit, or method of any one of the preceding embodiments, wherein the kit or composition comprises at least one MREJ amplification oligomer comprising the sequence of SEQ ID NO: 56.

Embodiment 29 is the composition, kit, or method of any one of the preceding embodiments, wherein the kit or composition comprises an MREJ amplification oligomer configured to specifically hybridize to an MREJ type vi nucleic acid at a site comprising position 498 or 611 of SEQ ID NO: 6. Embodiment 30 is the composition, kit, or method of any one of the preceding embodiments, wherein the kit or composition comprises at least one MREJ amplification oligomer configured to specifically hybridize to an MREJ type vi nucleic acid and comprising the sequence of one of SEQ ID NOs: 67-68, with up to two mismatches. Embodiment 31 is the composition, kit, or method of any one of the preceding embodiments, wherein the kit or composition comprises at least one MREJ amplification oligomer comprising the sequence of one of SEQ ID NOs: 67-68.

Embodiment 32 is the composition, kit, or method of anyone of the preceding embodiments, wherein the kit or composition comprises an MREJ amplification oligomer configured to specifically hybridize to an MREJ type vii nucleic acid at a site comprising at least one of positions 563, 565, 601, or 629 of SEQ ID NO: 7. Embodiment 33 is the composition, kit, or method of any one of the preceding embodiments, wherein the kit or composition comprises at least one MREJ amplification oligomer configured to specifically hybridize to an MREJ type vii nucleic acid and comprising the sequence of one of SEQ ID NOs: 76-79, with up to two mismatches. Embodiment 34 is the composition, kit, or method of any one of the preceding embodiments, wherein the kit or composition comprises at least one MREJ amplification oligomer comprising the sequence of one of SEQ ID NOs: 76-79.

Embodiment 35 is the composition, kit, or method of any one of the preceding embodiments, wherein the kit or composition comprises wherein an MREJ amplification oligomer configured to specifically hybridize to an MREJ type xii nucleic acid at a site comprising at least one of positions 617, 624, or 630 of SEQ ID NO: 9. Embodiment 36 is the composition, kit, or method of any one of the preceding embodiments, wherein the kit or composition comprises at least one MREJ amplification oligomer configured to specifically hybridize to an MREJ type xii nucleic acid and comprising the sequence of one of SEQ ID NOs: 80-82, with up to two mismatches. Embodiment 37 is the composition, kit, or method of any one of the preceding embodiments, wherein the kit or composition comprises at least one MREJ amplification oligomer comprising the sequence of one of SEQ ID NOs: 80-82.

Embodiment 38 is the composition, kit, or method of any one of the preceding embodiments, wherein the kit or composition comprises wherein an MREJ amplification oligomer is configured to specifically hybridize to an MREJ type xiii nucleic acid at a site comprising at least one of positions 561, 568, 605, or 628 of SEQ ID NO: 10. Embodiment 39 is the composition, kit, or method of any one of the preceding embodiments, wherein the kit or composition comprises at least one MREJ amplification oligomer configured to specifically hybridize to an MREJ type xiii nucleic acid and comprising the sequence of one of SEQ ID NOs: 69-72, with up to two mismatches. Embodiment 40 is the composition, kit, or method of any one of the preceding embodiments, wherein the kit or composition comprises at least one MREJ amplification oligomer comprising the sequence of one of SEQ ID NOs: 69-72.

Embodiment 41 is the composition, kit, or method of any one of the preceding embodiments, wherein the kit or composition comprises at least one MREJ amplification oligomer configured to specifically hybridize to an MREJ type xxi nucleic acid at a site comprising position 461 of SEQ ID NO: 12. Embodiment 42 is the composition, kit, or method of any one of the preceding embodiments, wherein the kit or composition comprises at least one MREJ amplification oligomer configured to specifically hybridize to an MREJ type xxi nucleic acid and comprising the sequence of SEQ ID NO: 57, with up to two mismatches. Embodiment 43 is the composition, kit, or method of any one of the preceding embodiments, wherein the kit or composition comprises at least one MREJ amplification oligomer comprising the sequence of SEQ ID NO: 57.

Embodiment 44 is the composition, kit, or method of any one of the preceding embodiments, wherein the orfX amplification oligomer competes for hybridization to an orfX nucleic acid under stringent conditions with an oligomer having a sequence consisting of SEQ ID NO: 59. Embodiment 45 is the composition, kit, or method of any one of the preceding embodiments, wherein the orfX amplification oligomer competes for hybridization to an orfX nucleic acid under stringent conditions with an oligomer having a sequence consisting of SEQ ID NO: 60. Embodiment 46 is the composition, kit, or method of any one of the preceding embodiments, wherein the orfX amplification oligomer is configured to specifically hybridize to a site comprising position 186 of SEQ ID NO: 16. Embodiment 47 is the composition, kit, or method of any one of the preceding embodiments, wherein the orfX amplification oligomer is configured to specifically hybridize to a site comprising position 192 of SEQ ID NO: 16. Embodiment 48 is the composition, kit, or method of any one of the preceding embodiments, wherein the orfX amplification oligomer comprises the sequence of SEQ ID NO: 59 with up to two mismatches. Embodiment 49 is the composition, kit, or method of any one of the preceding embodiments, wherein the orfX amplification oligomer comprises the sequence of SEQ ID NO: 59. Embodiment 50 is the composition, kit, or method of any one of embodiments 1-47, wherein the orfX amplification oligomer comprises the sequence of SEQ ID NO: 60 with up to two mismatches. Embodiment 51 is the composition, kit, or method of any one of embodiments 1-47, wherein the orfX amplification oligomer comprises the sequence of SEQ ID NO: 60.

Embodiment 52 is the composition, kit, or method of any one of the preceding embodiments, wherein the composition or kit further comprises at least one primary orfX/SCCmec junction detection oligomer configured to hybridize specifically to the orfX/SCCmec junction amplicon sequence. Embodiment 53 is the composition, kit, or method of embodiment 52, wherein the orfX/SCCmec junction primary detection oligomer is non-extendable.

Embodiment 54 is the composition, kit, or method of embodiment 52 or 53, wherein the orfX/SCCmec junction primary detection oligomer comprises a label. Embodiment 55 is the composition, kit, or method of any one of embodiments 52-54, wherein the orfX/SCCmec junction primary detection oligomer is configured to hybridize specifically to a site comprising at least one of positions 201 and 211 of SEQ ID NO: 16. Embodiment 56 is the composition, kit, or method of any one of embodiments 52-55, wherein the orfX/SCCmec junction primary detection oligomer is configured to hybridize specifically to a site overlapping the site in SEQ ID NO: 16 to which the orfX amplification oligomer is configured to specifically hybridize. Embodiment 57 is the composition, kit, or method of any one of embodiments 52-56, wherein the orfX/SCCmec junction primary detection oligomer competes for hybridization to SEQ ID NO: 16 under stringent conditions with a detection oligomer having a sequence consisting of SEQ ID NO: 61 or 62. Embodiment 58 is the composition, kit, or method of any one of embodiments 52-57, wherein the orfX/SCCmec junction primary detection oligomer comprises the sequence of at least one of SEQ ID NO: 85, 86, 97, or 98. Embodiment 59 is the composition, kit, or method of any one of embodiments 52-58, wherein the orfX/SCCmec junction primary detection oligomer comprises the sequence of SEQ ID NO: 61, 62, 111, or 115 with up to two mismatches. Embodiment 60 is the composition, kit, or method of any one of embodiments 52-59, wherein the orfX/SCCmec junction primary detection oligomer comprises the sequence of SEQ ID NO: 61, 62, 111, or 115.

Embodiment 61 is the composition, kit, or method of any one of the preceding embodiments, wherein the first MREJ amplification oligomer competes for hybridization to an MREJ type xv nucleic acid under stringent conditions with an oligomer having a sequence consisting of SEQ ID NO: 83 including cytosine methylation or SEQ ID NO: 84. Embodiment 62 is the composition, kit, or method of any one of the preceding embodiments, wherein the first MREJ amplification oligomer comprises the sequence of SEQ ID NO: 83 including cytosine methylation with up to two mismatches. Embodiment 63 is the composition, kit, or method of any one of the preceding embodiments, wherein the first MREJ amplification oligomer comprises the sequence of SEQ ID NO: 83 including cytosine methylation.

Embodiment 64 is the composition, kit, or method of any one of embodiments 1-61, wherein the first MREJ amplification oligomer comprises the sequence of SEQ ID NO: 84 with up to two mismatches. Embodiment 65 is the composition, kit, or method of embodiment 64, wherein the first MREJ amplification oligomer comprises the sequence of SEQ ID NO: 84.

Embodiment 66 is the composition, kit, or method of any one of embodiments 2-65, wherein the composition or kit comprises a plurality of mec amplification oligomers configured to produce at least one of a mecA amplicon or a mecC amplicon. Embodiment 67 is the composition, kit, or method of embodiment 1 or 66, wherein the plurality of mec amplification oligomers comprises a mec amplification oligomer that competes for hybridization under stringent conditions for binding to a mecA nucleic acid with an oligomer having a sequence consisting of SEQ ID NO: 30, 34, 36, 37, 39, or 40. Embodiment 68 is the composition, kit, or method of embodiment 1, 66, or 67, wherein the plurality of mec amplification oligomers comprises a mec amplification oligomer that comprises the sequence of SEQ ID NO: 30, 34, 36, 37, 39, or 40 with up to two mismatches. Embodiment 69 is the composition, kit, or method of embodiment 1 or 66, wherein the plurality of mec amplification oligomers comprises a mec amplification oligomer that comprises the sequence of SEQ ID NO: 30, 34, 36, 37, 39, or 40.

Embodiment 70 is the composition, kit, or method of any one of embodiments 1 or 66-69, wherein the composition or kit comprises a mec amplification oligomer that competes for hybridization under stringent conditions for binding to a mecA or mecC nucleic acid with an oligomer having a sequence consisting of SEQ ID NO: 31, 35, 38, 45, 48 or 49. Embodiment 71 is the composition, kit, or method of any one of embodiments 1 or 66-70, wherein the composition or kit comprises a mec amplification oligomer that comprises the sequence of SEQ ID NO: 31, 35, 38, 45, 48 or 49 with up to two mismatches. Embodiment 72 is the composition, kit, or method of any one of embodiments 1 or 66-69, wherein the composition or kit comprises a mec amplification oligomer that comprises the sequence of SEQ ID NO: 31, 35, 38, 45, 48 or 49.

Embodiment 73 is the composition, kit, or method of any one of embodiments 1 or 66-72, wherein the composition or kit comprises a mec amplification oligomer that competes for hybridization under stringent conditions for binding to a mecA or mecC nucleic acid with an oligomer having a sequence consisting of SEQ ID NO: 34, 36, 37 or 39. Embodiment 74 is the composition, kit, or method of any one of embodiments 1 or 66-73, wherein the composition or kit comprises a mec amplification oligomer that comprises the sequence of SEQ ID NO: 34, 36, 37 or 39 with up to two mismatches. Embodiment 75 is the composition, kit, or method of any one of embodiments 1 or 66-72, wherein the composition or kit comprises a mec amplification oligomer that comprises the sequence of SEQ ID NO: 34, 36, 37 or 39.

Embodiment 76 is the composition, kit, or method of anyone of embodiments 1 or 66-75, wherein the composition or kit comprises a mec amplification oligomer that competes for hybridization under stringent conditions for binding to a mecC nucleic acid with an oligomer having a sequence consisting of SEQ ID NO: 35, 48, or 49. Embodiment 77 is the composition, kit, or method of any one of embodiments 1 or 66-76, wherein the composition or kit comprises a mec amplification oligomer that comprises the sequence of SEQ ID NO: 35, 48, or 49 with up to two mismatches. Embodiment 78 is the composition, kit, or method of any one of embodiments 1 or 66-75, wherein the composition or kit comprises a mec amplification oligomer that comprises the sequence of SEQ ID NO: 35, 48, or 49.

Embodiment 79 is the composition, kit, or method of any one of embodiments 1 or 66-78, wherein the composition or kit comprises a mec primary detection oligomer that competes for hybridization under stringent conditions for binding to a mecA nucleic acid with an oligomer having a sequence consisting of SEQ ID NO: 29, 33, 41, 43, 112, or 116.

Embodiment 80 is the composition, kit, or method of any one of embodiments 1 or 66-79, wherein the composition or kit comprises a mec primary detection oligomer comprising the sequence of at least one of SEQ ID NOs: 87-91 or 99-103. Embodiment 81 is the composition, kit, or method of any one of embodiments 1 or 66-80, wherein the composition or kit comprises a mec primary detection oligomer that comprises the sequence of SEQ ID NO: 29, 33, 41, 43, 112, or 116 with up to two mismatches. Embodiment 82 is the composition, kit, or method of any one of embodiments 1 or 66-80, wherein the composition or kit comprises a mec primary detection oligomer that comprises the sequence of SEQ ID NO: 29, 33, 41, 43, 112, or 116. Embodiment 83 is the composition, kit, or method of any one of embodiments 1 or 66-82, wherein the composition or kit comprises a mec primary detection oligomer that competes for hybridization under stringent conditions for binding to a mecCnucleic acid with an oligomer having a sequence consisting of SEQ ID NO: 28, 32, 47, 113, or 117. Embodiment 84 is the composition, kit, or method of any one of embodiments 1 or 66-83, wherein the composition or kit comprises a mec primary detection oligomer comprising the sequence of at least one of SEQ ID NOs: 92-94 or 104-106. Embodiment 85 is the composition, kit, or method of any one of embodiments 1 or 66-84, wherein the composition or kit comprises a mec primary detection oligomer that comprises the sequence of SEQ ID NO: 28, 32, 47, 113, or 117 with up to two mismatches. Embodiment 86 is the composition, kit, or method of any one of embodiments 1 or 66-84, wherein the composition or kit comprises a mec primary detection oligomer that comprises the sequence of SEQ ID NO: 28, 32, 47, 113, or 117.

Embodiment 87 is the composition, kit, or method of any one of embodiments 1 or 3-86, wherein the composition or kit comprises at least one pair of S. aureus-specific or S. aureus-indicative amplification oligomers configured to produce an S. aureus-specific or S. aureus-indicative amplicon. Embodiment 88 is the composition, kit, or method of embodiment 87, wherein the pair of S. aureus-specific or S. aureus-indicative amplification oligomers is configured to hybridize specifically to one of nuc, rRNA, femB, Sa442, Staphyloxanthin, or GAPDH in an S. aureus chromosome. Embodiment 89 is the composition, kit, or method of any one of embodiments 2 or 87-88, wherein at least one S. aureus-specific or S. aureus-indicative amplification oligomer competes for binding to S. aureus GAPDH under stringent conditions with an oligomer having a sequence consisting of SEQ ID NO: 20 or 23. Embodiment 90 is the composition, kit, or method of any one of embodiments 2 or 87-89, wherein at least one S. aureus-specific or S. aureus-indicative amplification oligomer comprises the sequence of SEQ ID NO: 20 or 23. Embodiment 91 is the composition, kit, or method of any one of embodiments 2 or 87-90, wherein at least one S. aureus-specific or S. aureus-indicative amplification oligomer competes for binding to S. aureus GAPDH under stringent conditions with an oligomer having a sequence consisting of SEQ ID NO: 21, 24, or 26. Embodiment 92 is the composition, kit, or method of any one of embodiments 2 or 87-91, wherein at least one S. aureus-specific or S. aureus-indicative amplification oligomer comprises the sequence of SEQ ID NO: 21, 24, or 26.

Embodiment 93 is the composition, kit, or method of any one of embodiments 2 or 87-92, wherein the composition or kit comprises at least one S. aureus-specific or S. aureus-indicative primary detection oligomer. Embodiment 94 is the composition, kit, or method of embodiment 93, wherein the S. aureus-specific or S. aureus-indicative primary detection oligomer competes for binding to S. aureus GAPDH under stringent conditions with an oligomer having a sequence consisting of SEQ ID NO: 22, 25, 114, or 118. Embodiment 95 is the composition, kit, or method of embodiment 93 or 94, wherein the S. aureus-specific or S. aureus-indicative primary detection oligomer comprises the sequence of at least one of SEQ ID NO: 95, 96, 107, or 108. Embodiment 96 is the composition, kit, or method of any one of embodiments 93-95, wherein the S. aureus-specific or S. aureus-indicative primary detection oligomer comprises the sequence of SEQ ID NO: 22, 25, 114, or 118.

Embodiment 97 is the composition, kit, or method of any one of embodiments 4-5 or 9-96, wherein the composition or kit further comprises one or more secondary detection oligomers that comprise a label and are configured to interact with a fragment of a primary detection oligomer. Embodiment 98 is the composition, kit, or method of embodiment 97, wherein the one or more secondary detection oligomers are FRET cassettes. Embodiment 99 is the composition, kit, or method of embodiment 97 or 98, wherein the one or more secondary detection oligomers include a secondary detection oligomer comprising the sequence of SEQ ID NO: 58. Embodiment 100 is the composition, kit, or method of any one of embodiments 97-99, wherein the one or more secondary detection oligomers include a secondary detection oligomer comprising the sequence of SEQ ID NO: 19. Embodiment 101 is the composition, kit, or method of any one of embodiments 97-100, wherein the one or more secondary detection oligomers include a secondary detection oligomer comprising the sequence of SEQ ID NO: 27. Embodiment 102 is the composition, kit, or method of any one of the preceding embodiments, wherein the composition or kit comprises a nuclease with structure-specific activity toward a three-strand structure formed by 3'-end invasion.

Embodiment 103 is the composition, kit, or method of any one of the preceding embodiments, wherein the composition or kit comprises a cleavase or 5'-nuclease. Embodiment 104 is the composition, kit, or method of any one of the preceding embodiments, wherein the composition or kit comprises a FEN1 nuclease.

Embodiment 105 is the composition, kit, or method of any one of the preceding embodiments, wherein the composition or kit comprises a polymerase. Embodiment 106 is the composition, kit, or method of any one of the preceding embodiments, wherein the composition or kit comprises a DNA polymerase. Embodiment 107 is the composition, kit, or method of any one of the preceding embodiments, wherein the composition or kit comprises a thermostable DNA polymerase. Embodiment 108 is the composition, kit, or method of embodiment 107, wherein the thermostable DNA polymerase is a hot-start DNA polymerase.

Embodiment 109 is the composition, kit, or method of any one of the preceding embodiments, wherein the composition or kit comprises NTPs. Embodiment 110 is the composition, kit, or method of any one of the preceding embodiments, wherein composition or kit comprises deoxyribonucleotide triphosphates.

Embodiment 111 is a detection oligomer comprising the sequence set forth in anyone of SEQ ID NOs: 85-96 or 119-126, wherein the detection oligomer further comprises sufficient additional sequence to specifically hybridize to a MRSA amplicon. Embodiment 112 is the detection oligomer of embodiment 111, which is configured to specifically hybridize to the reverse complement of the sequence set forth in any one of SEQ ID NOs: 97-108. Embodiment 113 is the detection oligomer of embodiment 111 or 112, comprising the sequence set forth in any one of SEQ ID NOs: 97-108 with up to two mismatches. Embodiment 114 is the detection oligomer of embodiment 111 or 112, comprising the sequence set forth in any one of SEQ ID NOs: 97-108. Embodiment 115 is the detection oligomer of any one of embodiments 111-114, comprising the sequence set forth in any one of SEQ ID NOs: 22, 25, 28, 29, 32, 33, 39, 41, 43, 47, 61, or 62 with up to two mismatches. Embodiment 116 is the detection oligomer of embodiment any one of embodiments 111-114, comprising the sequence set forth in any one of SEQ ID NOs: 22, 25, 28, 29, 32, 33, 39, 41, 43, 47, 61, or 62. Embodiment 117 is the detection oligomer of embodiment any one of embodiments 111-116, wherein the detection oligomer is non-extendable. Embodiment 118 is the detection oligomer of embodiment any one of embodiments 111-117, wherein the detection oligomer comprises a label. Embodiment 119 is the detection oligomer of embodiment any one of embodiments 111-118, wherein the detection oligomer has a length of about 25 to about 45 nucleotides.

Embodiment 120 is a composition or kit comprising at least one detection oligomer of any one of embodiments 111-119 and at least one secondary detection oligomer, wherein the secondary detection oligomer comprises at least one label and is configured to interact with a fragment of the detection oligomer. Embodiment 121 is the composition or kit of embodiment 120, wherein the secondary detection oligomer comprises at least two labels. Embodiment 122 is the composition or kit of embodiment 121, wherein the at least two labels include a FRET pair. Embodiment 123 is the composition or kit of embodiment 121 or 122, wherein the at least two labels include a quencher. Embodiment 124 is the composition or kit of any one of embodiments 121-123, wherein the secondary detection oligomer is a FRET cassette. Embodiment 125 is the composition or kit of any one of embodiments 120-124, wherein the fragment of the detection oligomer is a 5'-terminal flap of at least about six nucleotides. Embodiment 126 is the composition or kit of embodiment 125, wherein the 5'-terminal flap of the detection oligomer has a sequence comprising positions 1-6 as set forth in any one of SEQ ID NOs: 22, 25, 28, 29, 32, 33, 39, 41, 43, 47, 61, or 62.

Embodiment 127 is a method of detecting MRSA nucleic acid comprising: preparing a composition according to any one of embodiments 120-126 or comprising at least one detection oligomer of any one of embodiments 111-119, and further comprising a sample comprising or suspected of comprising MRSA nucleic acid or at least one MRSA amplicon; detecting the presence or absence of the MRSA nucleic acid or the MRSA amplicon by performing a hybridization assay; and determining whether the detection oligomer hybridized to the MRSA nucleic acid or the MRSA amplicon.

Embodiment 128 is the method of embodiment 127, wherein the composition comprises at least one secondary detection oligomer as recited in any one of embodiments 120-126, and the method comprises determining whether the detection oligomer hybridized to the MRSA nucleic acid or the MRSA amplicon comprises exposing the detection oligomer to a structure-specific nuclease and determining whether a fragment of the detection oligomer produced by the structure-specific nuclease interacts with the secondary detection oligomer. Embodiment 129 is the method of embodiment 128, wherein the fragment of the detection oligomer is a 5'-terminal flap. Embodiment 130 is the method of embodiment 128 or 129, wherein the composition further comprises at least one invasive oligomer that hybridizes to a site in the MRSA nucleic acid or the MRSA amplicon that overlaps the hybridization site of the detection oligomer and, in the presence of the detection oligomer and the MRSA nucleic acid or the MRSA amplicon, forms a structure recognized for cleavage by the structure-specific nuclease. Embodiment 131 is the method of embodiment 130, wherein the invasive oligomer competes for hybridization to the MRSA nucleic acid or the MRSA amplicon under stringent conditions with an oligomer having a sequence consisting of the sequence of any one of SEQ ID NOs: 20, 21, 23, 24, 30, 31, 34-40, 45, 46, 48-57, 59, 60, 63-84, 109, or 110. Embodiment 132 is the method of embodiment 130 or 131, wherein the invasive oligomer has a sequence comprising the sequence of any one of SEQ ID NOs: 20, 21, 23, 24, 30, 31, 34-40, 45, 46, 48-57, 59, 60, 63-84, 109, or 110 with up to two mismatches.

Embodiment 133 is the composition, kit, detection oligomer, or method of any one of the preceding embodiments, wherein at least one oligomer comprises at least one methylated cytosine. Embodiment 134 is the composition, kit, detection oligomer, or method of any one of the preceding embodiments, wherein the sequences of SEQ ID NOs include cytosine methylation as indicated in the Table of Sequences. Embodiment 135 is a composition of any one of embodiments 1-2, 4-8, 10-110, 120-126, or 133-134, or comprising a detection oligomer of any one of embodiments 111-119, which is aqueous, frozen, or lyophilized, or wherein at least one oligomer is bound to a solid substrate.

Embodiment 136 is a use of a composition or kit of any one of embodiments 1-2, 4-8, 10-110, 120-126, or 133-135 or a detection oligomer of any one of embodiments 111-119 for detecting a MRSA nucleic acid in a sample.

BRIEF DESCRIPTION OF THE DRAWINGS

FIG. 1A shows the amplification products of MREJ ii, MREJ xv, glyceraldehyde 3-phosphate dehydrogenase (GAPDH), and mecA from MRSA containing MREJ ii, and MRSA containing MREJ xv, methicillin-susceptible *Staphylococcus aureus* (MSSA), and a negative control. FIG. 1B shows amplification signal measured in orfX/SCCmec threshold cycle [Ct] for each sample. The MREJ xv primer concentration is given in M in both of FIGS. 1A-1B.

FIG. 2 shows performance of exemplary oligomers of this disclosure with inclusion of MREJ xv primer in comparison to Cepheid testing (Xpert® SA Nasal Complete) across a panel of MRSA strains containing the MREJ xv sequence. orfX/SCCmec and SCC refers to the junction generated by integration of SCCmec into the orfX gene on the *S. aureus* chromosome. mecA/C and mec refer to the presence of the mecA and/or mecC genes. GAPDH and SPA refer to genes that contain sequence specific to or indicative of *S. aureus*. Data are presented in non-normalized average Ct values.

FIG. 3 shows limit of detection (LoD) analysis for exemplary oligomers on four MRSA strains. Data are presented as percent positivity for individual genes and MRSA/SA call.

FIG. 5 shows cross-reactivity data for a variety of panels containing *Stapholococcus* species when tested with the MRSA assay. Shaded boxes indicating positivity for mecA/C for some panels was due to the mecA gene present in MRSE. IC=internal control; SA=*Staphylococcus aureus*.

DETAILED DESCRIPTION OF CERTAIN EMBODIMENTS

Definitions

Figure 1A:
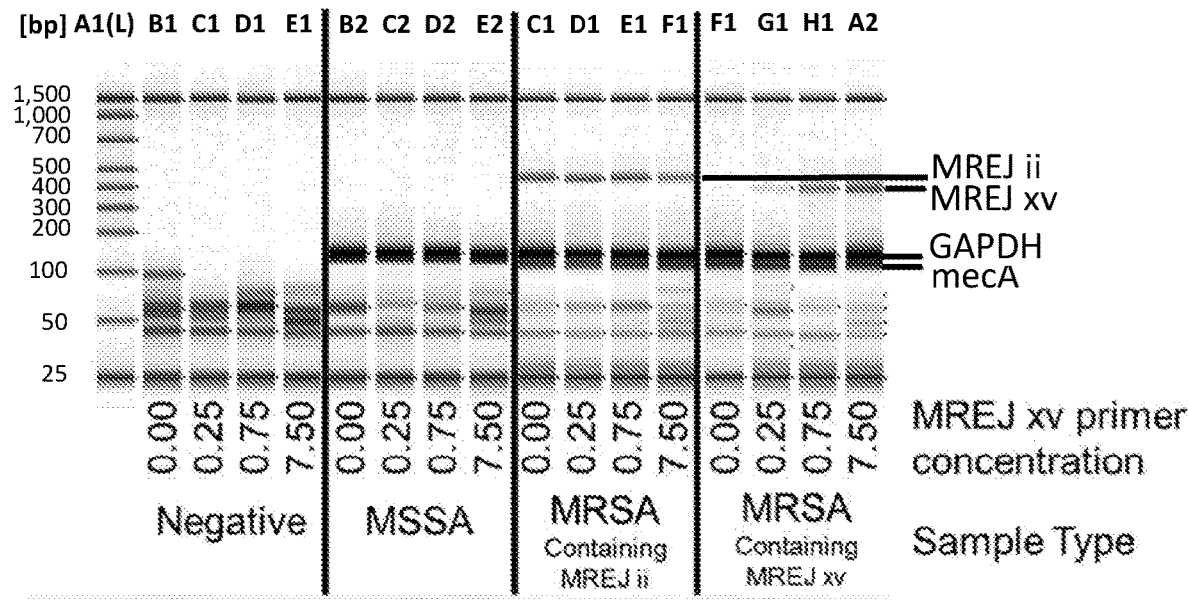
FIGS. 1A-1B show detection and amplification data using exemplary oligomers of this disclosure.

Before describing the present teachings in detail, it is to be understood that the disclosure is not limited to specific compositions or process steps, as such may vary. It should be noted that, as used in this specification and the appended claims, the singular form "a," "an," and "the" include plural references, and expressions such as "one or more items" include singular references unless the context clearly dictates otherwise. Thus, for example, reference to "an oligomer" includes a plurality of oligomers and the like; in a further example, a statement that "one or more secondary detection oligomers are FRET cassettes" includes a situation in which there is exactly one secondary detection oligomer and it is a FRET cassette. The conjunction "or" is to be interpreted in the inclusive sense, i.e., as equivalent to "and/or," unless the inclusive sense would be unreasonable in the context. When "at least one" member of a class (e.g., oligomer) is present, reference to "the" member (e.g., oligomer) refers to the present member (if only one) or at least one of the members (e.g., oligomers) present (if more than one).

It will be appreciated that there is an implied "about" prior to the temperatures, concentrations, times, etc. discussed in the present disclosure, such that slight and insubstantial deviations are within the scope of the present teachings herein. In general, the term "about" indicates insubstantial variation in a quantity of a component of a composition not having any significant effect on the activity or stability of the composition, e.g., within 10%, 5%, 2%, or 1%. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed considering the number of reported significant digits and by applying ordinary rounding techniques. All ranges are to be interpreted as encompassing the endpoints in the absence of express exclusions such as "not including the endpoints"; thus, for example, "within 10-15" includes the values 10 and 15. One skilled in the art will understand that ranges recited herein include all whole and rational numbers within the range (e.g., 90%-100% includes 92% and 98.377%). Also, the use of "comprise," "comprises," "comprising," "contain," "contains," "containing," "include," "includes," and "including" are not intended to be limiting. It is to be understood that both the foregoing general description and detailed description are exemplary and explanatory only and are not restrictive of the teachings. To the extent that any material incorporated by reference is inconsistent with the express content of this disclosure, the express content controls.

Unless specifically noted, embodiments in the specification that recite "comprising" various components are also contemplated as "consisting of" or "consisting essentially of" the recited components; embodiments in the specification that recite "consisting of" various components are also contemplated as "comprising" or "consisting essentially of" the recited components; and embodiments in the specification that recite "consisting essentially of" various components are also contemplated as "consisting of" or "comprising" the recited components (this interchangeability does not apply to the use of these terms in the claims). "Consisting essentially of" means that additional component(s), composition(s) or method step(s) that do not materially change the basic and novel characteristics of the compositions and methods described herein can be included in those compositions or methods. Such characteristics include the ability to detect a MRSA nucleic acid sequence present in a sample with specificity that distinguishes the MRSA nucleic acid from one or more, or all, of MSSA, CNS such as MRSE and/or other non-*S. aureus* Staphylococci, empty cassette MSSA, and other known pathogens. In some embodiments, the characteristics include the ability to detect a MRSA nucleic acid sequence at a sensitivity sufficient to detect as little as about 50 CFU (Colony Forming Units)/mL of MRSA. In some embodiments, the characteristics include the ability to detect a MRSA nucleic acid sequence within about 60 minutes and/or within about 50 cycles from the beginning of an amplification reaction when a cycled amplification reaction is used.

Where a claim to a composition or kit recites an oligomer with a first given feature (e.g., competing for hybridization under stringent conditions for binding to a mecA nucleic acid with an oligomer having a sequence consisting of SEQ ID NO: 29 and claims dependent thereon recite an oligomer with additional given features (e.g., comprising the sequence of at least one of SEQ ID NOs: 87-91 or 99-103), then the composition or kit can comprise a plurality of oligomers that collectively have the features or an individual oligomer with the first and additional features (including but not necessarily limited to when the features are related; e.g., competing for hybridization under stringent conditions for binding to a mecA nucleic acid with an oligomer having a sequence consisting of SEQ ID NO: 29 is related to comprising the sequence of SEQ ID NO: 99 in that SEQ ID NO: 99 is a subsequence of SEQ ID NO: 29).

A "MRSA nucleic acid" generally refers to a nucleic acid found in MRSA, including but not limited to orfX/SCCmec junction, mecA or mecC, and sequences indicative of *S. aureus* (e.g., *S. aureus*-specific sequences). A "MRSA target nucleic acid" is a MRSA nucleic acid that is targeted for amplification and/or detection in a method according to this disclosure. A "MRSA amplicon" is an amplicon produced from the amplification of a MRSA nucleic acid.

An "orfX/SCCmec junction" comprises sequence (i.e., one or more nucleotides) from the *S. aureus* orfX gene joined directly to SCCmec sequence (i.e., one or more nucleotides), such as is formed by integration of SCCmec into the *S. aureus* chromosome. In some embodiments, an orfX/SCCmec junction comprises at least about 20 nucleotides of orfX sequence and at least about 20 nucleotides of SCCmec sequence. In some embodiments, an orfX/SCCmec junction comprises at least about 30, 40, 50, 60, 70, 80, 90, or 100 nucleotides of SCCmec sequence.

An "MREJ" (mec right extremity junction) is the SCCmec-derived portion of an orfX/SCCmec junction.

A "sample" refers to material that may contain a MRSA target nucleic acid, including but not limited to biological, clinical, environmental, and food samples. Environmental samples include environmental material such as surface matter, soil, water and industrial samples, as well as samples obtained from food and dairy processing instruments, apparatus, equipment, utensils, disposable and non-disposable items. "Biological" or "clinical" samples refer to a tissue or material derived from a living or dead human or animal which may contain a MRSA target nucleic acid, including, for example, skin, wound, nasopharyngeal or throat swabs, nasal or bronchial washes, nasal aspirates, sputum, other respiratory tissue or exudates, biopsy tissue including lymph nodes, or body fluids such as blood or urine. A sample can be treated to physically or mechanically disrupt tissue or cell structure to release intracellular nucleic acids into a solution which may contain enzymes, buffers, salts, detergents and the like, to prepare the sample for analysis. These examples are not to be construed as limiting the sample types applicable to the present disclosure.

"Nucleic acid" and "polynucleotide" refer to a multimeric compound comprising nucleosides or nucleoside analogs which have nitrogenous heterocyclic bases or base analogs linked together to form a polynucleotide, including conventional RNA, DNA, mixed RNA-DNA, and polymers that are analogs thereof. A nucleic acid "backbone" can be made up of a variety of linkages, including one or more of sugar-phosphodiester linkages, peptide-nucleic acid bonds ("peptide nucleic acids" or PNA; PCT No. WO 95/32305), phosphorothioate linkages, methylphosphonate linkages, or combinations thereof. Sugar moieties of a nucleic acid can be ribose, deoxyribose, or similar compounds with substitutions, e.g., 2' methoxy or 2' halide substitutions. Nitrogenous bases can be conventional bases (A, G, C, T, U), analogs thereof (e.g., inosine, or others; see *The Biochemistry of the Nucleic Acids* 5-36, Adams et al., ed., 11$^{th}$ ed., 1992), derivatives of purines or pyrimidines (e.g., N$^4$-methyl deoxyguanosine, deaza- or aza-purines, deaza- or aza-pyrimidines, pyrimidine bases with substituent groups at the 5 or 6 position (e.g., 5-methylcytosine), purine bases with a substituent at the 2, 6, or 8 positions, 2-amino-6-methyl-aminopurine, O$^6$-methylguanine, 4-thio-pyrimidines, 4-amino-pyrimidines, 4-dimethylhydrazine-pyrimidines, and 04-alkyl-pyrimidines; U.S. Pat. No. 5,378,825 and PCT No. WO 93/13121). Nucleic acids can include one or more "abasic" residues where the backbone includes no nitrogenous base for position(s) of the polymer (U.S. Pat. No. 5,585,481). A nucleic acid can comprise only conventional RNA or DNA sugars, bases and linkages, or can include both conventional components and substitutions (e.g., conventional bases with 2' methoxy linkages, or polymers containing both conventional bases and one or more base analogs). Nucleic acid includes "locked nucleic acid" (LNA), an analogue containing one or more LNA nucleotide monomers with a bicyclic furanose unit locked in an RNA mimicking sugar conformation, which enhance hybridization affinity toward complementary RNA and DNA sequences (Vester and Wengel, 2004, *Biochemistry* 43(42):13233-41). Embodiments of oligomers that can affect stability of a hybridization complex include PNA oligomers, oligomers that include 2'-methoxy or 2'-fluoro substituted RNA, or oligomers that affect the overall charge, charge density, or steric associations of a hybridization complex, including oligomers that contain charged linkages (e.g., phosphorothioates) or neutral groups (e.g., methylphosphonates). Methylated cytosines such as 5-methylcytosines can be used in conjunction with any of the foregoing backbones/sugars/linkages including RNA or DNA backbones (or mixtures thereof) unless otherwise indicated. RNA and DNA equivalents have different sugar moieties (i.e., ribose versus deoxyribose) and can differ by the presence of uracil in RNA and thymine in DNA. The differences between RNA and DNA equivalents do not contribute to differences in homology because the equivalents have the same degree of complementarity to a particular sequence. It is understood that when referring to ranges for the length of an oligonucleotide, amplicon, or other nucleic acid, that the range is inclusive of all whole numbers (e.g., 19-25 contiguous nucleotides in length includes 19, 20, 21, 22, 23, 24, and 25).

"C residues" include methylated and unmethylated cytosines unless the context indicates otherwise. In some embodiments, methylated cytosines comprise or consist of 5-methylcytosines.

An "oligomer" or "oligonucleotide" refers to a nucleic acid of generally less than 1,000 nucleotides (nt), including those in a size range having a lower limit of about 2 to 5 nt and an upper limit of about 500 to 900 nt. Some particular embodiments are oligomers in a size range with a lower limit of about 5 to 15, 16, 17, 18, 19, or 20 nt and an upper limit of about 50 to 600 nt, and other particular embodiments are in a size range with a lower limit of about 10 to 20 nt and an upper limit of about 22 to 100 nt. Oligomers can be purified from naturally occurring sources, but can be synthesized by using any well known enzymatic or chemical method. Oligomers can be referred to by a functional name (e.g., capture probe, primer or promoter primer) but those skilled in the art will understand that such terms refer to oligomers. Oligomers can form secondary and tertiary structures by self-hybridizing or by hybridizing to other polynucleotides. Such structures can include, but are not limited to, duplexes, hairpins, cruciforms, bends, and triplexes. Oligomers may be generated in any manner, including chemical synthesis, DNA replication, reverse transcription, PCR, or a combination thereof. In some embodiments, oligomers that form invasive cleavage structures are generated in a reaction (e.g., by extension of a primer in an enzymatic extension reaction).

By "amplicon" or "amplification product" is meant a nucleic acid molecule generated in a nucleic acid amplification reaction and which is derived from a target nucleic acid. An amplicon or amplification product contains a target nucleic acid sequence that can be of the same or opposite sense as the target nucleic acid. In some embodiments, an amplicon has a length of about 100-2000 nucleotides, about 100-1500 nucleotides, about 100-1000 nucleotides, about 100-800 nucleotides, about 100-700 nucleotides, about 100-600 nucleotides, or about 100-500 nucleotides.

An "amplification oligonucleotide" or "amplification oligomer" refers to an oligonucleotide that hybridizes to a target nucleic acid, or its complement, and participates in a nucleic acid amplification reaction, e.g., serving as a primer and/or promoter-primer. Particular amplification oligomers contain at least about 10 contiguous bases, and optionally at least 11, 12, 13, 14, 15, 16, 17, 18, 19, or 20 contiguous bases, that are complementary to a region of the target nucleic acid sequence or its complementary strand. The contiguous bases can be at least about 80%, at least about 90%, or completely complementary to the target sequence to which the amplification oligomer binds. In some embodiments, an amplification oligomer comprises an intervening linker or non-complementary sequence between two segments of complementary sequence, e.g., wherein the two complementary segments of the oligomer collectively comprise at least about 10 complementary bases, and optionally at least 11, 12, 13, 14, 15, 16, 17, 18, 19, or 20 complementary bases. Particular amplification oligomers are about 10 to about 60 bases long and optionally can include modified nucleotides.

A "primer" refers to an oligomer that hybridizes to a template nucleic acid and has a 3' end that is extended by polymerization. A primer can be optionally modified, e.g., by including a 5' region that is non-complementary to the target sequence. Such modification can include functional additions, such as tags, promoters, or other sequences used or useful for manipulating or amplifying the primer or target oligonucleotide. A primer modified with a 5' promoter sequence can be referred to as a "promoter-primer." A person of ordinary skill in the art of molecular biology or biochemistry will understand that an oligomer that can function as a primer can be modified to include a 5' promoter sequence and then function as a promoter-primer, and, similarly, any promoter-primer can serve as a primer with or without its 5' promoter sequence.

"Nucleic acid amplification" refers to any in vitro procedure that produces multiple copies of a target nucleic acid sequence, or its complementary sequence, or fragments thereof (i.e., an amplified sequence containing less than the complete target nucleic acid). Examples of nucleic acid amplification procedures include transcription associated methods, such as transcription-mediated amplification (TMA), nucleic acid sequence-based amplification (NASBA) and others (e.g., U.S. Pat. Nos. 5,399,491, 5,554,516, 5,437,990, 5,130,238, 4,868,105, and 5,124,246), replicase-mediated amplification (e.g., U.S. Pat. No. 4,786,600), the polymerase chain reaction (PCR) (e.g., U.S. Pat. Nos. 4,683,195, 4,683,202, and 4,800,159), ligase chain reaction (LCR) (e.g., EP Pat. App. 0320308) and strand-displacement amplification (SDA) (e.g., U.S. Pat. No. 5,422,252). Replicase-mediated amplification uses self-replicating RNA molecules, and a replicase such as QB-replicase. PCR amplification uses DNA polymerase, primers, and thermal cycling steps to synthesize multiple copies of the two complementary strands of DNA or cDNA. LCR amplification uses at least four separate oligonucleotides to amplify a target and its complementary strand by using multiple cycles of hybridization, ligation, and denaturation. SDA uses a primer that contains a recognition site for a restriction endonuclease that will nick one strand of a hemimodified DNA duplex that includes the target sequence, followed by amplification in a series of primer extension and strand displacement steps. Particular embodiments use PCR or TMA, but it will be apparent to persons of ordinary skill in the art that oligomers disclosed herein can be readily used as primers in other amplification methods.

Transcription associated amplification uses a DNA polymerase, an RNA polymerase, deoxyribonucleoside triphosphates, ribonucleoside triphosphates, a promoter-containing oligonucleotide, and optionally can include other oligonucleotides, to ultimately produce multiple RNA transcripts from a nucleic acid template (described in detail in U.S. Pat. Nos. 5,399,491 and 5,554,516, Kacian et al., U.S. Pat. No. 5,437,990, Burg et al., PCT Nos. WO 88/01302 and WO 88/10315, Gingeras et al., U.S. Pat. No. 5,130,238, Malek et al., U.S. Pat. Nos. 4,868,105 and 5,124,246, Urdea et al., PCT No. WO 94/03472, McDonough et al., PCT No. WO 95/03430, and Ryder et al.). Methods that use TMA are described in detail previously (U.S. Pat. Nos. 5,399,491 and 5,554,516).

In cyclic amplification methods that detect amplicons in real-time, the term "Threshold cycle" (Ct) is a measure of the emergence time of a signal associated with amplification of target, and may, for example, be approximately 10× standard deviation of the normalized reporter signal. Once an amplification reaches the "threshold cycle," generally there is considered to be a positive amplification product of a sequence to which the probe binds. The identity of the amplification product can then be determined through methods known to one of skill in the art, such as gel electrophoresis, nucleic acid sequencing, and other such well known methods.

"Detection oligomer" or "probe" refers to an oligomer that interacts with a target nucleic acid to form a detectable complex. Examples include invasive probes and primary probes. An "invasive probe" refers to an oligonucleotide that hybridizes to a target nucleic acid at a location near the region of hybridization between a primary probe and the target nucleic acid, wherein the invasive probe oligonucleotide comprises a portion (e.g., a chemical moiety, or nucleotide, whether complementary to that target or not) that overlaps with the region of hybridization between the primary probe oligonucleotide and the target nucleic acid. The "primary probe" for an invasive cleavage assay includes a target-specific region that hybridizes to the target nucleic acid, and further includes a "5' flap" region that is not complementary to the target nucleic acid. In general, detection can either be direct (i.e., probe hybridized directly to the target) or indirect (i.e., involving an intermediate structure that links a detectable label or detectably labeled molecule (e.g., a FRET cassette) to the target). A probes target sequence generally refers to the specific sequence within a larger sequence which the probe hybridizes specifically. A detection oligomer can include target-specific sequences and a non-target-complementary sequence. Such non-target-complementary sequences can include sequences which will confer a desired secondary or tertiary structure, such as a flap or hairpin structure, which can be used to facilitate detection and/or amplification (e.g., U.S. Pat. Nos. 5,118,801, 5,312,728, 6,835,542, 6,849,412, 5,846,717, 5,985,557, 5,994,069, 6,001,567, 6,913,881, 6,090,543, and 7,482,127; WO 97/27214; WO 98/42873; Lyamichev et al., Nat. Biotech., 17:292 (1999); and Hall et al., PNAS, USA, 97:8272 (2000)). Probes of a defined sequence can be produced by techniques known to those of ordinary skill in the art, such as by chemical synthesis, and by in vitro or in vivo expression from recombinant nucleic acid molecules.

By "probe system" is meant a plurality of detection oligomers or probes for detecting a target sequence. In some embodiments, a probe system comprises at least primary and secondary probes. In some embodiments, a primary probe comprises a target-hybridizing sequence and a non-target-complementary sequence. In some embodiments, a primary probe undergoes nucleolysis (e.g., cleavage, such as 5'-cleavage or endonucleolysis) upon hybridization to a target sequence in the presence of an appropriate nuclease, such as structure-specific nuclease, e.g., a cleavase or 5'-nuclease. In some embodiments, such nucleolysis results in liberation of a "flap" or cleavage fragment from the primary probe that interacts with the secondary probe. In some embodiments, the secondary probe comprises at least one label. In some embodiments, the secondary probe comprises at least a pair of labels, such as an interacting pair of labels, e.g., a FRET pair or a fluorophore and quencher. In some embodiments, interaction of the secondary probe with a liberated flap of the primary probe results in a detectable change in the emission properties of the second probe, e.g., as discussed below with respect to INVADER® assays, FRET, and/or quenching. In some embodiments, a probe system comprises a primary probe and a secondary probe configured to interact with a liberated flap of the primary probe, e.g., the primary probe can be cleaved to give a liberated flap sufficiently complementary to the secondary probe or a segment thereof to form a complex.

By "hybridization" or "hybridize" is meant the ability of two completely or partially complementary nucleic acid strands to come together under specified hybridization assay conditions in a parallel or antiparallel orientation to form a stable structure having a double-stranded region. The two constituent strands of this double-stranded structure, sometimes called a hybrid, are held together by hydrogen bonds. Although these hydrogen bonds most commonly form between nucleotides containing the bases adenine and thymine or uracil (A and T or U) or cytosine and guanine (C and G) on single nucleic acid strands, base pairing can also form between bases which are not members of these "canonical" pairs. Non-canonical base pairing is well-known in the art. (See, e.g., R. L. P. Adams et al., *The Biochemistry of the Nucleic Acids* (11th ed. 1992).)

As used herein, "specific" means pertaining to only one (or to only a particularly indicated group), such as having a particular effect on only one (or on only a particularly indicated group), or affecting only one (or only a particularly indicated group) in a particular way. For example, a cleaved 5' flap specific for a FRET cassette will be able to hybridize to that FRET cassette, form an invasive cleavage structure, and promote a cleavage reaction, but will not be able to hybridize to a different FRET cassette (e.g., a FRET cassette having a different 5' flap-hybridizing sequence) to promote a cleavage reaction. In addition, specific may be used in relation to a combination of oligonucleotides, such as a set of amplification and detection oligonucleotides (e.g., a amplification oligonucleotides may amplify multiple target sequences non-specifically but the detection oligonucleotides will only detect a specific amplified sequence, thus making the combination specific).

As used herein, the term "specifically hybridizes" means that under given hybridization conditions a probe or primer detectably hybridizes substantially only to its target sequence(s) in a sample comprising the target sequence(s) (i.e., there is little or no detectable hybridization to non-targeted sequences). Notably, for example in the case of various MREJ target sequences, an oligomer can be configured to specifically hybridize to any one of a set of targets. Thus, an oligomer described as specifically hybridizing to a first MREJ type can also (but does not necessarily) specifically hybridize to a second (or a second and third, etc.) MREJ type. In some embodiments, an amplification or detection probe oligomer can hybridize to its target nucleic acid to form stable oligomer:target hybrid, but not form a sufficient number of stable oligomer:non-target hybrids for amplification or detection as the case may be. Amplification and detection oligomers that specifically hybridize to a target nucleic acid are useful to amplify and detect target nucleic acids, but not non-targeted nucleic acids, especially non-targeted nucleic acids of phylogenetically closely related organisms. Thus, the oligomer hybridizes to target nucleic acid to a sufficiently greater extent than to non-target nucleic acid to enable one having ordinary skill in the art to accurately amplify and/or detect the presence (or absence) of nucleic acid derived from the specified target (e.g., MRSA) as appropriate. In general, reducing the degree of complementarity between an oligonucleotide sequence and its target sequence will decrease the degree or rate of hybridization of the oligonucleotide to its target region. However, the inclusion of one or more non-complementary nucleosides or nucleobases may facilitate the ability of an oligonucleotide to discriminate against non-targeted nucleic acid sequences.

Specific hybridization can be measured using techniques known in the art and described herein, such as in the examples provided below. In some embodiments, there is at least a 10-fold difference between target and non-target hybridization signals in a test sample, at least a 100-fold difference, or at least a 1,000-fold difference. In some embodiments, non-target hybridization signals in a test sample are no more than the background signal level.

By "stringent hybridization conditions," or "stringent conditions" is meant conditions permitting an oligomer to preferentially hybridize to a target nucleic acid (e.g., MRSA nucleic acid) and not to nucleic acid derived from a closely related non-targeted organisms. While the definition of stringent hybridization conditions does not vary, the actual reaction environment that can be used for stringent hybridization may vary depending upon factors including the GC content and length of the oligomer, the degree of similarity between the oligomer sequence and sequences of targeted and non-targeted nucleic acids that may be present in the test sample. Hybridization conditions include the temperature and the composition of the hybridization reagents or solutions. Exemplary hybridization assay conditions for amplifying and/or detecting target nucleic acids derived from one or more strains of MRSA with the oligomers of the present disclosure correspond to a temperature of about 63° C. to about 67° C. or about 64° C. to about 66° C. when the salt concentration, such as a divalent salt, e.g., $MgCl_2$, is in the range of about 5-21 mM. Additional details of hybridization conditions are set forth in the Examples section. Other acceptable stringent hybridization conditions could be easily ascertained by those having ordinary skill in the art.

"Label" or "detectable label" refers to a moiety or compound joined directly or indirectly to a probe that is detected or leads to a detectable signal. Direct joining can use covalent bonds or non-covalent interactions (e.g., hydrogen bonding, hydrophobic or ionic interactions, and chelate or coordination complex formation) whereas indirect joining can use a bridging moiety or linker (e.g., via an antibody or additional oligonucleotide(s), which amplify a detectable signal. Any detectable moiety can be used, e.g., radionuclide, ligand such as biotin or avidin, enzyme, enzyme substrate, reactive group, chromophore such as a dye or particle (e.g., latex or metal bead) that imparts a detectable color, luminescent compound (e.g. bioluminescent, phosphorescent, or chemiluminescent compound), and fluorescent compound (i.e., fluorophore). Embodiments of fluorophores include those that absorb light (e.g., have a peak absorption wavelength) in the range of about 495 to 690 nm and emit light (e.g., have a peak emission wavelength) in the range of about 520 to 710 nm, which include those known as FAM™, TET™, HEX, CAL FLUOR™ (Orange or Red), CY, and QUASAR™ compounds. Fluorophores can be used in combination with a quencher molecule that absorbs light when in close proximity to the fluorophore to diminish background fluorescence. Such quenchers are well known in the art and include, e.g., BLACK HOLE QUENCHER™ (or BHQ™, Blackberry Quencher® (or BBQ-650®, Eclipse®, or TAMRA™ compounds. Particular embodiments include a "homogeneous detectable label" that is detectable in a homogeneous system in which bound labeled probe in a mixture exhibits a detectable change compared to unbound labeled probe, which allows the label to be detected without physically removing hybridized from unhybridized labeled probe (e.g., U.S. Pat. Nos. 5,283,174, 5,656,207, and 5,658, 737). Exemplary homogeneous detectable labels include chemiluminescent compounds, including acridinium ester ("AE") compounds, such as standard AE or AE derivatives which are well known (U.S. Pat. Nos. 5,656,207, 5,658,737, and 5,639,604). Methods of synthesizing labels, attaching labels to nucleic acid, and detecting signals from labels are well known (e.g., Sambrook et al., *Molecular Cloning, A Laboratory Manual*, 2nd ed. (Cold Spring Harbor Laboratory Press, Cold Spring Harbor, NY, 1989) at Chapt. 10, and U.S. Pat. Nos. 5,658,737, 5,656,207, 5,547,842, 5,283,174, and 4,581,333, and EP Pat. App. 0 747 706). Particular methods of linking an AE compound to a nucleic acid are known (e.g., U.S. Pat. Nos. 5,585,481 and 5,639,604, see column 10, line 6 to column 11, line 3, and Example 8). Particular AE labeling positions are a probe's central region and near a region of A/T base pairs, at a probe's 3' or 5' terminus, or at or near a mismatch site with a known sequence that is the probe should not detect compared to the desired target sequence. Other detectably labeled probes include FRET cassettes, TaqMan™ probes, molecular torches, and molecular beacons. FRET cassettes are discussed in detail below. TaqMan™ probes include a donor and acceptor label wherein fluorescence is detected upon enzymatically degrading the probe during amplification in order to release the fluorophore from the presence of the quencher. Molecular torches and beacons exist in open and closed configurations wherein the closed configuration quenches the fluorophore and the open position separates the fluorophore from the quencher to allow a change in detectable fluorescent signal. Hybridization to target opens the otherwise closed probes.

Sequences are "sufficiently complementary" if they allow stable hybridization of two nucleic acid sequences, e.g., stable hybrids of probe and target sequences, although the sequences need not be completely complementary. That is, a "sufficiently complementary" sequence that hybridizes to another sequence by hydrogen bonding between a subset series of complementary nucleotides by using standard base pairing (e.g., G:C, A:T, or A:U), although the two sequences can contain one or more residues (including abasic positions) that are not complementary so long as the entire sequences in appropriate hybridization conditions to form a stable hybridization complex. Sufficiently complementary sequences can be at least about 80%, at least about 90%, or completely complementary in the sequences that hybridize together. Appropriate hybridization conditions are well known to those skilled in the art, can be predicted based on sequence composition, or can be determined empirically by using routine testing (e.g., Sambrook et al., *Molecular Cloning, A Laboratory Manual*, $2^{nd}$ed. at §§ 1.90-1.91, 7.37-7.57, 9.47-9.51 and 11.47-11.57, particularly §§ 9.50-9.51, 11.12-11.13, 11.45-11.47 and 11.55-11.57).

A "non-extendable" oligomer includes a blocking moiety at or near its 3'-terminus to prevent extension. A blocking group near the 3' end is in some embodiments within five residues of the 3' end and is sufficiently large to limit binding of a polymerase to the oligomer, and other embodiments contain a blocking group covalently attached to the 3' terminus. Many different chemical groups can be used to block the 3' end, e.g., alkyl groups, non-nucleotide linkers, alkane-diol dideoxynucleotide residues (e.g., 3'-hexanediol residues), and cordycepin. Further examples of blocking moieties include a 3'-deoxy nucleotide (e.g., a 2',3'-dideoxy nucleotide); a 3'-phosphorylated nucleotide; a fluorophore, quencher, or other label that interferes with extension; an inverted nucleotide (e.g., linked to the preceding nucleotide through a 3'-to-3' phosphodiester, optionally with an exposed 5'-OH or phosphate); or a protein or peptide joined to the oligonucleotide so as to prevent further extension of a nascent nucleic acid chain by a polymerase. A non-extendable oligonucleotide of the present disclosure can be at least 10 bases in length, and can be up to 15, 20, 25, 30, 35, 40, 50 or more nucleotides in length. Non-extendable oligonucleotides that comprise a detectable label can be used as probes.

References, particularly in the claims, to "the sequence of SEQ ID NO: X" refer to the base sequence of the corresponding sequence listing entry and do not require identity of the backbone (e.g., RNA, 2'-O-Me RNA, or DNA) or base modifications (e.g., methylation of cytosine residues) unless otherwise indicated. Furthermore, T residues are understood to be interchangeable with U residues, and vice versa, unless otherwise indicated.

Unless otherwise indicated, "sense," "positive-sense," or "positive-strand" MRSA or *S. aureus* nucleic acid generally refers to the coding strand of an ORF (open reading frame) or non-coding nucleic acid on the same strand as the coding strand of the transcript, operon, mRNA, etc. of which it is a part, or otherwise of the closest ORF, and "antisense," "negative-sense," "negative-strand" MRSA or *S. aureus* nucleic acid refers to the complement of a "sense," "positive-sense," or "positive-strand" MRSA nucleic acid. Exemplary sense-strand MRSA or *S. aureus* sequences are provided in SEQ ID NOs: 1-18 in the Sequence Table below. Unless otherwise indicated, "hybridizing to a MRSA (or *S. aureus*) nucleic acid" includes hybridizing to either a sense or antisense strand thereof, e.g., either strand of a dsDNA MRSA sequence. Similarly, expressions such as "hybridization to a site comprising position X of SEQ ID NO: Y" and "competing for hybridization to SEQ ID NO: Y" can generally include hybridizing to either a sense or antisense strand of SEQ ID NO: Y; where a hybridized oligomer is configured to produce an amplicon, the proper orientation will be immediately apparent to one skilled in the art.

As used herein, the term "invasive cleavage structure" (or simply "cleavage structure") refers to a structure comprising: (1) a target nucleic acid, (2) an upstream nucleic acid (e.g., an invasive probe oligonucleotide), and (3) a downstream nucleic acid (e.g., a primary probe oligonucleotide), where the upstream and downstream nucleic acids anneal to contiguous regions of the target nucleic acid, and where an overlap forms between the a 3' portion of the upstream nucleic acid and duplex formed between the downstream nucleic acid and the target nucleic acid. An overlap occurs where one or more bases from the upstream and downstream nucleic acids occupy the same position with respect to a target nucleic acid base, whether or not the overlapping base(s) of the upstream nucleic acid are complementary with the target nucleic acid, and whether or not those bases are natural bases or non-natural bases. In some embodiments, the 3' portion of the upstream nucleic acid that overlaps with the downstream duplex is a non-base chemical moiety such as an aromatic ring structure, as disclosed, for example, in U.S. Pat. No. 6,090,543. In some embodiments, one or more of the nucleic acids may be attached to each other, for example through a covalent linkage such as nucleic acid stem-loop, or through a non-nucleic acid chemical linkage (e.g., a multi-carbon chain). An invasive cleavage structure also is created when a cleaved 5' flap hybridizes to a FRET cassette (i.e., when the "target nucleic acid" and the "downstream nucleic acid" are covalently linked in a stem-loop configuration). The "target nucleic acid" sequence of a FRET cassette that hybridizes to a cleaved 5' flap can be referred to as a "5' flap-hybridizing sequence."

As used herein, an "INVADER assay" or "invasive cleavage assay" refers to an assay for detecting target nucleic acid sequences in which an invasive cleavage structure is formed and cleaved in the presence of the target sequence. In some embodiments, reagents for an invasive cleavage assay include: a cleavage agent; and oligonucleotides (e.g., an "invasive probe," a "primary probe," and a "FRET cassette"). In some embodiments the invasive probe is an amplification oligomer or extension product thereof. The invasive cleavage assay can combine two invasive signal amplification reactions (i.e., a "primary reaction" and a "secondary reaction") in series in a single reaction mixture. In some embodiments, detecting the presence of an invasive cleavage structure is achieved using a cleavage agent. The primary probe can be part of a probe system. In some embodiments, an additional portion of the primary probe comprises or consists of a 3' terminal nucleotide which is not complementary to the target nucleic acid and/or which is non-extendable. In some embodiments, an additional portion of the primary probe is configured to interact with a FRET cassette, e.g., comprises a FRET cassette interacting-sequence, e.g., which is not complementary to the target nucleic acid. In some embodiments, the reagents for an INVADER assay further comprise a nuclease, e.g., a cleavase, e.g., a FEN enzyme (e.g., Afu, Ave, RAD2 or XPG proteins) or other enzyme (e.g., a DNA polymerase with 5' nuclease activity, optionally with inactivated or reduced synthetic activity) wherein the nuclease has activity specific for a structure formed when both the invasive and primary probes are hybridized to a target sequence (e.g., a structure that can result when a duplex of the primary probe and the target undergoes 3'-end invasion by the invasive probe, wherein at least the 3' end and/or an intermediate portion of the invasive probe is hybridized, the 5' end of the primary probe is free, and an intermediate and/or 3'-terminal portion of the primary probe is hybridized). In some embodiments, the reagents for an INVADER assay further comprise a buffer solution. In some embodiments, the buffer solution comprises a source of divalent cations (e.g., Mn2+ and/or Mg2+ ions, such as a magnesium salt or manganese salt, e.g., $MgCl_2$, $MnCl_2$, magnesium acetate, manganese acetate, etc.). In some embodiments, the reagents for an INVADER assay further comprise at least one third oligomer, such as at least one amplification oligomer that together with the first oligomer is configured to produce an amplicon, e.g., via PCR. In such embodiments the primary probe can comprise a target-hybridizing sequence configured to specifically hybridize to the amplicon. In some embodiments, the reagents for an INVADER assay further comprise amplification reagents, such as PCR reagents. Embodiments of an INVADER assay in which the target sequence is amplified can be referred to as INVADER PLUS assays. Including amplification in the assay can provide a lower limit of detection. INVADER assays, cleavases, other nucleases, other possible INVADER/INVADER PLUS® reagents, etc., are discussed, for example, in U.S. Pat. Nos. 5,846,717, 5,985,557, 5,994,069, 6,001,567, 6,913,881, 6,090,543, 7,482,127, and 9,096,893; WO 97/27214; WO 98/42873; Lyamichev et al., Nat. Biotech., 17:292 (1999); Hall et al., PNAS, USA, 97:8272 (2000); and WO 2016/179093.

As used herein, the term "flap endonuclease" or "FEN" (e.g., "FEN enzyme") refers to a class of nucleolytic enzymes that act as structure-specific endonucleases on DNA structures with a duplex containing a single-stranded 5' overhang, or flap, on one of the strands that is displaced by another strand of nucleic acid, such that there are overlapping nucleotides at the junction between the single and double-stranded DNA. FEN enzymes catalyze hydrolytic cleavage of the phosphodiester bond 3' adjacent to the junction of single and double stranded DNA, releasing the overhang, or "flap" (see Trends Biochem. Sci. 23:331-336 (1998) and Anna. Rev. Biochem. 73: 589-615 (2004)). FEN enzymes may be individual enzymes, multi-subunit enzymes, or may exist as an activity of another enzyme or protein complex, such as a DNA polymerase. A flap endonuclease may be thermostable. Examples of FEN enzymes useful in the methods disclosed herein are described in U.S. Pat. Nos. 5,614,402; 5,795,763; 6,090,606; and in published PCT applications identified by WO 98/23774; WO 02/070755; WO 01/90337; and WO 03/073067, each of which is incorporated by reference in its entirety. Particular examples of commercially available FEN enzymes include the Cleavase® enzymes (Hologic, Inc.).

"Cassette," when used in reference to an INVADER assay and/or invasive cleavage assay or reaction, as used herein refers to an oligomer or combination of oligomers configured to generate a detectable signal in response to cleavage of a detection oligomer in an INVADER assay. In some embodiments, the cassette hybridizes to an cleavage product (e.g., a "flap") from cleavage of the detection oligomer (e.g., primary probe). In some embodiments, such hybridization results in a detectable change in fluorescence. In some embodiments, such hybridization forms a second invasive cleavage structure, such that the cassette can then be cleaved. In some embodiments, a cassette comprises an interacting pair of labels, e.g., a FRET pair (in which case the cassette is a "FRET cassette"). In some embodiments, a FRET cassette undergoes a detectable change in fluorescence properties upon hybridization to an cleavage product from cleavage of the detection oligomer. For example, a FRET cassette can increase fluorescence emission at a first wavelength and/or decrease fluorescence emission at a second wavelength based on a change in the average distance between labels upon hybridization to a cleavage product from cleavage of the detection oligomer. This can result from a decrease in energy transfer from a donor fluorophore (e.g., a decrease in quenching of a fluorophore or a decrease in energy transfer from a donor fluorophore to an acceptor fluorophore). In some embodiments, a FRET cassette adopts a hairpin conformation, wherein the interaction of the pair of labels substantially suppresses (e.g., quenches) a detectable energy emission (e.g., a fluorescent emission). In some embodiments, a FRET cassette comprises a portion that hybridizes to a complementary cleaved 5' flap of a primary probe to form an invasive cleavage structure that is a substrate for a cleavage agent (e.g., FEN enzyme). In some embodiments, cleavage of the FRET cassette by a cleavage agent separates the donor and acceptor moieties with the result of relieving the suppression and permitting generation of a signal.

An "S. aureus-specific sequence" as used herein refers to a sequence other than an MREJ, orfX, mecA, or mecC sequence that can be used to distinguish S. aureus from other staphylococci including CNS. Non-limiting examples of S. aureus-specific sequences include, but are not limited to sequences in the nuc, rRNA, femB, Sa442, Staphyloxanthin and GAPDH (e.g., SEQ ID NO: 15) genes, and the like, of S. aureus which generally contain distinguishably different sequence in other Staphylococcus species. Discussion of S. aureus-specific sequence detection can be found, e.g., in Schuenck et al., Res. Microbiol., (2006), in press, Shittu et al., (2006), Diagn Microbiol Infect Dis. July 17, Grisold et al., (2006), Methods Mol. Biol. 345: 79-89, Costa et al., (2005), Diag. Microbiol. and Infect. Dis, 51: 13-17, Mc Donald et al., (2005), J. Clin. Microbiol., 43: 6147-6149, Zhang et al., (2005), J. Clin. Microbiol. 43: 5026-5033, Hagen et al. (2005), Int J Med Microbiol. 295:77-86, Maes, et al. (2002) J. Clin. Microbiol. 40:1514-1517, Saito et al., (1995) J. Clin. Microbiol. 33:2498-2500; Ubukata et al., (1992) J. Clin. Microbiol. 30:1728-1733; Murakami et al., (1991) J. Clin. Microbiol. 29:2240-2244; Hiramatsu et al., (1992) Microbiol. Immunol. 36:445-453).

An "*S. aureus*-specific amplicon" is an amplicon produced from an *S. aureus*-specific sequence. In general, production of an *S. aureus*-specific amplicon indicates the presence of *S. aureus* nucleic acid.

As used herein, a "kit" is a packaged combination of reagents, including oligonucleotides having sequences or binding specificities disclosed herein. For example, a kit can include a packaged combination of one or more vials, tubes, or cartridges having a plurality of chambers containing reagents for amplifying and detecting nucleic acids of MRSA bacteria. The reagents can include oligonucleotide primers and probes such as those described herein, as well as nucleotide polymerizing enzymes (e.g., a DNA polymerase, a reverse transcriptase, an RNA polymerase, etc.). Optionally, a flap endonuclease (FEN) enzyme also can be included in the kit. In certain preferred embodiments, the reagents can be in liquid form, in solid form (e.g., a lyophilisate), or a semi-solid form (e.g., a glass). In some embodiments, oligonucleotide reagents and enzyme reagents are present in the kit as components of a single lyophilized composition (e.g., a pellet). In such an instance, primers, probes, and one or more enzymes (e.g., a DNA polymerase and/or a FEN enzyme) can be disposed in the same reaction chamber or vessel in a lyophilized form that can be reconstituted with an aqueous reagent, where a separate vial or tube containing the aqueous reagent is included in the same kit. The kits may further include a number of optional components such as, for example, capture probes (e.g., poly-(k) capture probes as described in US 2013/0209992). Other reagents that may be present in the kits include reagents suitable for performing in vitro amplification such as buffers, salt solutions, and/or appropriate nucleotide triphosphates (e.g., dATP, dCTP, dGTP, dTTP; and/or ATP, CTP, GTP and UTP). Kits further can include a solid support material (e.g., magnetically attractable particles, e.g., magnetic beads) for immobilizing the capture probe, either directly or indirectly, in a sample-preparation procedure. In certain embodiments, the kit further includes a set of instructions for practicing methods in accordance with the present disclosure, where the instructions may be associated with a package insert and/or the packaging of the kit or the components thereof.

Unless defined otherwise, all scientific and technical terms used herein have the same meaning as commonly understood by those skilled in the relevant art. General definitions can be found in technical books relevant to the art of molecular biology, e.g., DICTIONARY OF MICROBIOLOGY AND MOLECULAR BIOLOGY, 2nd ed. (Singleton et al., 1994, John Wiley & Sons, New York, NY) or THE HARPER COLLINS DICTIONARY OF BIOLOGY (Hale & Marham, 1991, Harper Perennial, New York, NY).

Exemplary Compositions, Kits, Methods, and Uses

The present disclosure provides oligomers, compositions, and kits, useful for amplifying and detecting MRSA nucleic acids from a sample.

In some embodiments, oligomers are provided, e.g., in a kit or composition. Oligomers generally comprise a target-hybridizing region, e.g., configured to hybridize specifically to an MRSA nucleic acid. While oligomers of different lengths and base composition can be used for amplifying MRSA nucleic acids, in some embodiments oligomers in this disclosure have target-hybridizing regions from about 10-60 bases in length, about 12-50 bases in length, about 12-40 bases in length, about 12-35 bases in length, or about 12-30 bases in length. In some embodiments, an oligomer comprises a second region of sequence in addition to the target-hybridizing region, which can be located 5' of the target-hybridizing region. In some embodiments, an oligomer does not comprise a second region of sequence. In some embodiments, the second region of sequence is a promoter. In some embodiments, the second region of sequence is configured to interact with a FRET cassette.

In some embodiments, a pair of oligomers is provided wherein one oligomer is configured to hybridize to a sense strand of a MRSA nucleic acid and the other is configured to hybridize to an anti-sense strand of a MRSA nucleic acid. Such oligomers include primer pairs for PCR or other forms of amplification.

In some embodiments, one or more oligomers, such as a primer set (defined as at least two primers configured to generate an amplicon from a target sequence) or a primer set and an additional oligomer (e.g., detection oligomer) which is optionally non-extendible and/or labeled (e.g., for use as a primary probe or part of a probe system, such as together with a FRET cassette), are configured to hybridize to an MREJ. In some embodiments, the primer set comprises at least one forward primer configured to specifically hybridize to orfX and at least one reverse primer configured to specifically hybridize to SCCmec sequence and produce an amplicon with at least one forward primer. When present, the additional oligomer (e.g., detection oligomer) can be configured to specifically hybridize to an amplicon produced by the primer set.

In some embodiments, a plurality of oligomers, such as a plurality of primer sets or a plurality of primer sets and additional oligomers (e.g., detection oligomers) which are optionally non-extendible and/or labeled (e.g., for use as a primary probe, optionally as part of a probe system, such as together with a FRET cassette), are provided which collectively hybridize to an MREJ and at least one of mecA and mecC; an MREJ, mecA, and mecC; an MREJ and an *S. aureus*-specific sequence; an MREJ, at least one of mecA and mecC, and an *S. aureus*-specific sequence; or an MREJ, mecA, mecC, and an *S. aureus*-specific sequence. In some embodiments, the *S. aureus*-specific sequence is a sequence in the nuc, rRNA, femB, Sa442, Staphyloxanthin, or GAPDH gene of *S. aureus*. In some embodiments, the *S. aureus*-specific sequence is a sequence in the GAPDH gene of *S. aureus*. In some embodiments, a plurality of oligomers, such as a plurality of primer sets or a plurality of primer sets and additional oligomers (e.g., detection oligomers) which are optionally non-extendible and/or labeled (e.g., for use as a primary probe, optionally as part of a probe system, such as together with a FRET cassette), are provided which collectively hybridize to an MREJ and a sequence indicative of *S. aureus*; an MREJ, at least one of mecA and mecC, and a sequence indicative of *S. aureus*; or an MREJ, mecA, mecC, and a sequence indicative of *S. aureus* (sometimes referred to as an *S. aureus*-indicative sequence). In some embodiments, the sequence indicative of *S. aureus* is a sequence in the nuc, rRNA, femB, Sa442, Staphyloxanthin, or GAPDH gene of *S. aureus*. In some embodiments, the sequence indicative of *S. aureus* is a sequence in the GAPDH gene of *S. aureus*. In some embodiments, amplification or detection of the sequence indicative of *S. aureus* discriminates the presence of *S. aureus* from many other Staphylococci, e.g., *Staphylococcus arlettae; Staphylococcus auricularis; Staphylococcus capitis; Staphylococcus caprae; Staphylococcus carnosus; Staphylococcus chromogenes; Staphylococcus cohnii* subsp. *Urealyticum; Staphylococcus dephini; Staphylococcus epideridis* (MRSE); *Staphylococcus equorum; Staphylococcus felis; Staphylococcus gallinarum; Staphylococcus haemolytcus; Staphylococcus hominis; Staphylococcus intermedius; Staphylococcus kloosii; Staphylococcus lentus; Staphylococcus pasteuri; Staphylococcus pulverei; Staphylococcus saprophyticus; Staphylococcus sciuri; Staphylococcus simulans; Staphylococcus warneri;* and/or *Staphyococcus xylosus*. In some embodiments, amplification or detection of the sequence indicative of *S. aureus* discriminates the presence of *S. aureus* from CNS. Optionally, amplification or detection of the sequence indicative of *S. aureus* can be highly specific for *S. aureus*, so that nucleic acids from no other known organisms are detected.

In some embodiments, one or more (e.g., at least two) mecA/mecC amplification oligomers are provided. A mecA/mecC amplification oligomer can participate in an amplification reaction of mecA when a mecA sequence is present and an amplification reaction of mecC when a mecC sequence is present. A mecA/mecC amplification oligomer is considered both a mecA amplification oligomer and a mecC amplification oligomer.

Exemplary MREJ sequences are provided in the Sequence Table below. Additional exemplary MREJ sequences are provided, for example, in US Patent Application Pub. Nos. 2008/0227087 and 2013/0266942. The MREJ sequences, primers, and probes disclosed in US Patent Application Pub. Nos. 2008/0227087 and 2013/0266942 are incorporated herein by reference for all purposes.

In some embodiments, a kit or composition according to this disclosure further comprises at least one primer or primer pair for amplifying at least one of an MREJ i through xxi sequence, e.g., a primer or primer pair described in US Patent Application Pub. No. 2008/0227087 or 2013/0266942. In some embodiments, a kit or composition according to this disclosure further comprises at least one primer or primer pair for amplifying at least one of an MREJ x, xi, xvi, xvii, xviii, xix, or xx sequence, e.g., a primer or primer pair described in US Patent Application Pub. No. 2008/0227087 or 2013/0266942.

In some embodiments, one or more oligomers in a set, kit, composition, or reaction mixture comprise a methylated cytosine (e.g., 5-methylcytosine). In some embodiments, at least about half of the cytosines in an oligomer are methylated. In some embodiments, all or substantially all (e.g., all but one or two) of the cytosines in an oligomer are methylated, e.g., one or more cytosines at the 3' end or within 2, 3, 4, or 5 bases of the 3' end are unmethylated.

Exemplary oligomer sets (primer pairs and detection oligomers, e.g., to be labeled or used as primary detection oligomers) and probe systems (primary and secondary detection oligomers) are set forth in the following tables. It should be understood that a detection oligomer in Table A, when used as a primary detection oligomer (e.g., with a structure-specific nuclease, such as in an invasive cleavage assay, e.g., an INVADER or INVADER PLUS® assay), can be combined with any secondary detection oligomer associated with that primary detection oligomer in Table B.

TABLE A

Exemplary oligomer sets. Oligomers are referred to by their SEQ ID NO (see the Sequence Table below). The MREJ type(s) targeted by the exemplary Oligomers for targeting orfX/SCCmec junction in Table A are indicated in parentheses. The mec gene targeted by the exemplary detection oligomers associated with oligomers for targeting mecA and mecC are indicated in parentheses.

| Oligomer 1 (e.g., forward primer) | Oligomer 2 (e.g., reverse primer) | Detection Oligomer (optionally labeled and/or non-extendable, e.g., probe) |
|---|---|---|
| For targeting orfX/SCCmec junction | | |
| 59 | 50, 51, or 52 (i, and ii); 53, 54, or 55 (ii, viii, ix, and xiv); 73, 74, or 75 (iii); 63, 64, or 65 (iv); 56 or 66 (v); 67 or 68 (vi); 76, 77, 78, or 79 (vii); 69, 70, 71, or 72 (ix, xiii, and xiv); 80, 81, or 82 (xii); 83 or 84 (xv); and/or 57 (xxi) | 61, 111, or 115 |
| 60 | 50, 51, or 52 (i, and ii); 53, 54, or 55 (ii, viii, ix, and xiv); 73, 74, or 75 (iii); 63, 64, or 65 (iv); 56 or 66 (v); 67 or 68 (vi); 76, 77, 78, or 79 (vii); 69, 70, 71, or 72 (ix, xiii, and xiv); 80, 81, or 82 (xii); 83 or 84 (xv); and/or 57 (xxi) | 62 |
| For targeting mecA and mecC | | |
| 34 | 35 | 29, 33, 112, or 116 (mecA); and 28, 32, 113, or 117 (mecC) |
| For targeting mecA | | |
| 30 or 34 40 | 31 or 35 45 | 29, 33, 112, or 116 41 & 42*; or 43 & 44* |
| For targeting mecC | | |
| 30 or 34 39 | 31 or 35 31, 35, 48, or 49 | 28, 32, 113, or 117 47 & 46* |
| For targeting GAPDH | | |
| 20 23 | 21, 24, or 26 21, 24, or 26 | 22 25, 114, or 118 |

*used as an invasive oligomer to form a substrate for a structure-specific nuclease together with indicated detection oligomer

TABLE B

Exemplary probe systems. Oligomers are referred to by their SEQ ID NO (see the Sequence Table below).

| Primary Detection Oligomer (optionally non-extendable) | Secondary Detection Oligomer |
|---|---|
| For targeting orfX/SCCmec junction | |
| 61 or 62 | 58 |
| 111 | 19 |
| 115 | 27 |
| For targeting mecA and mecC | |
| 33 (mecA); and 32 (mecC) | 27 |
| 29 (mecA) and 28 (mecC) | 19 |
| 47 (mecC) | 19 |
| 112 (mecA) and 113 (mecC) | 58 |
| For targeting mecA | |
| 29 | 19 |
| 33, 41, or 43 | 27 |
| 112 | 58 |
| For targeting mecC | |
| 28 or 47 | 19 |
| 32 | 27 |
| 113 | 58 |
| For targeting GAPDH | |
| 22 or 25 | 19 |
| 114 | 27 |
| 118 | 58 |

In some embodiments, a plurality of orfX/SCCmec junction (MREJ) amplification oligomers is provided comprising 3, 4, 5, 6, 7, 8, 9, 10, 11, 12, or 13 oligomers that compete for hybridization under stringent conditions with an oligomer associated with at least one MREJ type in Table A to an MREJ sequence.

In some embodiments, a first amplification oligomer comprising a sequence of SEQ ID NO: 36 or 37 and a second amplification oligomer comprising a sequence of SEQ ID NO: 31, 35, or 38 are provided in a kit, composition, or method for amplifying an amplicon from a mecA sequence.

In some embodiments, an oligomer is provided that comprises a label and/or is non-extendable. Such an oligomer can be used as a probe or as part of a probe system (e.g., as a FRET cassette in combination with a target-binding detection oligomer). In some embodiments, the labeled oligomer has a sequence corresponding to a SEQ ID NO listed in the Detection Oligomer column of Table A. In some embodiments, the label is a non-nucleotide label. Suitable labels include compounds that emit a detectable light signal, e.g., fluorophores or luminescent (e.g., chemiluminescent) compounds that can be detected in a homogeneous mixture. More than one label, and more than one type of label, can be present on a particular probe, or detection can rely on using a mixture of probes in which each probe is labeled with a compound that produces a detectable signal (see. e.g., U.S. Pat. Nos. 6,180,340 and 6,350,579). Labels can be attached to a probe by various means including covalent linkages, chelation, and ionic interactions. In some embodiments the label is covalently attached. For example, in some embodiments, a detection probe has an attached chemiluminescent label such as, e.g., an acridinium ester (AE) compound (see. e.g., U.S. Pat. Nos. 5,185,439; 5,639,604; 5,585,481; and 5,656,744). A label, such as a fluorescent or chemiluminescent label, can be attached to the probe by a non-nucleotide linker (see. e.g., U.S. Pat. Nos. 5,585,481; 5,656,744; and 5,639,604). In some embodiments, an oligomer is provided that is non-extendable and hybridizes to a site in a MRSA nucleic acid that overlaps the hybridization site of an additional oligomer in a kit or composition, such as an amplification oligomer. Hybridization of such oligomers can form a substrate for a structure-specific nuclease, e.g., as part of the detection mechanism in an INVADER or INVADER PLUS assay.

In some embodiments, a labeled oligomer (e.g., comprising a fluorescent label) further comprises a second label that interacts with the first label. For example, the second label can be a quencher. Such probes can be used (e.g., in TaqMan™ assays) where hybridization of the probe to a target or amplicon followed by nucleolysis by a polymerase comprising 5'-3' exonuclease activity results in liberation of the fluorescent label and thereby increased fluorescence, or fluorescence independent of the interaction with the second label. Such probes can also be used (e.g., in INVADER or INVADER PLUS assays (e.g., as FRET cassettes)). In some embodiments, the labeled oligomer has a SEQ ID NO listed in the Secondary Detection Oligomer column of Table B.

In some applications, one or more probes exhibiting at least some degree of self-complementarity are used to facilitate detection of probe:target duplexes in a test sample without first requiring the removal of unhybridized probe prior to detection. Specific embodiments of such detection probes include, for example, probes that form conformations held by intramolecular hybridization, such as conformations generally referred to as hairpins. Suitable hairpin probes include a "molecular torch" (see. e.g., U.S. Pat. Nos. 6,849,412; 6,835,542; 6,534,274; and 6,361,945) and a "molecular beacon" (see. e.g., U.S. Pat. Nos. 5,118,801 and 5,312,728). Molecular torches include distinct regions of self-complementarity (coined "the target binding domain" and "the target closing domain") which are connected by a joining region (e.g., a —(CH$_2$CH$_2$O)$_3$— linker) and which hybridize to one another under predetermined hybridization assay conditions. When exposed to an appropriate target or denaturing conditions, the two complementary regions (which can be fully or partially complementary) of the molecular torch melt, leaving the target binding domain available for hybridization to a target sequence when the predetermined hybridization assay conditions are restored. Molecular torches are designed so that the target binding domain favors hybridization to the target sequence over the target closing domain. The target binding domain and the target closing domain of a molecular torch include interacting labels (e.g., fluorescent/quencher) positioned so that a different signal is produced when the molecular torch is self-hybridized as opposed to when the molecular torch is hybridized to a target nucleic acid, thereby permitting detection of probe:target duplexes in a test sample in the presence of unhybridized probe having a viable label associated therewith.

Examples of interacting donor/acceptor label pairs that can be used in connection with the disclosure include fluorescein/tetramethylrhodamine, IAEDANS/fluororescein, EDANS/DABCYL, coumarin/DABCYL, fluorescein/fluorescein, BODIPY® FL/BODIPY® FL, fluorescein/DABCYL, lucifer yellow/DABCYL, BODIPY®/DABCYL, eosine/DABCYL, erythrosine/DABCYL, tetramethylrhodamine/DABCYL, Texas Red/DABCYL, CY5/BHQ1®, CY5/BHQ2®, CY3/BHQ1®, CY3/BHQ2® and fluorescein/QSY7® dye. Those having an ordinary level of skill in the art will understand that when donor and acceptor dyes are different, energy transfer can be detected by the appearance of sensitized fluorescence of the acceptor or by quenching of donor fluorescence. Non-fluorescent acceptors such as DABCYL and the QSY7® dyes advantageously eliminate the potential problem of background fluorescence resulting from direct (i.e., non-sensitized) acceptor excitation. Exemplary fluorophore moieties that can be used as one member of a donor-acceptor pair include fluorescein, HEX, ROX, and the CY dyes (such as CY5). Exemplary quencher moieties that can be used as another member of a donor-acceptor pair include DABCYL BLACKBERRY QUENCHER® which are available from Berry and Associates (Dexter, MI), and the BLACK HOLE QUENCHER® moieties which are available from Biosearch Technologies, Inc., (Novato, Calif.). One of ordinary skill in the art will be able to use appropriate pairings of donor and acceptor labels for use in various detection formats (e.g., FRET, TaqMan™, INVADER, etc).

In some embodiments, a detection oligomer (e.g., probe, primary probe, or labeled probe) is non-extendable. For example, the labeled oligomer can be rendered non-extendable by a 3'-adduct (e.g., 3'-phosphorylation or 3'-alkanediol), having a 3'-terminal 3'-deoxynucleotide (e.g., a terminal 2',3'-dideoxynucleotide), having a 3'-terminal inverted nucleotide (e.g., in which the last nucleotide is inverted such that it is joined to the penultimate nucleotide by a 3' to 3' phosphodiester linkage or analog thereof, such as a phosphorothioate), or having an attached fluorophore, quencher, or other label that interferes with extension (possibly but not necessarily attached via the 3' position of the terminal nucleotide). In some embodiments, the 3'-terminal nucleotide is not methylated. In some embodiments, a detection oligomer comprises a 3'-terminal adduct such as a 3'-alkanediol (e.g., hexanediol).

In some embodiments, an oligomer such as a detection oligomer is configured to specifically hybridize to a MRSA amplicon (e.g., the oligomer comprises or consists of a target-hybridizing sequence sufficiently complementary to the amplicon for specific hybridization). The target-hybridizing sequence can include additional nucleotides beyond the sequence of any SEQ ID NO or variant thereof present in the oligomer. An oligomer that comprises the sequences of more than one SEQ ID NO can comprise those sequences in an overlapping manner to the extent that the SEQ ID NOs contain common segments; for example, SEQ ID NOs: 85 and 97 overlap with respect to the last 6 nucleotides of SEQ ID NO: 85 and the first six nucleotides of SEQ ID NO: 97.

Also provided by the disclosure is a reaction mixture for determining the presence or absence of a MRSA target nucleic acid in a sample. A reaction mixture in accordance with the present disclosure comprises at least one or more of the following: an oligomer combination as described herein for amplification of a MRSA target nucleic acid; and a detection probe oligomer as described herein for determining the presence or absence of a MRSA amplification product.

The reaction mixture can further include a number of optional components such as, for example, capture probes (e.g., poly-(k) capture probes as described in US 2013/0209992, which is incorporated herein by reference). For an amplification reaction mixture, the reaction mixture will typically include other reagents suitable for performing in vitro amplification such as, buffers, salt solutions, appropriate nucleotide triphosphates (e.g., dATP, dCTP, dGTP, and one or both of dTTP or dUTP; and/or ATP, CTP, GTP and UTP), and/or enzymes (e.g., a thermostable DNA polymerase, and/or reverse transcriptase and/or RNA polymerase and/or FEN enzyme), and will typically include test sample components, in which a MRSA target nucleic acid may or may not be present. A reaction mixture can include amplification oligomers for at least one target region of a MRSA genome, such as, it can include amplification oligomers for multiple MRSA target regions such as the orfX/SCCmec junction (e.g., including multiple types thereof as discussed above), mecA and/or mecC, and an S. aureus-specific sequence such as GAPDH. A reaction mixture can include amplification oligomers for at least one target region of a MRSA genome, such as, it can include amplification oligomers for multiple MRSA target regions such as the orfX/SCCmec junction (e.g., including multiple types thereof as discussed above), mecA and/or mecC, and a sequence indicating the presence of a S. aureus nucleic acid sequence, such as GAPDH. In addition, for a reaction mixture that includes a detection probe together with an amplification oligomer combination, selection of amplification oligomers and detection probe oligomers for a reaction mixture are linked by a common target region (i.e., the reaction mixture will include a probe that binds to a sequence amplifiable by an amplification oligomer combination of the reaction mixture).

Also provided by the subject disclosure are kits for practicing the methods as described herein. A kit in accordance with the present disclosure comprises at least one or more of the following: an amplification oligomer combination as described herein for amplification of a MRSA target nucleic acid; and at least one detection probe oligomer as described herein for determining the presence or absence of a MRSA amplification product. In some embodiments, any oligomer combination described herein is present in the kit. The kits can further include a number of optional components such as, for example, capture probes (e.g., poly-(k) capture probes as described in US 2013/0209992).

Other reagents that can be present in the kits include reagents suitable for performing in vitro amplification such as, e.g., buffers, salt solutions, appropriate nucleotide triphosphates (e.g., dATP, dCTP, dGTP, and one or both of dTTP or dUTP; and/or ATP, CTP, GTP and UTP), and/or enzymes (e.g., a thermostable DNA polymerase, and/or reverse transcriptase and/or RNA polymerase and/or FEN enzyme), and will typically include test sample components, in which a MRSA target nucleic acid may or may not be present. A kit can include amplification oligomers for at least one target region of a MRSA genome or amplification oligomers for multiple MRSA target regions such as the orfX/SCCmec junction (e.g., including multiple types thereof as discussed above), mecA and/or mecC, and an S. aureus-specific sequence or a sequence indicative of S. aureus such as GAPDH. In addition, for a kit that includes a detection probe together with an amplification oligomer combination, selection of amplification oligomers and detection probe oligomers for a reaction mixture are linked by a common target region (i.e., the reaction mixture will include a probe that binds to a sequence amplifiable by an amplification oligomer combination of the reaction mixture). In certain embodiments, the kit further includes a set of instructions for practicing methods in accordance with the present disclosure, where the instructions can be associated with a package insert and/or the packaging of the kit or the components thereof.

Any method disclosed herein is also to be understood as a disclosure of corresponding uses of materials involved in the method directed to the purpose of the method. Any of the oligomers comprising MRSA sequence and any combinations (e.g., kits and compositions, including but not limited to reaction mixtures) comprising such an oligomer are to be understood as also disclosed for use in detecting or quantifying MRSA, and for use in the preparation of a composition for detecting MRSA.

Broadly speaking, methods can comprise one or more of the following components: target capture, in which MRSA nucleic acid (e.g., from a sample, such as a clinical sample) is annealed to a capture oligomer (e.g., a specific or non-specific capture oligomer); isolation (e.g., washing, to remove material not associated with a capture oligomer); amplification; and amplicon detection, which for example can be performed in real time with amplification. Certain embodiments involve each of the foregoing steps. Certain embodiments involve exponential amplification, optionally with a preceding linear amplification step. Certain embodiments involve exponential amplification and amplicon detection. Certain embodiments involve any two of the components listed above. Certain embodiments involve any two components listed adjacently above (e.g., washing and amplification, or amplification and detection).

In some embodiments, amplification comprises (1) contacting the sample with at least two oligomers for amplifying a MRSA nucleic acid target region corresponding to a MRSA target nucleic acid, where the oligomers include at least two amplification oligomers as described above (e.g., one or more oriented in the sense direction and one or more oriented in the antisense direction for exponential amplification); (2) performing an in vitro nucleic acid amplification reaction, where any MRSA target nucleic acid present in the sample is used as a template for generating an amplification product; and (3) detecting the presence or absence of the amplification product, thereby determining the presence or absence of MRSA nucleic acid sequences in the sample.

A detection method in accordance with the present disclosure can further include the step of obtaining the sample to be subjected to subsequent steps of the method. In certain embodiments, "obtaining" a sample to be used includes, for example, receiving the sample at a testing facility or other location where one or more steps of the method are performed, and/or retrieving the sample from a location (e.g., from storage or other depository) within a facility where one or more steps of the method are performed.

In certain embodiments, the method includes purifying the MRSA target nucleic acid from other components (e.g., non-nucleic acid components) in a sample before an amplification (e.g., a capture step). Such purification can include methods of separating and/or concentrating organisms contained in a sample from other sample components, or removing or degrading non-nucleic acid sample components (e.g., protein, carbohydrate, salt, lipid, etc). In some embodiments, RNA in the sample is degraded (e.g., with RNase and/or heat), and optionally the RNase is removed or inactivated and/or degraded RNA is removed.

In particular embodiments, purifying the target nucleic acid includes capturing the target nucleic acid to specifically or non-specifically separate the target nucleic acid from other sample components. Non-specific target capture methods can involve selective precipitation of nucleic acids from a substantially aqueous mixture, adherence of nucleic acids to a support that is washed to remove other non-nucleic acid sample components, or other means of physically separating nucleic acids from a mixture that contains MRSA nucleic acid and other sample components.

Target capture can occur in a solution phase mixture that contains one or more capture probe oligomers that hybridize to the MRSA target sequence under hybridizing conditions. For embodiments comprising a capture probe tail, the MRSA-target:capture-probe complex is captured by applying hybridization conditions so that the capture probe tail hybridizes to the immobilized probe. Certain embodiments use a particulate solid support, such as paramagnetic beads.

Isolation can follow capture, wherein the complex on the solid support is separated from other sample components. Isolation can be accomplished by any appropriate technique (e.g., washing a support associated with the MRSA-target-sequence one or more times (e.g., 2 or 3 times) to remove other sample components and/or unbound oligomer). In embodiments using a particulate solid support, such as paramagnetic beads, particles associated with the MRSA-target can be suspended in a washing solution and retrieved from the washing solution, in some embodiments by using magnetic attraction. To limit the number of handling steps, the MRSA target nucleic acid can be amplified by simply mixing the MRSA target sequence in the complex on the support with amplification oligomers and proceeding with amplification steps.

Exponentially amplifying a MRSA target sequence utilizes an in vitro amplification reaction using at least two amplification oligomers that flank a target region to be amplified. In some embodiments, at least two amplification oligomers as described above are provided. In some embodiments, a plurality of pairs of amplification oligomers is provided, wherein the plurality comprises oligomer pairs configured to hybridize to MREJ sequences of at least 2, 3, 4, 5, 6, 7, 8, 9, 10, 11, 12, 13, or more types of MRSA MREJ sequences. In some embodiments, such types of MRSA MREJ sequences include at least 2, 3, 4, 5, 6, 7, 8, 9, 10, 11, 12, 13, or 14 of MREJ types i, ii, iii, iv, v, vi, vii, viii, ix, xii, xiii, xiv, xv, or xxi. The amplification reaction can be cycled or isothermal. Suitable amplification methods include, for example, replicase-mediated amplification, polymerase chain reaction (PCR), ligase chain reaction (LCR), strand-displacement amplification (SDA), and transcription-mediated amplification (TMA).

A detection step can be performed using any of a variety of known techniques to detect a signal specifically associated with the amplified target sequence, such as by hybridizing the amplification product with a labeled detection probe and detecting a signal resulting from the labeled probe (including from label released from the probe following hybridization in some embodiments). In some embodiments, the labeled probe comprises a second moiety, such as a quencher or other moiety that interacts with the first label, as discussed above. The detection step can also provide additional information on the amplified sequence, such as all or a portion of its nucleic acid sequence. Detection can be performed after the amplification reaction is completed, or can be performed simultaneously with amplifying the target region (e.g., in real time). In one embodiment, the detection step allows homogeneous detection (e.g., detection of the hybridized probe without removal of unhybridized probe from the mixture (see. e.g., U.S. Pat. Nos. 5,639,604 and 5,283,174)). In some embodiments, the nucleic acids are associated with a surface that results in a physical change, such as a detectable electrical change. Amplified nucleic acids can be detected by concentrating them in or on a matrix and detecting the nucleic acids or dyes associated with them (e.g., an intercalating agent such as ethidium bromide or cyber green), or detecting an increase in dye associated with nucleic acid in solution phase. Other methods of detection can use nucleic acid detection probes that are configured to specifically hybridize to a sequence in the amplified product and detecting the presence of the probe: product complex, or by using a complex of probes that can amplify the detectable signal associated with the amplified products (e.g., U.S. Pat. Nos. 5,424,413; 5,451,503; and 5,849,481; each incorporated by reference herein). Directly or indirectly labeled probes that specifically associate with the amplified product provide a detectable signal that indicates the presence of the target nucleic acid in the sample. In particular, the amplified product will contain a target sequence in or complementary to a sequence in the MRSA chromosome, and a probe will bind directly or indirectly to a sequence contained in the amplified product to indicate the presence of MRSA nucleic acid in the tested sample.

In embodiments that detect the amplified product near or at the end of the amplification step, a linear detection probe can be used to provide a signal to indicate hybridization of the probe to the amplified product. One example of such detection uses a luminescently labeled probe that hybridizes to target nucleic acid. The luminescent label is then hydrolyzed from non-hybridized probe. Detection is performed by chemiluminescence using a luminometer (see, e.g., International Patent Application Pub. No. WO 89/002476). In other embodiments that use real-time detection, the detection probe can be a hairpin probe such as a molecular beacon, molecular torch, or hybridization switch probe that is labeled with a reporter moiety that is detected when the probe binds to amplified product. Such probes can comprise target-hybridizing sequences and non-target-hybridizing sequences. Various forms of such probes are described, e.g., in U.S. Pat. Nos. 5,118,801; 5,312,728; 5,925,517; 6,150,097; 6,849,412; 6,835,542; 6,534,274; and 6,361,945; and US Patent Application Pub. Nos. 2006/0068417A1 and 2006/0194240A1).

In some embodiments, amplified product is detected through an invasive cleavage assay that provides means for forming an invasive cleavage structure that requires the presence of a target nucleic acid. The assay further involves cleaving the invasive cleavage structure to release distinctive cleavage products. A cleavage agent such as a FEN enzyme, for example, is used to cleave the target-dependent invasive cleavage structure, thereby resulting in cleavage products that indicate the presence of specific target nucleic acid sequences in the sample. When two oligonucleotides hybridize to a target nucleic acid strand such that they form an overlapping invasive cleavage structure, as defined above, invasive cleavage can occur. Through the interaction of a cleavage agent (e.g., FEN enzyme) and the upstream oligonucleotide (i.e., the invasive probe), the cleavage agent can be made to cleave the downstream oligonucleotide (i.e., the primary probe) at an internal site such that a distinctive fragment is produced. The fragment, sometimes referred to as a "liberated flap" or "cleaved 5' flap" or simply a "flap" can then itself interact with a secondary probe such as a FRET cassette (e.g., by participating as an invasive probe in a subsequent reaction that generates a detectable signal (e.g., a fluorescent signal)). Such embodiments are described in U.S. Pat. Nos. 5,846,717, 5,985,557, 5,994,069, 6,001,567, and 6,090,543, WO 97/27214, WO 98/42873, Nat. Biotech., 17:292 (1999), PNAS, 97:8272 (2000), and WO 2016/179093. More specifically, a plurality of INVADER reactions, e.g., combined in a single reaction mixture, can be used for the multiplex applications disclosed herein, including detection of various orfX-SCCmec junctions, mecA, mecC, an *S. aureus*-specific gene, and/or an internal control.

Invasive cleavage assays can be used for detecting specific target sequences in unamplified, as well as amplified DNA (e.g., PCR product(s)), including genomic DNA, RNA, or an amplicon thereof. The primary probe and the invasive probe hybridize in tandem to the target nucleic acid to form an overlapping structure. An unpaired "flap" is included on the 5' end of the primary probe. A cleavage agent (e.g. a FEN enzyme, such as the Cleavase® enzymes available from Hologic, Inc.) recognizes the overlap and cleaves off the unpaired 5' flap. In some embodiments, in a secondary reaction, this cleaved product serves as an invasive probe on a FRET cassette to again create a structure recognized by the structure-specific enzyme. When the two labels on a single FRET cassette are separated by cleavage, a detectable fluorescent signal above background fluorescence is produced. Consequently, cleavage of this second invasive cleavage structure results in an increase in fluorescence, indicating the presence of the target sequence.

In some embodiments, one or more of an internal amplification control polynucleotide ("internal control"; e.g., a plasmid, plasmid fragment, or other polynucleotide, generally with a sequence unrelated to MRSA sequences, e.g., to orfX, MREJ, mecA, mecC, and an *S. aureus*-specific or *S. aureus*-indicative gene), and oligomers for amplifying and detecting the internal control are provided as components of a composition or kit disclosed herein and/or are used in a method disclosed herein. Detection of an amplicon from the internal control can serve to avoid false negatives due to instrument or reagent failures when no target sequences are detected.

Below is a table illustrating interpretation of various possible results obtained from methods according to this disclosure. In some embodiments, results are interpreted according to this table. U indicates that detection of an amplicon is expected but unnecessary to the call.

TABLE C

Interpretation of Results

| Amplicon Detection Results | | | | | |
|---|---|---|---|---|---|
| orfX/SCCmec junction | mecA/C | S. aureus-specific or indicative gene (e.g, GAPDH) | Internal Control | MRSA Call | SA Call |
| + | + | + | U | Positive | Positive |
| − | − | + | U | Negative | Positive |
| + | − | + | U | Negative | Positive |
| − | + | − | U | Negative | Negative |
| − | − | − | + | Negative | Negative |
| − | − | − | − | Invalid | Invalid |

Abbreviations are as defined above.

EXAMPLES

The following examples are provided to illustrate certain disclosed embodiments and are not to be construed as limiting the scope of this disclosure in any way.

General Reagents and Methods.

Unless otherwise indicated, non-specific target capture was used to isolate target nucleic acid. Exemplary non-specific target capture reagents and procedures are disclosed in Becker et al., US2013/0209992A1. Target capture procedures were generally performed using a Panther Fusion™ instrument.

Unless otherwise indicated, amplifications were performed on a Panther Fusion™ instrument or an ABI 7500 Fast™ instrument. Unless otherwise indicated, amplifications were performed with combinations of oligomers disclosed above designed to detect a plurality of orfX/SCCmec junction sequences (i.e., some or all of MREJ i, ii, iii, iv, v, vi, vii, ix, xii, xiii, xiv, xv, and xxi). These sequences were detected with an orfX amplification oligomer configured to specifically hybridize to a site comprising position 192 of SEQ ID NO: 16 and a primary detection oligomer together with a plurality of reverse amplification oligomers in INVADER PLUS assays as described above. Some reverse amplification oligomers amplify more than one MREJ type (e.g., MREJ i and MREJ ii; MREJ ii, viii, ix, and xiv; or MREJ xiii, ix, and xiv) such that the number of reverse primers can be fewer than the number of MREJ types that can be detected. The amplification oligomers for detection of the various types of orfX/SCCmec (MREJ) junctions can be further multiplexed with amplification oligomers for amplifying and detecting one or both of mecA and mecC; an *S. aureus*-specific or *S. aureus*-indicative gene such as GAPDH; and an internal control. An internal control plasmid was also generally included in the reactions.

Cleavase used in these Examples was the Afu FEN-1 endonuclease described in U.S. Pat. No. 9,096,893.

Amplification reagents were dNTPs at 0.2-0.8 mM each, a commercially available hot-start Taq polymerase, $MgCl_2$, Cleavase, MOPS and Tris buffers, non-acetylated BSA, and other components supplied by Promega® Master Mix. Primers were supplied at a final concentration of 0.2-0.75 µM unless otherwise indicated. PCR annealing temperatures were varied from 63° C. to 67° C. in various reactions without affecting positivity.

As noted above, detection of amplicons used INVADER PLUS chemistry. A primer served as the invasive probe. The reactions included an orfX/SCCmec primary probe with a target-hybridizing sequence specific for the orfX portion of orfX/SCCmec amplicons and, where applicable, mecA and/or mecC primary probes, a GAPDH primary probe, and an internal control primary probe. For each primary probe there was a corresponding FRET cassette labeled with a interactive label pair in an energy transfer relationship, where fluorescence emission was quenched when both members of the label pair were attached to the FRET cassette (see discussion in Example 1 regarding use of one FRET cassette configured to interact with a liberated flap from either of the mecA or mecC primary probes). Thus, a positive signal for a given target was generally interpreted as indicating that a target sequence was present and amplified by a corresponding set of primers; primary that an invasive cleavage structure comprising a primer, the amplicon, and the corresponding primary probe had been formed and cleaved by Cleavase; that the flap thereby liberated from the primary probe formed an invasive cleavage structure with the corresponding FRET cassette, which was then cleaved by Cleavase, thereby allowing fluorescent detection of a labeled cleavage product of the FRET cassette.

All references to SEQ ID NOs in the Examples section include the cytosine methylation, labels, and other features indicated in the Table of Sequences below.

Example 1. Assay Configuration and MREJ Type xv Oligomer Compatibility

A combination of oligomers was tested for the ability to detect MRSA strains, including MRSA containing the MREJ xv sequence at the orfX/SCCmec junction. MRSA strains containing the MREJ xv sequence include the Bengal Bay Clone.

The combination of oligomers targeted three regions of the MRSA genome (orfX/SCCmec junction, mecA/C, and GAPDH). A plasmid-based internal control was also used, which was generally detected by a Cyanine 5.5 Phosphoramidite (Cy5.5)-labeled FRET oligomer.

The mec amplification and detection oligomers were designed to detect both of the two genes that may be present in SCCmec that convey methicillin resistance (i.e., mecA and mecC). In some configurations of the assay, both targets were amplified by the same oligomer pair but detected by mecA- or mecC-specific primary detection oligomers that each interact with the same FRET cassette, which thus generates signal in a given channel (e.g., FAM or HEX) if either the mecA or mecC target is present. GAPDH was targeted for detection because it contains a highly conserved sequence present in and indicative of or specific to *Staphylococcus aureus*.

Following non-specific target capture, lyophilized amplification and detection reagents were reconstituted and combined with the isolated nucleic acid. This combined reaction mixture was then subjected to thermal cycling to amplify and detect the target nucleic acid sequences. The results from each assay were analyzed, evaluating call and analyte Ct values (when available).

An exemplary fluorophore and quencher pair used is listed in Table D. The Cal Fluor Red 610-BHQ-2 labeled FRET cassette contains 5', internal, and 3' modifications. The 5' modification is a fluorophore which fluoresces at a specific wavelength within the visible spectrum, the internal modification is a non-fluorescent quencher which quenches fluorescence emitted by the fluorophore via Fluorescence Resonance Energy Transfer (FRET), and the 3' modification is hexanediol which prevents extension of the oligo during PCR amplification. The FRET cassette interacted with a primary probe cleaved flap produced by an INVADER reaction in the presence of the target sequence, resulting in increased fluorescence from the 5' label because the fluorophore is cleaved from the FRET cassette, thereby eliminating the quenching effect present in the intact dual labeled FRET cassette. See the general methods section above for additional discussion of the INVADER PLUS reactions. For multiplexed detection, other FRET cassettes were used with labels that fluoresce at different wavelengths of the visible spectrum following invasive cleavage. Exemplary labels are discussed above.

TABLE D

Fluorophore and quencher information

| Description | Fluorophore/ Quencher | Molecular Weight (upon addition to an oligo) | Absorbance Max (nm) | Emission Max (nm) |
|---|---|---|---|---|
| Cal Fluor Red 610 | Fluorophore | 636.7 | 590 | 610 |
| BHQ-2-dT | Quencher | 962.99 | 592 | none |

Figure 1B:
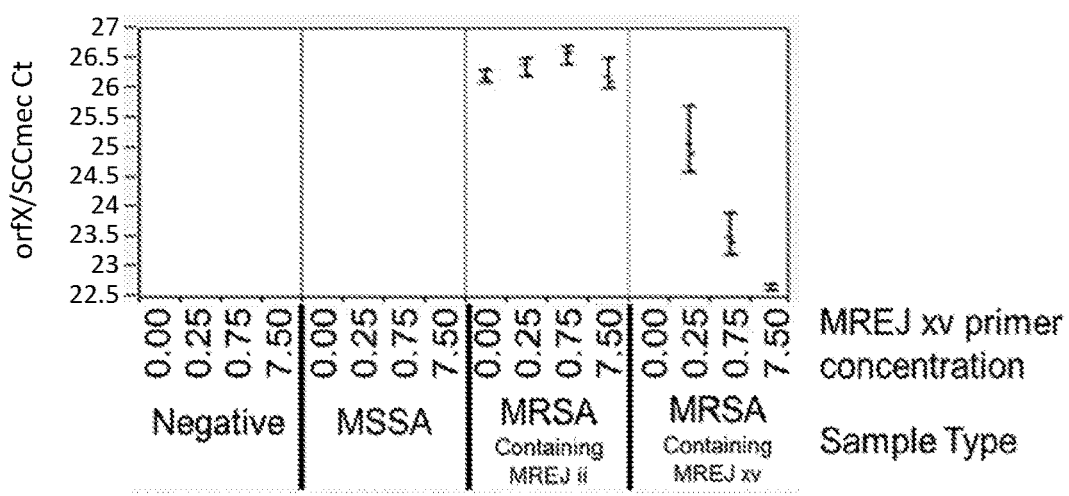

Inclusion of an MREJ xv amplification oligomer (SEQ ID NO: 83 and 84) configured to hybridize to sites in multiple MREJ xv sequences (encompassing position 491 of SEQ ID NO: 17 and position 555 of SEQ ID NO: 18) was tested for any potential impact on the amplification and detection of samples of methicillin-susceptible *Staphylococcus aureus* (MSSA), non-MREJ-xv MRSA (i.e., containing the MREJ ii sequence), or MRSA containing the MREJ xv sequence (FIGS. 1A-1B). Amplification was done on ABI 7500 Fast™. Negative samples indicate samples containing no *Staphylococcus* DNA. Reactions with each sample were done with 0, 0.25, 0.75, or 7.50 µM concentration of MREJ xv primer.

FIG. 1A is a pseudogel image generated with the Agilent Tape Station and shows that MREJ ii, MREJ xv, GAPDH, and mecA were all amplified as would be expected in the presence of MREJ xv primer, even at the highest concentration of this primer. Amplification of the orfX/SCCmec junction amplicon was also measured in terms of Ct (orfX/SCCmec threshold cycle [Ct]) for each sample (FIG. 1B). While the detection of MREJ ii, GAPDH (data not shown), and mecA (data not shown) did not appear to be affected by the concentration of MREJ xv primer included in the reaction, the signal for MREJ xv increased as would be expected with increased concentrations of the MREJ xv primer.

Example 2. Performance Testing of MREJ xv Strain Detection

The combination of oligomers as in Example 1 was tested for detection of a variety of different MRSA clones containing the MREJ xv sequence and compared to other commercially available MRSA tests. Clinical isolates obtained from laboratories in Denmark (M42885 and M4374), France (BL74), and Australia (all other clones listed in FIG. 2) were sequenced to confirm the presence of an MREJ type xv sequence prior to testing with each molecular test. MRSA clinical isolates were then diluted in liquid Amies transport medium, and multiple aliquots were made. Matched aliquots of each clinical isolate were sent for testing with Cepheid™ Xpert® SA Nasal Complete and Becton Dickinson Max Staph SR™. Comparative tests were performed with the versions of Cepheid Xpert MRSA and Becton Dickinson Max Staph SR commercially available on or about May 12, 2017.

Testing with oligomers according to this disclosure was done with MRSA clinical isolates at 1,000 colony-forming units (CFU)/mL, and Cepheid testing was done at 10,000 CFU/mL or higher.

While all listed MREJ xv-containing isolates were detected by oligomers according to this disclosure including the MREJ type xv oligomer described in Example 1 (as indicated by a positive orfX/SCCmec value), Cepheid testing generated false negatives for 7/11 tested isolates (as indicated by a Ct Value of 0.0 or Ct values greater than 38 for SCC) (FIG. 2). A formulation of oligomers according to this disclosure without the MREJ type xv oligomer also did not detect orfX/SCCmec in any of these clinical isolates (data not shown), confirming the efficacy of this oligomer for detecting MRSA containing an MREJ type xv sequence.

A value of zero (0.0) or a value of 38 or higher for SCC in the Cepheid assay indicates that the assay results would have been interpreted as negative for MRSA, based on an apparent absence of the SCC sequence. All Cepheid results for these isolates were positive for mec and SPA (gene encoding Protein A of *Staphylococcus aureus*). For the isolates with a zero value or a value greater than 38 for SCC, these results would have led to a false-negative result indicating the presence of *Staphylococcus aureus* that did not contain a SCC junction sequence (i.e., MSSA), instead of the correct result of an MRSA strain.

The BD Max™ Staph SR assay run under manufacturer's conditions also missed 4/4 strains that were tested at 10,000 CFU/mL (data not shown). These data suggest that the BD Max™ Staph SR assay is not designed to detect MREJ xv.

Thus, the oligomers according to this disclosure with inclusion of MREJ xv primer appeared to be more sensitive for detection of strains containing the MREJ xv sequence compared to the Cepheid and BD assays tested.

Example 3. Limit of Detection Analysis

The functionality of nine orfX/SCCmec junction systems were tested on plasmid targets to assess performance. Analytical sensitivity testing of the various systems indicated a LoD between 88 and 223.6 copies/mL. Results for each plasmid tested are shown in Table E.

TABLE E

Plasmid LoD testing results

| Plasmid | LoD (copies/mL) | Lower 95% CI (copies/mL) | Upper 95% CI (copies/mL) |
| --- | --- | --- | --- |
| MREJ i | 132.7 | 99.6 | 209.7 |
| MREJ ii | 146.6 | 112.5 | 219.0 |
| MREJ iii | 88.0 | 68.3 | 136.9 |
| MREJ iv | 173.2 | 140.3 | 232.7 |
| MREJ v | 171.5 | 133.3 | 249.0 |
| MREJ vi | 184.9 | 144.2 | 266.4 |
| MREJ vii | 223.6 | 172.0 | 333.4 |
| MREJ xii | 145.8 | 111.7 | 218.5 |
| MREJ xiii | 205.1 | 162.5 | 287.8 |
| MREJ xxi | 178.1 | 139.7 | 253.7 |

A panel of MRSA isolates containing MREJ types ii, xii, xv, and xxi were tested to evaluate the LoD (FIG. 3). The testing panel included GP1822 (MREJ ii, SCCmec II), GP1826 (MREJ xii, SCCmec V), GP1827 (MREJ xxi, SCCmec XI), and CI5708 (MREJ xv, SCCmec V). A negative control containing only internal control plasmid was also included (data not shown).

The positivity was measured for the assay. These results indicated that MRSA nucleic acid from clinical isolates was detected robustly down to about 500 CFU/mL or less.

Example 4. Co-Infection Testing

Figure 4:
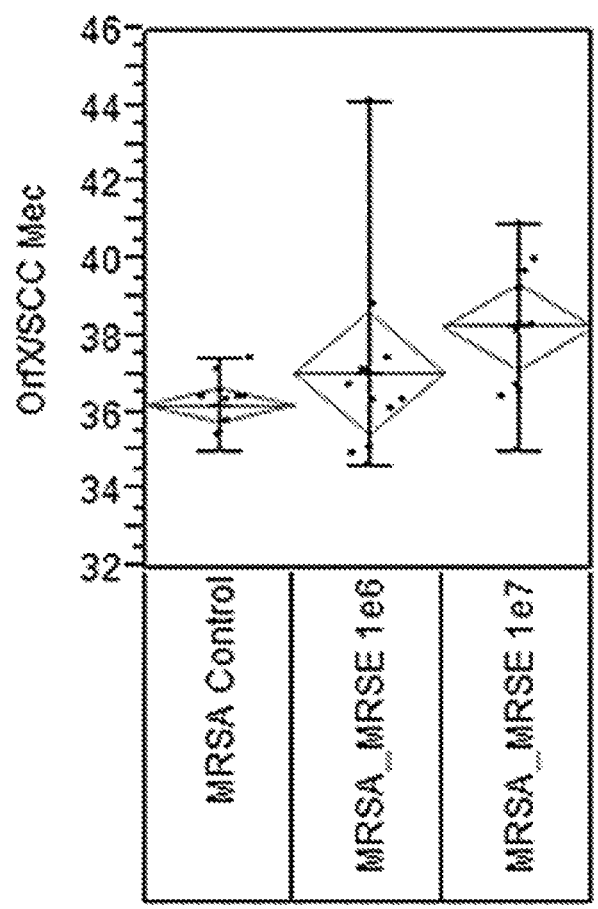
FIG. 4 shows detection in MRSA/MRSE (Methicillin-Resistant *Staphylococcus epidermidis*) co-infection samples for the MRSA assay. Data are presented as non-normalized average Ct values of orfX/SCCmec target detection.

Detection of MRSA was tested in a model of co-infection with excess methicillin-resistant *Staphylococcus epidermidis* (MRSE). In the specific model tested, MRSA (GP1822) was present at 10' CFU/mL, either alone (MRSA Control); with MRSE at $10^6$ CFU/mL (MRSA_MRSE 1e6); or with MRSE at 107 CFU/mL (MRSA_MRSE 1e7) (FIG. 4). Results showed no loss in detection under any condition, with positivity seen in 12/12 samples tested. Thus, the assay was able to detect MRSA in the presence of 1,000-fold and 10,000-fold excesses of MRSE.

Example 5. Cross-Reactivity

The cross-reactivity of the MRSA assay was tested as described in Example 1.

A series of seven cross-reactivity panels were tested that collectively included *S. capitis*, *S. caprae*, *S. epidermidis* (MSSE), *S. epidermidis* (MRSE), *S. delphini*, *S. haemolyticus*, *S. hominis*, *S. intermedius*, *S. lutrae*, *S. pseudointermedius*, *S. saprophiticus*, *S. schiefen*, *S. simulans*, *S. warneri*, *S. xylosus*, and *S. pasteuri*. MRSE was present in panels 2 and 6.

Positive results were found for MRSA only in the positive control and not with other cross-reactivity panels (FIG. 5). For other markers, Panel 2 and Panel 6 were positive for mecA/C, due to the presence of a mec gene from MRSE. GAPDH is a highly conserved sequence present in and indicative of or specific to *Staphylococcus aureus*, and a lack of GAPDH positivity in cross-reactivity panels indicates the specificity of the assay. All reactions were positive for the internal control (IC).

Thus, the assay was specific for MRSA over other *Staphylococcus* species tested herein.

Example 6. Detection of mecA and mecC

A mecA/mecC amplification oligomer configured to specifically hybridize to a site comprising position 1394 of SEQ ID NO: 13 and position 1285 of SEQ ID NO: 14 and a mecA/mecC amplification oligomer configured to specifically hybridize to a site comprising position 1312 of SEQ ID NO: 13 and position 1203 of SEQ ID NO: 14 were used together with primary detection oligomers specific for mecA and mecC and a secondary detection oligomer (FRET cassette) configured to interact with the cleaved flap of either primary detection oligomer generated through INVADER PLUS chemistry.

Analytical sensitivity was determined with plasmid targets. Results are shown in Table F.

TABLE F mecA and mecC plasmid LoD testing results

| Plasmid | LoD (copies/mL) | Lower 95% CI (copies/mL) | Upper 95% CI (copies/mL) |
|---|---|---|---|
| mecA | 413.9 | 295.1 | 732.3 |
| mecC | 159.1 | 123.1 | 232.7 |

The mecA and mecC amplification oligomers and detection oligomers were present in the experiments described in Examples 1-5 and did not interfere with orfX/SCCmec junction detection or result in any non-specific signal generation.

Example 7. Detection of *S. aureus* GAPDH

A first GAPDH amplification oligomer configured to specifically hybridize to a site comprising position 212 of SEQ ID NO: 15 and a second GAPDH amplification oligomer configured to specifically hybridize to a site comprising position 312 of SEQ ID NO: 15 were used to detect *S. aureus* GAPDH together with appropriate primary and secondary detection oligomers by INVADER PLUS chemistry. Analytical sensitivity was determined with a plasmid target. Results are shown in Table G.

TABLE G

GAPDH plasmid LoD testing results

| Plasmid | LoD (copies/mL) | Lower 95% CI (copies/mL) | Upper 95% CI (copies/mL) |
|---|---|---|---|
| GAPDH | 191.4 | 146.4 | 287.3 |

The GAPDH amplification oligomers were present in the experiments described in Examples 1-6 and did not interfere with orfX/SCCmec junction or mecA/C detection or result in any non-specific signal generation, and did not result in any SA false positives (e.g., no GAPDH signal was generated in any of the non-*S. aureus* species listed) in Example 5.

An earlier design of the second GAPDH amplification oligomer resulted in false-positive orfX/SCCmec junction signal in the presence of high levels of orfX target sequence (e.g., from MSSA) due to a false priming event (data not shown). Redesigning this oligomer to hybridize to a site comprising position 312 of SEQ ID NO: 15 (e.g., positions 299-325 of SEQ ID NO: 15) eliminated the false priming issue.

TABLE OF SEQUENCES

| SEQ ID NO | Description | Sequence[1] 5'→3' |
|---|---|---|
| 1 | Exemplary MREJ i sequence | TACATTAGAAATACAAGGAAAGATGCTATCTTCCGAAGGATT GGCCCAAGAATTGAACCAACGCATGACCCAAGGGCAAAGCGA CTTTGTTTTCGTCATTGGCGGATCAAACGGCCTGCACAAGGA CGTCTTACAACGCAGTAACTACGCACTATCATTCAGCAAAAT GACATTCCCACATCAAATGATGCGGGTTGTGTTAATTGAACA AGTGTACAGAGCATTTAAGATTATGCGAGGAGAAGCTTATCA TAAGTAATGAGGTTCATGATTTTTGACATAGTTAGCCTCCGC AGTCTTTCATTTCAAGTAAATAATAGCGAAATATTCTTTATA CTGAATACTTATAGTGAAGCAAAGTTCTAGCTTTGAGAAAAT TCTTTCTGCAACTAAATATAGTAAATTACGGTAAAATATAAA TAAGTACATATTGAAGAAAATGAGACATAATATATTTTATAA TAGGAGGGAATTTCAAATGATAGACAACTTTATGCAGGTCCT TAAATTAATTAAAGAGAAACGTACCAATAATGTAGTTAAAAA ATCTGATTGGGATAAAGGTGATCTATATAAAACTTTAGTCCA TGATAAGTTACCCAAGCAGTTAAAAGTGCATATAAAAGAAGA TAAATATTCAGTTGTAGGGAAGGTTGCTACTGGGAACTATAG TAAAGTTCCTTGGATTTCAATATATGATGAGAATATA |
| 2 | Exemplary MREJ ii sequence | TAAATGTCAGGAAAATATCAAAAACTGCAAAAAATATTGGTA TAATAAGAGGGAACAGTGTGAACAAGTTAATAACTTGTGGAT AACTGGAAAGTTGATAACAATTTGGAGGACCAAACGACATGA AAATCACCATTTTAGCTGTAGGGAAACTAAAAGAGAAATATT GGAAGCAAGCCATAGCAGAATATGAAAAACGTTTAGGCCCAT ACACCAAGATAGACATCATAGAAGTTCCAGACGAAAAAGCAC CAGAAAATATGAGCGACAAAGAAATTGAGCAAGTAAAAGAAA AAGAAGGCCAACGAATACTAGCCAAAATTAAACCACAATCCA CAGTCATTACATTAGAAATACAAGGAAAGATGCTATCTTCCG AAGGATTGGCCCAAGAATTGAACCAACGCATGACCCAAGGGC AAAGCGACTTTGTATTCGTCATTGGCGGATCAAACGGCCTGC ACAAGGACGTCTTACAACGCAGTAACTACGCACTATCATTCA GCAAAATGACATTCCCACATCAAATGATGCGGGTTGTGTTAA TTGAGCAAGTGTATAGAGCATTTAAGATTATGCGTGGAGAAG |

-continued

| TABLE OF SEQUENCES | | |
|---|---|---|
| SEQ ID NO | Description | Sequence¹ 5'→3' |
| | | CATATCATAAATGATGCGGTTTTTTCAGCCGCTTCATAAAGG GATTTTGAATGTATCAGAACATATGAGGTTTATGTGAATTGC TGTTATGTTTTTAAGAAGCTTATCATAAGTAATGAGGTTCAT GATTTTTGACATAGTTAGCCTCCGCAGTCTTTCATTTCAAGT AAATAATAGCGAAATATTCTTTATACTGAATACTTATAGTGA AGCAAAGTTCTAGCTTTGAGAAAATTCTTTCTGCAACTAAAT ATAGTAAATTACGGTAAAATATAAATAAGTACATATTGAAGA AAATGAGACATAATATATTTTATAATAGGAGGGAATTTCAAA TGATAGACAACTTTATGCAGGTCCTTAAATTAATTAAAGAGA AACGTACCAATAAT |
| 3 | Exemplary MREJ iii sequence | CAATGCCCACAGAGTTATCCACAAATACACAGGTTATACACT AAAAATTGGGCATGAATGTCAGAAAAATATCAAAAACTGCAA AGAATATTGGTATAATAAGAGGGAACAGTGTGAACAAGTTAA TAACTTGTGGATAACTGGAAAGTTGATAACAATTTGGAGGAC CAAACGACATGAAAATCACCCATTTTAGCTGTAGGGAAACTAA AAGAGAAATATTGGAAGCAAGCCATAGCAGAATATGAAAAAC GTTTAGGCCCATACACCAAGATAGACATCATAGAAGTTCCAG ACGAAAAGCACCAGAAAATATGAGCGACAAAGAAATTGAGC AAGTAAAAGAAAAAGAAGGCCAACGAATACTAGCCAAAATCA AACCACAATCAACAGTCATTACATTAGAAATACAAGGAAAGA TGCTATCTTCCGAAGGATTGGCCCAAGAATTGAACCAACGCA TGACCCAAGGGCAAAGCGACTTTGTATTCGTCATTGGCGGAT CAAACGGCCTGCACAAGGACGTCTTACAACGCAGTAACTACG CACTATCATTCAGCAAAATGACATTCCCACATCAAATGATGC GGGTTGTGTTAATTGAACAAGTGTACAGAGCATTTAAGATTA TGCGTGGAGAAGCGTATCATAAATAAAACTAAAAATTAGGTT GTGTATAATTTAAAAATTTAATGAGATGTGGAGGAATTACAT ATATGAAATATTGGATTATACCTTGCAATATCATACGATGTT TATAGAGTGTTTAATAAACCATTTTT |
| 4 | Exemplary MREJ iv sequence | CTGTAGGGAAACTAAAAGAGAAATACTGGAAGCAAGCCATAG CAGAATATGAAAAACGTTTAGGCCCATACACCAAGATAGACA TCATAGAAGTTCCAGACGAAAAGCACCAGAAAATATGAGCG ACAAAGAAATCGAGCAAGTAAAAGAAAAAGAAGGCCAACGAA TACTAGCCAAAATCAAACCACAATCCACAGTCATTACATTAG AAATACAAGGAAAGATGCTATCTTCCGAAGGATTGGCCCAAG AATTGAACCAACGCATGACCCAAGGGCAAAGCGACTTTGTAT TCGTCATTGGCGGATCAAACGGCCTGCACAAGGACGTCTTAC AACGCAGTAACTACGCACTATCATTCAGCAAAATGACATTCC CACATCAAATGATGCGGGTTGTGTTAATTGAACAAGTGTACA GAGCATTTAAGATTATGCGTGGAGAAGCGTACCACAAATGAT GCGGTTTTTTATCCAGTTTTTTGTTTAATGAACAAGGTAAAT TACGAGATAATATTTGAAGAAAACAATAAAGTAGAGATGGAT TTCCATATCCTCTTTAGTAGCGGTTTTTATCTGTAAGGTTTA TTAATAATTAAATAAATAGGCGGGATAGTTATATATAGCTTA TTAATGAAAGAATATGATTATTAATTTAGTATTATATTTTAA TATTAAAAAGAAGATATGAAATAATTATTCATACCTTCCACC TTACAATAATTAGTTTTCAATCGAATATTAAGATTATTAGTA GTCTTAAAAGTTAAGACTTCCTTATATTAATGACCTAATTTA TTATTTGCCTCATGAATTATCTTTTTATTTCTTTGATATGTC CCAAACCACATCGTGATATACACTACAATAAATATTATGATG AAACTAATAATATTCTCAAAGTTCAGATGGAACCAACCTGCT AGAATAGCGAGTGGGAAGAATAGGATTATCATCAATATAAAG TGAACTACAGTCTGTTTTGTTATACTCCAATCGGTATCTGTA AATATCAAATTACCATAAGTAAACAAAATTCCAATCAATGCC CATAGTGCTACACATATTAGCATAATAACCGCTTCATTAAAG TTTTCATAATAAATTTTACCCATAAAAGAATCTGGATATAGT GGTACATATTTATCCCTTGAAAAAAATAAGTGAAGTAATGAC AGAAATCATAAGACCAGTGAACGCACCTTTTTGAACAGCGTG GAATAATTTTTTCATAGTGAGATGGACCATTCCATTTGTTTC TAACTTCAAGTGATCAATGTAATTTAGATTGATAATTTCTGA TTTTGAAATACGCACGAATATTGAACCGACAAGCTCTTCAAT TTGGTAAAGTCGCTGATAAAGTTTTAAAGCTTTATTATTCAT TGTTATCGCATACCTGTTTATCTTCTACTATGAACTGTGCAA TTTGTTCTAGATCAATTGGGTAAACATGATGGTTCTGTTGCA AAGTAAAAAAATATAGCTAAACACTAATTTATCATGTCAGTG TTCGCTTAACTTGCTAGCATGATGCTAATTTCGTGGCATGGC GAAAATCCGTAGATCTGATGAGACCTGCGGTTCTTTTTATAT AGAGCGTAAATACATTCAATACCTTTTAAAGTATTCTTTGCT GTATTGACTTTGATACCTTGTCTTTCTTACTTTAATATGA CGGTGATCTTGCTCAATGAGGTTATTCAAATATTTCGATGTA CAATGACAGTCAGGTTTAAGTTTAAAAGCTTTAATTACTTTA |

| TABLE OF SEQUENCES | | |
|---|---|---|
| SEQ ID NO | Description | Sequence¹ 5'→3' |
| | | GCCATTGCTACCTTCGTTGAAGGTGCCTGATCTGTAATTACC TTTTGAGGTTTACCAAATTGTTTAATGAGACGTTTAATAAAC GCATATGCTGAATGATTATCTCGTTGCTTACGCAACCAAATA TCTAATGTATGTCCCTCTGCATCAATGGCACGATATAAATAG CTCCATTTTCCTTTTATTTTGATGTACGTCTCATCAATACGC CATTTGTAATAAGCTTTTTTATGCTTTTTCTTCCAAATTTGA TATAAAATTGGGGCATATTCTTGAACCCAACGGTAGACCGTT GAATGATGAACGTTTACACCACGTCCCCTTAATATTTCAGAT ATATCACGATAACTCAATGCATATCTTAGATAGTAGCCAACG GCTACAGTGAT |
| 5 | Exemplary MREJ v sequence | AAAGAGAAATATTGGAAGCAAGCCATAGCAGAATATGAAAAA CGTTTAGGCCCATACACCAAGATAGACATCATAGAAGTTCCA GACGAAAAAGCACCAGAAAATATGAGTGACAAAGAAATTGAG CAAGTAAAAGAAAAAGAAGGCCAACGAATACTAGCCAAAATC AAACCACACTCCACAGTCATTACATTAGAAATACAAGGAAAG ATGCTATCTTCCGAAGGATTGGCCCAAGAATTGAACCAACGC ATGACCCAAGGGCAAAGCGACTTTGTTTTCGTCATTGGCGGA TCAAACGGCCTGCACAAGGACGTCTTACAACGCAGTAACTAC GCACTATCATTCAGCAAAATGACATTCCCACATCAAATGATG CGGGTTGTGTTAATTGAACAAGTGTACAGAGCATTTAAGATT ATGCGAGGAGAAGCATATCATAAATGATGCGGTTATTTCAGC CGTAATTTTATAATATAAAGCAGAGTTTATTAAATTTTAATG ATTACTTTTTATTAAGAATTAATTCTAGTTGATATATTATAA TGTGAAACACAAAATAATAATTTGTAATTGTTAGTTTATAGG CATCTGTATTTGGAATTTTTTGTAGACTATTTAAAAAATAGT CGTTCATCAAGTATAAGGATGTAGAGATTTGTTGGATAATTT CTTCGGATGTTTTAAAATTATCATTAAATTAGATGGTATCT GATCTTGAGTTTTGTTTTAGTGTATGTATATTTTAAAAAAT TTTTGATTGTTGTTATTTGACTCTCTTTTAATTTGACACCCT CATCAATAAATGTGTTAAATATATCTTCATTTGTACTTAAAT CATCAAAATTTGCCAACAAATATTTGAACGTCTCTAAATCAT TATGTTTGAGTTCCGTTTTGCTATTCCATAATTCCAAACCAT TTGGTAGAAAGCCCAAGCTGTGATTTTGATCTCCCCATATAG CTGAATTTAAATCAGTGAGTTGATTAATTTTTTCAACACAGA AATGTAATTTTGGAATGAGGAATCGAAGTTGTTCTTCTACTT GCTGTACTTTTCTTTTGTTTTCAATAAAATTTCTACACCATA CTGTTATCAAACCGCCAATTATTGTGCACAATCCTCCAATGA TTGTAGATAAAATTGACAATATATTACACACCTTTCTTAGAG GTTTATTAACATCTATTTTTGAATTTAAAATTATTACTTTGG TAGCGTTATAACCTATTTAACAGATTAGAGAAAAATTGAATG ATCGATTGAAGAATTTCCAAAATACCGTCCCATATGCGTTGA AGGAGATTCTATTTTCTTCTGTATTCAAATCTTTGGCTTTA TCCTTTGCTTTATTCAATAAATCATCTGAGTTTTTTCAATA TTTTTTAATACATCTTTGGCATTTTGTTTAAATACTTTAGGA TCGGAAGTTAGGGCATTAGAGTTTGCCACATTAATCATATTA TTATTAATCATTTGAATTTGATTATCTGATAATATCTCTGAT AACCTACGCTCATCGAGGACTTTATTAACAGTGTCTTCAACT TGTTGTTGTGTGATTTGTTTATCTTGATTTTGTTTAATATCT GCAAGTTGTTCTTTAATATCTGCTATAGAAGCATTTAAAGCT TCATCTGAATACCCAT |
| 6 | Exemplary MREJ vi sequence | ACCATTTTAGCTGTAGGGAAACTAAAAGAGAAATACTGGAAG CAAGCCATAGCAGAATATGAAAAACGTTTAGGCCCATACACC AAGATAGACATCATAGAAGTTCCAGACGAAAAAGCACCAGAA AATATGAACTACAAAGAAATTGAGCAAGTAAAAGAAAAAGAA GGCCAACGAATACTAGCCAAAATCAAACCACACAATCAACAGTC ATTACATTAGAAATACAAGGAAAGATGCTATCTTCCGAAGGA TTGGCCCAAGAATTGAACCAACGCATGACCCAAGGGCAAAGC GACTTTGTATTCGTCATTGGCGGATCAAACGGCCTGCACAAG GACGTCTTACAACGCAGTAACTACGCACTATCATTCAGCAAA ATGACATTCCCACATCAAATGATGCGGGTTGTGTTAATTGAA CAAGTGTACAGAGCATTTAAGATTATGCGAGGAGAAGCGTAT CATAAGTGATGGTAAAAAATATGAGTAAGTAGATGAAGAGTG AAAATCAGATTAATTAATAATAATGTATCAAATTTAAATAAA GGGGTTTTTAAGTATGAATTTAAGAGGTCATGAAAATAGACT TAAATTTCATGCGAAATATGATGTGACACCTATATCACATTT AAAATTATTAGAAGGTCAAAAGAAAGACGGTGAAGGCGGCAT ACTGACAGATAGCTATTACTGTTTTTCATACAGCTTAAAAGG TAATTCTAAAAAGTTTTAGGTACGTTTAATTGTGGTTATCA TATTGCTGAAGATTTACTAAAATTATCAAATCAAGATAAATT ACCTTTATTTAACCCGTTTAAAGTAATTAATGAAGGTAATCA ATTGCAGGGCGTAACGAATAAAGGTAATTTAAATATTAATAG |

| TABLE OF SEQUENCES | | |
|---|---|---|
| SEQ ID NO | Description | Sequence¹ 5'→3' |
| | | GCAAAGAAAACAGTATAATGAAGTGGCTTTACAGCTTTCAAA TGCTATTAATTTAATCATAATTTGTTATGAGGATAATATTAA AGAACCACTTTCAACGATAAAATAC |
| 7 | Exemplary MREJ vii sequence | ACCATTTTAGCTGTAGGGAAACTAAAAGAGAAATATTGGAAG CAAGCCATAGCAGAATATGAAAAACGTTTAGGCCCATACACC AAGATAGACATCATAGAAGTTCCAGACGAAAAAGCACCAGAA AATATGAGCGACAAAGAAATTGAGCAAGTAAAAGAAAAAGAA GGCCAACGAATACTAGCCAAAATCAAACCACAATCCACAGTC ATTACATTAGAAATACAAGGAAAGATGCTATCTTCCGAAGGA TTGGCCCAAGAATTGAACCAACGCATGACCCAAGGGCAAAGC GACTTTGTATTCGTCATTGGCGGATCAAACGGCCTGCACAAG GACGTCTTACAACGCAGTAACTATGCACTATCATTTAGCAAA ATGACATTCCCACATCAAATGATGCGGGTTGTGTTAATTGAA CAAGTGTATAGAGCATTTAAGATTATGCGTGGAGAAGCGTAC CACAAATAAAACTAAAAAATATGAGAAAATTATTAAATTAGC TCAAATCTTTGAAGAATAAAAAGTGAATATTAAGTTTGATAA TTTAGGTACAAGTAAAGATTAAGAATTTCCATTATTTAATAC ATGGTGTGTAAATCGACTTCTTTTTGTATTAGATGTTTGCAG TAAGCGATGTAAAGAAGATGCTAATAAATATGTGAGGAATGA TTACGATACTAGATAAGCGGCTAATGAAATTTTTTAAAGTAC ATATATAGACATATTTTTCATTTAGTAAAATTTTGAATTTCA CTTTGCTAAGACTAGTGTCTAGAAATTTATAATGATTTATTA ACACCTATTTGAAACTTAAGTATAATAAATGATTCGGATTTT ATTTTTAATAAAGACAAACTTGAACGTAGCAAAGTAGTTTTT ATGATAAATAATAAGTTTTAATAATGTGACGCTTTTATATAA GCACATTATTATGAACAATGTGAATTGAGCATCTACAATTAC ATTAATAAATATATAAATGATGATTTAAATTCACATATATTT ATAATACACATACTATATGAAAGTTTTGATTATCCGAATAAA TGCTAAAATTAATAAAATAATTAAAGGAATCATACTTATTAT ACGTATACGTTTAGCT |
| 8 | Exemplary MREJ ix sequence | GCTGTAGGGAAACTAAAAGAGAAATATTGGAAGCAAGCCATA GCAGAATATGAAAAACGTTTAGGCCCATACACCAAGATAGAC ATCATAGAAGTTCCAGACGAAAAAGCACCAGAAAATATGAGC GACAAAGAAATTGAGCAAGTAAAAGAAAAAGAAGGCCAACGA ATACTAGCCAAAATTAAACCACAATCCACAGTCATTACATTA GAAATACAAGGAAAGATGCTATCTTCCGAAGGATTGGCCCAA GAATTGAACCAACGCATGACCCAAGGGCAAAGCGACTTTGTA TTCGTCATTGGCGGATCAAACGGCCTGCACAAGGACGTCTTA CAACGCAGTAACTACGCACTATCATTCAGCAAAATGACATTC CCACATCAAATGATGCGGGTTGTGTTAATTGAGCAAGTGTAT AGAGCATTTAAGATTATGCGTGGAGAAGCATATCATAAATGA TGCGGTTTTTTCAGCCGCTTCATAAAGGGATTTTGAATGTAT CAGAACATATGAGGTTTATGTGAATTGCTGTTATGTTTTTAA GAAGCATATCATAAGTGATGCGGTTTTTATTAATTAGTTGCT AAAAAATGAAGTATGCAATATTAATTATTATTAAATTTTGAT ATATTTAAAGAAAGATTAAGTTTAGGGTGAATGAATGGCTTA TCAAAGTGAATATGCATTAGAAAATGAAGTACTTCAACAACT TGAGGAATTGAACTATGAAAGAGTAAATATACATAATATTAA ATTAGAAATTAATGAATATCTCAAAGAACTAGGAGTGTTGAA AAATGAATAAGCAGACAAATACTCCAGAACTAAGATTTCCAG AGTTTGATGAGGAATGGAAAAAAAGGAAATTAGGTGAAGTAG TAAATTATAAAAATGGTGGTTCATTTGAAAGTTTAGTGAAAA ACCATGGTGTATATAAACTCATAACTCTTAAATCTGTTAATA CAGAAGGAAAGTTGTGTAATTCTGGAAAATATATCGATGATA AATGTGTTGAAACATTGTGTAATGATACTTTAGTAATGATAC TGAGCGAGCAAGCACCAGGACTAGTTGGAATGACTGCAATTA TACCTAATAATAATGAGTATGTACTAAATCAACGAGTAGCAG CACTAGTGCCTAAACAATTTATAGATAGTCAATTTCTATCTA AGTTAATTAATAGAAACCAGAAATATTTCAGTGTGAGATCTG CTGGAACAAAAGTGAAAAATATTTCTAAAGGACATGTA |
| 9 | Exemplary MREJ xii sequence | ACCATTTTAGCTGTAGGGAAACTAAAAGAGAAATATTGGAAG CAAGCCATAGCAGAATATGAAAAACGTTTAGGCCCATACACC AAGATAGACATCATAGAAGTTCCAGACGAAAAAGCACCAGAA AATATGAGCGACAAAGAAATTGAGCAAGTAAAAGAAAAAGAA GGCCAACGAATACTAGCCAAAATCAAACCACAATCCACAGTC ATTACATTAGAAATACAAGGAAAGATGCTATCTTCCGAAGGA TTGGCCCAAGAATTGAACCAACGCATGACCCAAGGGCAAAGC GACTTTGTATTCGTCATTGGCGGATCAAACGGCCTGCACAAG GACGTCTTACAACGCAGTAACTATGCACTATCATTTAGCAAA ATGACATTCCCACATCAAATGATGCGGGTTGTGTTAATTGAA |

| TABLE OF SEQUENCES | | |
|---|---|---|
| SEQ ID NO | Description | Sequence 5'→3' |
| | | CAAGTGTATAGAGCATTTAAGATTATGCGTGGAGAGGCGTAT<br>CATAAATAAAACTAAAAAACGGATTGTGTATAATATATTTTA<br>AATATAAAAAGGATTGATTTTATGTTAAATAAATTAGAAAAT<br>GTTAGTTATAAATCATTCGATAATTACACTAGTGAAGATGAT<br>TTGACTAAAGTAAATATATTTTTTGGAAGAAATGGGAGTGGA<br>AAAAGCTCATTAAGTGAATGGTTAAGAAGACTAGATAATGAA<br>AAAAGTGTTATCTTTAATACTGGTTACTTAAAAAATAATATT<br>GAAGAAGTTGAAGAAATAGATGGTGTGAATTTGGTTATTGGA<br>GAAGAATCTATAAATCATAGTGACCAAATTAAGCATTTAAAT<br>AGCGCTATAAATAGTTTAGAAAATTTTATTACTCGGAAAAAT<br>AGTGAACTTAAGCATTCAAAAGAAAGAATTTACAATAAAATG<br>AATATCAGACTAAATGAAGCTAGAGAAAGATTTGAAATAGGT<br>AGTAATGTGGTTAAGCAGAAGAGGAATGCTGACAAAGATCCA<br>GTTAATGCTTTTTATAGTTGGAAGAAAAATGCTAACGATATA<br>ATTCAAGAGATGACTATTGAATCTTTAGATGAATTAGAAGAA<br>AGAATAACAAGAAAAGAAGTCTTATTAAATAATATAAAAACA<br>CCAATTTTAGCTTTTGATTATAATGATTTTAGT |
| 10 | Exemplary MREJ xiii sequence | ACCATTTTAGCTGTAGGGAAACTAAAAGAGAAATATTGGAAG<br>CAAGCCATAGCAGAATATGAAAAACGTTTAGGCCCATACACC<br>AAGATAGACATCATAGAAGTTCCAGACGAAAAAGCACCAGAA<br>AATATGAGCGACAAAGAAATTGAGCAAGTAAAAGAAAAAGAA<br>GGCCAACGAATACTAGCCAAAATTAAACCACAATCCACAGTC<br>ATTACATTAGAAATACAAGGAAAGATGCTATCTTCCGAAGGA<br>TTGGCCCAAGAATTGAACCAACGCATGACCCAAGGGCAAAGC<br>GACTTTGTATTCGTCATTGGCGGATCAAACGGCCTGCACAAG<br>GACGTCTTACAACGCAGTAACTACGCACTATCATTCAGCAAA<br>ATGACATTCCCACATCAAATGATGCGGGTTGTGTTAATTGAG<br>CAAGTGTATAGAGCATTTAAGATTATGCGTGGAGAAGCATAT<br>CATAAGTGATGCGGTTTTTATTAATTAGTTGCTAAAAAATGA<br>AGTATGCAATATTAATTATTATTAAATTTTGATATATTTAAA<br>GAAAGATTAAGTTTAGGGTGAATGAATGGCTTATCAAAGTGA<br>ATATGCATTAGAAAATGAAGTACTTCAACAACTTGAGGAATT<br>GAACTATGAAAGAGTAAATATACATAATATTAAATTAGAAAT<br>TAATGAATATCTCAAAGAACTAGGAGTGTTGAAAAATGAATA<br>AGCAGACAAATACTCCAGAACTAAGATTTCCAGAGTTTGATG<br>AGGAATGGAAAAAAAGGAAATTAGGTGAAGTAGTAAATTATA<br>AAAATGGTGGTTCATTTGAAAGTTTAGTGAAAAACCATGGTG<br>TATATAAACTCATAACTCTTAAATCTGTTAATACAGAAGGAA<br>AGTTGTGTAATTCTGGAAAATATATCGATGATAAATGTGTTG<br>AAACATTGTGTAATGATACTTTAGTAATGATACTGAGCGAGC<br>AAGCACCAGGACTAGTTGGAATGACTGCAATTATACCTAATA<br>ATAATGAGTATGTACTAAATCAACGAGTAGCAGCACTAGTGC<br>CTAAACAATTTATAGATAGTCAATTTCTATCTAAGTTAATTA<br>ATAGAAACCAGAAATATTTCAGTGTGAGATCTGCTGGAACAA<br>AAGTGAAAATATTTCTAAAGGACATGTAGAAAACTTTAATT<br>TTTTATCTCCTAATTACACTGAACAACAAAAATAGGTAATT<br>TCTTCAGCAAACTCGACCGCCAGATTGAGTTAGAAGAAGAGA<br>AACTTGAACTCTTAGAGCAACAAAAGCGTGGATATATTCAGA<br>AGATTTTTTCTCAAGATTTAAGATTTAAAGATGAAAATGGAA<br>ACAGTTATCCTGATTGGTCTATTAAAAAGATTGAAG<br>ACCATTTTAGCTGTAGGGAAACTAAAAGAGAAATATTGGAAG |
| 11 | Exemplary MREJ xiv sequence | CAAGCCATAGCAGAATATGAAAAACGTTTAGGCCCATACACC<br>AAGATAGACATCATAGAAGTTCCAGACGAAAAAGCACCAGAA<br>AATATGAGCGACAAAGAAATTGAGCAAGTAAAAGAAAAAGAA<br>GGCCAACGAATACTAGCCAAAATTAAACCACAATCCACAGTC<br>ATTACATTAGAAATACAAGGAAAGATGCTATCTTCCGAAGGA<br>TTGGCCCAAGAATTGAACCAACGCATGACCCAAGGGCAAAGC<br>GACTTTGTATTCGTCATTGGCGGATCAAACGGCCTGCACAAG<br>GACGTCTTACAACGCAGTAACTACGCACTATCATTCAGCAAA<br>ATGACATTCCCACATCAAATGATGCGGGTTGTGTTAATTGAG<br>CAAGTGTATAGAGCATTTAAGATTATGCGTGGAGAAGCATAT<br>CATAAATGATGCGGTTTTTCAGCCGCTTCATAAAGGGATTT<br>TGAATGTATCAGAACATATGAGGTTTATGTGAATTGCTGTTA<br>TGTTTTAAGAAGCATATCATAAATGATGCGGTTTTTTCAGC<br>CGCTTCATAAAGGGATTTTGAATGTATCAGAACATATGAGGT<br>TTATGTGAATTGCTGTTATGTTTTAAGAAGCATATCATAAG<br>TGATGCGGTTTTTATTAATTAGTTGCTAAAAAATGAAGTATG<br>CAATATTAATTATTATTAAATTTTGATATATTTAAAGAAAGA<br>TTAAGTTTAGGGTGAATGAATGGCTTATCAAAGTGAATATGC<br>ATTAGAAAATGAAGTACTTCAACAACTTGAGGAATTGAACTA<br>TGAAAGAGTAAATATACATAATATTAAATTAGAAATTAATGA |

TABLE OF SEQUENCES

| SEQ ID NO | Description | Sequence 5'→3' |
|---|---|---|
| | | ATATCTCAAAGAACTAGGAGTGTTGAAAAATGAATAAGCAGA CAAATACTCCAGAACTAAGATTTCCAGAGTTTGATGAGGAAT GGAAAAAAAGGAAATTAGGTGAAGTAGTAAATTATAAAAATG GTGGTTCATTTGAAAGTTTAGTGAAAAACCATGGTGTATATA AACTCATAACTCTTAAATCTGTTAATACAGAAGGAAAGTTGT GTAATTCTGGAAAATATATCGATGATAAATGTGTTGAAACAT TGTGTAATGATACTTTAGTAATGATACTGAGCGAGCAAGCAC CAGGACTAGTTGGAATGACTGCAA |
| 12 | Exemplary MREJ xxi sequence | AACGTTTAGGCCCATACACCAAGATAGACATCATAGAAGTTC CAGACGAAAAAGCACCAGAAAATATGAGCGACAAAGAAATCG AGCAAGTAAAAGAAAAAGAAGGCCAACGAATACTAGCCAAAA TCAAACCACAATCCACAGTCATTACATTAGAAATACAAGGAA AGATGCTATCTTCCGAAGGATTGGCCCAAGAATTGAACCAAC GCATGACCCAAGGGCAAAGCGACTTTGTATTCGTCATTGGCG GATCAAACGGCCTGCACAAGGACGTCTTACAACGCAGTAACT ACGCACTATCATTCAGCAAAATGACATTCCCACATCAAATGA TGCGGGTTGTGTTAATTGAAGCAAGTGTATAGAGCGTTTAAG ATTATGCGCGGAGAAGCGTATCACAAATGATGCGGTTTTTTT AACCTCTTTACGTATGAGGTTTATGAGAATTGCCGTTATGTT TTGCGAGAGTTATCAATCTTTTTGATAGTAAGAAAGTACATA GAAACTAAAAGAGTATTTTTATCTACAATAGCATTTATAATT TATTCTATTATTGTATACTTATTTTAATTATTAGTATCATTG CTGAGATGTTACTTGATATTCTATGTCTATTTTTTAGGAAAT TCTATACTATTAAAATTATGGTATTTTATACGCAATAAAGGA CTAATCTATTTTATACAGATTAGTCCTTTATTGTAGTCTTTA AAAACTAGTTACTCATTAATATTTTTAGTACAATTTCAGCA ACCTCACTTACTATTTTGTCATTAGGTTTACCATCTTTTCTA TCTTTATTTGTAAATATCACCAGAATTATAGGTTTATCTTGT CCATCTGGATAAACAAAGCGAACATCGTTTCTTGAACCGTAT GTTAGTGCTTGACCGCTCTTATCCATAACTTTAAAGTTTGAA GGTGCACCATCCTTAATTAATGTATCGCCACTTTTATTTTTG AACATTAGATTAAGTAAGAAATCTTTGTTTGCTTTGCTAAGA TCTCCATCA |
| 13 | Exemplary mecA sequence (GenBank NG_047938) | CCTTCTACACCTCCATATCACAAAAATTATAACATTATTTTG ACATAAATACTACATTTGTAATATACTACAAATGTAGTCTTA TATAAGGAGGATATTGATGAAAAAGATAAAAATTGTTCCACT TATTTTAATAGTTGTAGTTGTCGGGTTTGGTATATATTTTTA TGCTTCCAAAGATAAAGAAATTAATAATACTATTGATGCAAT TGAAGATAAAAATTTCAAACAAGTTTATAAAGATAGCAGTTA TATTTCTAAAAGCGATAATGGTGAAGTAGAAATGACTGAACG TCCGATAAAAATATATAATAGTTTAGGCGTTAAAGATATAAA CATTCAGGATCGTAAAATAAAAAAAGTATCTAAAAATAAAAA ACGAGTAGATGCTCAATATAAAATTAAAACAAACTACGGTAA CATTGATCGCAACGTTCAATTTAATTTTGTTAAAGAAGATGG TATGTGGAAGTTAGATTGGGATCATAGCGTCATTATTCCAGG AATGCAGAAAGACCAAAGCATACATATTGAAAATTTAAAATC AGAACGTGGTAAAATTTTAGACCGAAACAATGTGGAATTGGC CAATACAGGAACAGCATATGAGATAGGCATCGTTCCAAAGAA TGTATCTAAAAAAGATTATAAAGCAATCGCTAAAGAACTAAG TATTTCTGAAGACTATATCAAACAACAAATGGATCAAAATTG GGTACAAGATGATACCTTCGTTCCACTTAAAACCGTTAAAAA AATGGATGAATATTTAAGTGATTTCGCAAAAAAATTTCATCT TACAACTAATGAAACAGAAAGTCGTAACTATCCTCTAGGAAA AGCGACTTCACATCTATTAGGTTATGTTGGTCCCATTAACTC TGAAGAATTAAAACAAAAAGAATATAAAGGCTATAAAGATGA TGCAGTTATTGGTAAAAAGGGACTCGAAAAACTTTACGATAA AAAGCTCCAACATGAAGATGGCTATCGTGTCACAATCGTTGA CGATAATAGCAATACAATCGCACATACATTAATAGAGAAAAA GAAAAAAGATGGCAAAGATATTCAACTAACTATTGATGCTAA AGTTCAAAAGAGTATTTATAACAACATGAAAAATGATTATGG CTCAGGTACTGCTATCCACCCTCAAACAGGTGAATTATTAGC ACTTGTAAGCACACCTTCATATGACGTCTATCCATTTATGTA TGGCATGAGTAACGAAGAATATAATAAATTAACCGAAGATAA AAAAGAACCTCTGCTCAACAAGTTCCAGATTACAACTTCACC AGGTTCAACTCAAAAAATATTAACAGCAATGATTGGGTTAAA TAACAAAACATTAGACGATAAAACAAGTTATAAAATCGATGG TAAAGGTTGGCAAAAAGATAAATCTTGGGGTGGTTACAACGT TACAAGATATGAAGTGGTAAATGGTAATATCGACTTAAAACA AGCAATAGAATCATCAGATAACATTTTCTTTGCTAGAGTAGC ACTCGAATTAGGCAGTAAGAAATTTGAAAAAGGCATGAAAAA ACTAGGTGTTGGTGAAGATATACCAAGTGATTATCCATTTTA |

| TABLE OF SEQUENCES | | |
|---|---|---|
| SEQ ID NO | Description | Sequence¹ 5'→3' |
|  |  | TAATGCTCAAATTTCAAACAAAAATTTAGATAATGAAATATT ATTAGCTGATTCAGGTTACGGACAAGGTGAAATACTGATTAA CCCAGTACAGATCCTTTCAATCTATAGCGCATTAGAAAATAA TGGCAATATTAACGCACCTCACTTATTAAAAGACACGAAAAA CAAAGTTTGGAAGAAAAATATTATTTCCAAAGAAAATATCAA TCTATTAACTGATGGTATGCAACAAGTCGTAAATAAAACACA TAAAGAAGATATTTATAGATCTTATGCAAACTTAATTGGCAA ATCCGGTACTGCAGAACTCAAAATGAAACAAGGAGAAACTGG CAGACAAATTGGGTGGTTTATATCATATGATAAAGATAATCC AAACATGATGATGGCTATTAATGTTAAAGATGTACAAGATAA AGGAATGGCTAGCTACAATGCCAAAATCTCAGGTAAAGTGTA TGATGAGCTATATGAGAACGGTAATAAAAAATACGATATAGA TGAATAACAAAACAGTGAAGCAATCCGTAACGATGGTTGCTT CACTGTTTTATTATGAATTATTAATAAGTGCTGTTACTTCTC CCTTAAATACAATTTCTTCATTT |
| 14 | Exemplary mecC sequence (reverse complement of positions 1741-3738 of GenBank HF569116.1) | ATGAAAAAAATTTATATTAGTGTGCTAGTTCTTTTACTAATT ATGATTATAATAACTTGGTTATTCAAAGATGACGATATTGAG AAAACAATTAGTTCTATTGAAAAAGGAAACTATAACGAAGTA TATAAAAATAGTTCAGAAAAATCTAAACTGGCATATGGAGAA GAAGAAATTGTAGATAGGAATAAAAAAATTTACAAAGATTTA AGTGTCAATAACTTAAAAATTACTAATCATGAAATTAAAAAA ACTGGAAAAGATAAAAAGCAAGTTGATGTTAAATATAACATA TATACAAAATATGGAACTATACGACGTAATACACAATTAAAC TTTATTTATGAAGATAAGCATTGGAAATTAGATTGGAGACCA GACGTAATAGTACCTGGTTTGAAAAATGGACAGAAAATTAAT ATAGAAACATTAAAATCAGAGCGAGGCAAAATAAAAGATAGA AATGGTATAGAATTAGCTAAAACTGGAAATACATATGAAATC GGTATTGTCCCTAACAAAACACCCAAAGAAAAATATGATGAT ATTGCTCGTGACTTACAAATTGATACAAAAGCTATAACCAAT AAAGTTAATCAAAAATGGGTTCAGCCAGATTCATTTGTACCA ATTAAAAGATAAATAAACAAGATGAATATATAGACAAATTA ATTAAATCATACAATTTACAAATAAAACACTATAAAAAGCCGT GTTTATCCATTGAACGAAGCAACAGTACACCTTTTAGGTTAT GTGGGTCCAATTAATTCTGACGAGTTAAAAAGTAAGCAATTT AGAAACTATAGCAAAAATACTGTTATTGGAAAAAAAGGCTTA GAACGCCTCTATGATAAACAATTGCAAAACACTGATGGTTTT AAGGTATCCATTGCAAATACTTATGACAATAAACCTTTAGAC ACATTATTGGAGAAAAAGGCTGAAAACGGAAAAGATCTTCAT TTAACTATAGATGCTAGAGTACAAGAAAGTATTTATAAACAT ATGAAAAATGACGATGGATCTGGTACAGCATTACAACCAAAA ACTGGAGAAATTTTAGCTTTGGTAAGTACCCCATCGTACGAT GTTTATCCATTCATGAATGGATTAAGCAATAATGACTACCGT AAATTAACTAACAATAAAAAAGAGCCTTTGCTCAACAAATTT CAAATCACTACATCACCAGGTTCAACCCAAAAAATATTAACA TCTATTATAGCCTTAAAAGAAAATAAACTAGACAAAAATACT AATTTTGATATTTATGGTAAGGGTTGGCAAAAAGATGCATCA TGGGGGAATTATAATATCACAAGATTTAAAGTAGTAGACGGC AATATCGATTTAAAGCAAGCAATAGAATCATCAGACAACATA TTTTTTGCCCGCATTGCATTAGCATTAGGAGCCAAAAAATTT GAGCAAGGTATGCAAGATTTGGGAATCGGTGAAAATATCCCG AGTGATTATCCCTTTTATAAAGCACAAATCTCAAATAGTAAT TTAAAAAATGAAATATTATTAGCAGATTCAGGATATGGCCAA GGCGAGATACTAGTAAACCCTATACAAATTTTATCAATATAC AGTGCTTTAGAAAATAACGGAAATATACAAAATCCTCATGTT TTACGTAAAACAAAATCTCAAATATGGAAAAAAGATATTATA CCTAAAAAAGACATAGATATATTAACTAATGGTATGGAACGT GTAGTTAATAAAACACATAGGGATGATATATACAAAAATTAT GCCCGAATTATTGGTAAATCTGGCACAGCAGAATTAAAAATG AATCAAGGGGAAACTGGAAGACAAATAGGTTGGTTTGTTTCA TATAATAAAAATAATCCTAATATGTTAATGGCGATTAATGTT AAAGACGTTCAAAATAAAGGGATGGCCAGCTATAATGCTACT ATATCTGGAAAGTTTATGATGATTTGTATGATAATGGAAAA ACTCAATTTGATATAGATCAGTAA |

TABLE OF SEQUENCES

| SEQ ID NO | Description | Sequence¹ 5'→3' |
|---|---|---|
| 15 | Exemplary GAPDH (gapA1) sequence (reverse complement of positions 98744-99754 of GenBank MKZD01000004.1) | ATGGCAGTAAAAGTAGCAATTAATGGTTTTGGTAGAATTGGT<br>CGTTTAGCATTCAGAAGAATTCAAGAAGTAGAAGGTCTTGAA<br>GTTGTAGCAGTAAACGACTTAACAGATGACGACATGTTAGCG<br>CATTTATTAAAATATGACACTATGCAAGGTCGTTTCACAGGT<br>GAAGTAGAGGTAGTTGATGGTGGTTTCCGCGTAAATGGTAAA<br>GAAGTTAAATCATTCAGTGAACCAGATGCAAGCAAATTACCT<br>TGGAAAGACTTAAATATCGATGTAGTATTAGAATGTACTGGT<br>TTCTACACTGATAAAGATAAAGCACAAGCTCATATTGAAGCA<br>GGCGCTAAAAAAGTATTAATCTCAGCACCAGCTACTGGTGAC<br>TTAAAAACAATCGTATTCAACACTAACCACCAAGAGTTAGAC<br>GGTTCTGAAACAGTTGTTTCAGGTGCTTCATGTACTACAAAC<br>TCATTAGCACCAGTTGCTAAAGTTTTAAACGATGACTTTGGT<br>TTAGTTGAAGGTTTAATGACTACAATTCACGCTTACACAGGT<br>GATCAAAATACACAAGACGCACCTCACAGAAAAGGTGACAAA<br>CGTCGTGCTCGTGCAGCGGCAGAAAACATCATCCCTAACTCA<br>ACAGGTGCTGCTAAAGCTATCGGTAAAGTTATTCCTGAAATC<br>GATGGTAAATTAGATGGTGGTGCACAACGTGTTCCTGTAGCT<br>ACAGGTTCATTAACTGAATTAACAGTAGTATTAGAAAAACAA<br>GACGTAACAGTTGAACAAGTTAACGAAGCTATGAAAAATGCT<br>TCAAACGAATCATTCCGGTTACACTGAAGACGAAATCGTTTCT<br>TCAGACGTTGTAGGTATGACTTACGGTTCATTATTCGACGCT<br>ACACAAACTCGTGTAATGTCAGTTGGCGACCGTCAATTAGTT<br>AAAGTTGCAGCTTGGTATGATAACGAAATGTCATATACTGCA<br>CAATTAGTTCGTACATTAGCATACTTAGCTGAACTTTCTAAA<br>TAA |
| 16 | Exemplary orfX sequence (GenBank KX529089.1) | AACGTTTAGGCCCATACACCAAGATAGACATCATAGAAGTTC<br>CAGACGAAAAAGCACCAGAAAATATGAGCGACAAAGAAATCG<br>AGCAAGTAAAAGAAAAAGAAGGCCAACGAATACTAGCCAAAA<br>TCAAACCACAATCCACAGTCATTACATTAGAAATACAAGGAA<br>AGATGCTATCTTCCGAAGGATTGGCCCAAGAATTGAACCAAC<br>GCATGACCCAAGGGCAAAGCGACTTTGTATTCGTCATTGGCG<br>GATCAAACGGCCTGCACAAGGACGTCTTACAACGCAGTAACT<br>ACGCACTATCATTCAGCAAAATGACATTCCCACATCAAATGA<br>TGCGGGTTGTGTTAATTGAA |
| 17 | Exemplary MREJ xv sequence 1 | AACGTTTAGGCCCATACACCAAGATAGACATCATAGAAGTTC<br>CAGACGAAAAAGCACCAGAAAATATGAGCGACAAAGAAATCG<br>AGCAAGTAAAAGAAAAAGAAGGCCAACGAATACTAGCCAAAA<br>TCAAACCACAATCCACAGTCATTACATTAGAAATACAAGGAA<br>AGATGCTATCTTCCGAAGGATTGGCCCAAGAATTGAACCAAC<br>GCATGACCCAAGGGCAAAGCGACTTTGTATTCGTCATTGGCG<br>GATCAAACGGCCTGCACAAGGACGTCTTACAACGCAGTAACT<br>ACGCACTATCATTCAGCAAAATGACATTCCCACATCAAATGA<br>TGCGGGTTGTGTTAATTGAACAAGTGTATAGAGCATTTAAGA<br>TTATGCGAGGAGAAGCGTATCACAAATAAAACTAAAAAATAG<br>ATTGTGTATAATATAAAAGGAAGGGATTTATATTAAAATTTT<br>GAATTCAAAAATTATTGAAAGGGAAGCTACCTTAGAAATTGA<br>ATCTATGGCCACTAATACATTGAAAATAAACCCAGACATTAA<br>TTCTTACTATACAGAAATGTCTTTCGATGGAGAATTGGAAGT<br>GTATGATCCTGAAAATTTGAATAAAAAATTTCGTTGGAAAAA<br>TACAAGTTCAAGTTAAAGGAAAAGAAGTAGCTAAAAGAGGAG<br>GTAAGATTATTCGTCGAAGTAATGGGTTCTGTTGCAAAGTAA<br>AAAAATATAGCTAACCACTAATTTATCATGTCAGTGTTCGCT<br>TAACGATATAAATAGCTCCATTTTCCTTTTATTTTGATGTAC<br>GTCTCATCAATACGCCATTTG |
| 18 | Exemplary MREJ xv sequence 2 | ACCATTTTAGCTGTAGGGAAACTAAAAGAGAAATATTGGAAG<br>CAAGCCATAGCAGAATATGAAAAACGTTTAGGCCCATACACC<br>AAGATAGACATCATAGAAGTTCCAGACGAAAAAGCACCAGAA<br>AATATGAGTGACAAAGAAATTGAGCAAGTAAAAGAAAAAGAA<br>GGCCAACGAATACTAGCCAAAATCAAACCACAATCCACAGTC<br>ATTACATTAGAAATACAAGGAAAGATGCTATCTTCCGAAGGA<br>TTGGCCCAAGAATTGAACCAACGCATGACCCAAGGGCAAAGC<br>GACTTTGTTTCGTCATTGGCGGATCAAACGGCCTGCACAAG<br>GACGTCTTACAACGCAGTAACTACGCACTATCATTCAGCAAA<br>ATGACATTCCCACATCAAATGATGCGGGTTGTGTTAATTGAA<br>CAAGTGTACAGAGCATTTAAGATTATGCGAGGAGAAGCGTAT<br>CACAAATAAAACTAAAAAATAGATTGTGTATAATATAAAAGG<br>AGCGGATTTATATTAAACTTTGAATTCAAAAATTATTGAAA<br>GGGAAGCTACCTTAGAAATTGAATCTATGGCAACTAATACAT<br>TGAAAATAAACCCGGATATTAATTCAAACGATACAAAAATGT |

-continued

| TABLE OF SEQUENCES | | |
|---|---|---|
| SEQ ID NO | Description | Sequence[1] 5'→3' |
| | | CTTTCGATGGAGAATTGGAAGTGTATGATTCTGAAAATTTGA GTAAAAAAATTTCGTTGGAAAAATACAAGTTCAAGTTAAAG GAAAGGAAGTAGCTAAAAGAGGAGGTAAGGTTATTCATCGAA GTAATGTCAAAATGAATGATTTAAAGGCATACCAACGAGAAG GTGGTGTGTATTACTTTGTCGTGTATTTAATCGTTGAGAATA AAAAAGTTGTTGAGAAGCAGGTTTATGG |
| 19 | GAPDH FRET Cassette | [Ca]610]TCT[BHQ-2dT]AGCCGGTTTTCCGGCTGAGACTCCGCGTCCGT-Hdiol |
| 20 | GAPDH Forward amplification oligomer | CGTTTCACAGGTGAAGTAGAGGTA |
| 21 | GAPDH Reverse amplification oligomer | CmeCAGTAmeCATTmeCTAATAmeCTAmeCATmeCGATATT |
| 22 | GAPDH detection oligomer | acggacgcggagAGTTGATGGTGGTTTCCG-Hdiol |
| 23 | GAPDH Forward amplification oligomer | CGCGTAAATGGTAAAGAAGTTAAATCATTCAG |
| 24 | GAPDH Reverse amplification oligomer | GAGCTTGTGCTTTATCTTTATCAGTGT |
| 25 | GAPDH detection oligomer | ACGGACGCGGAGGTGAACCAGATGCAAGCA-Hdiol |
| 26 | GAPDH Reverse amplification oligomer | CTGTTTCAGAACCGTCTAACTCTTGG |
| 27 | mecA/C FRET Cassette | [HEX]TCT[BBQdT]AGCCGGTTTTCCGGCTGAGACGTCCGT GGCCT-Hdiol |
| 28 | mecC detection oligomer | acggacgcggagCATCTATTATAGCCTTAAAAGAAAATAAAC T-Hdiol |
| 29 | mecA detection oligomer | acggacgcggagTCGATTTTATAACTTGTTTTATCGTC-Hdiol |
| 30 | mecA/C Forward amplification oligomer | TTATCTTTTTGCCAACCTTTACCAT |
| 31 | mecA/C Reverse amplification oligomer | TCACCAGGTTCAACTCAAAAAATATTAAC |
| 32 | mecC detection oligomer | AGGCCACGGACGCATCTATTATAGCCTTAAAAGAAAATAAAC T-Hdiol |
| 33 | mecA detection oligomer | AGGCCACGGACGTCGATTTTATAACTTGTTTTATCGTC-Hdiol |
| 34 | mecA/C Forward amplification oligomer | ATmeCTTTTTGmeCmeCAAmeCmeCTTTAmeCmeCAT |

TABLE OF SEQUENCES -continued

| SEQ ID NO | Description | Sequence¹ 5'→3' |
|---|---|---|
| 35 | mecA/C Reverse amplification oligomer | TmeCAmeCmeCAGGTTmeCAAmeCTmeCAAAAAATATTAAC |
| 36 | mecA/C Forward amplification oligomer | GCAAAGAAAATGTTGTCTGATGATTCTATTGCTTG |
| 37 | mecA/C Forward amplification oligomer | GAAAATGTTGTCTGATGATTCTATTGCTTG |
| 38 | mecA Reverse amplification oligomer | CTTGGGGTGGTTACAACGTTACAAGATATG |
| 39 | mecA/C Forward amplification oligomer | CCTGAATCTGCTAATAATATTTCATT |
| 40 | mecA forward amplification oligomer | GTGTCTTTTAATAAGTGAGGTG |
| 41 | mecA detection oligomer | aggccacggacgCGTAACCTGAATCAGCT-Hdiol |
| 42 | mecA Invader | GGGTTAATCAGTATTTCACCTTGTCa |
| 43 | mecA detection oligomer | aggccacggacgCACCTTGTCCGTAACC-Hdiol |
| 44 | mecA 449-465 (+) Invader | GGATCTGTACTGGGTTAATCAGTATTTa |
| 45 | mecA reverse amplification oligomer | GGTGTTGGTGAAGATATACC |
| 46 | mecC Invader | ATCACTCGGGATATTTTCACCGAc |
| 47 | mecC detection oligomer | acggacgcggagTTCCCAAATCTTGCATAC-Hdiol |
| 48 | mecC reverse amplification oligomer | TTAAAGCAAGCAATAGAATCATCAGA |
| 49 | mecC reverse amplification oligomer | ATGGTAAGGGTTGGCAAAAG |
| 50 | MREJ i Reverse amplification oligomer | GAAAGACTGCGGAGGCTAAC |
| 51 | MREJ i Reverse amplification oligomer | GCTAACTATGTCAAAAATCATG |
| 52 | MREJ i Reverse amplification oligomer | GACTGCGGAGGCTAACTATGTC |

-continued

| TABLE OF SEQUENCES | | |
|---|---|---|
| SEQ ID NO | Description | Sequence¹ 5'→3' |
| 53 | MREJ ii, viii, ix, xiv Reverse amplification oligomer | AAGCGGCTGAAATAACCGC |
| 54 | MREJ ii, viii, ix, xiv Reverse amplification oligomer | AAGCGGCTGAAAAACCGC |
| 55 | MREJ ii Reverse amplification oligomer | CmeCmeCTTTATGAAGmeCGGmeCTG |
| 56 | MREJ v Reverse amplification oligomer | TTACGGCTGAAATAACCGC |
| 57 | MREJ xxi Reverse amplification oligomer | CTCTCGCAAAACATAACGGC |
| 58 | orfX/SCCmec junction FRET Cassette | [FAM]TCT[BBQdT]AGCCGGTTTTCCGGCTGAGACCTCGGCGCG-Hdiol |
| 59 | orfX Forward amplification oligomer | CTTCCGAAGGATTGGC |
| 60 | orfX Forward amplification oligomer | CCGAAGGATTGGCCCAAGAATTG |
| 61 | orfX/SCCmec junction detection oligomer | cgcgccgaggCICAAGAATTGAACCAACG-Hdiol |
| 62 | orfX/SCCmec junction detection oligomer | CGCGCCGAGGGAACCAACGCATGACC-Hdiol |
| 63 | MREJ iv Reverse amplification oligomer | GGATATGGAAATCCATCTCTAC |
| 64 | MREJ iv Reverse amplification oligomer | CGCTACTAAAGAGGATATGGAAATCCATCTCTAC |
| 65 | MREJ iv Reverse amplification oligomer | AmeCmeCGmeCTAmeCTAAAGAGGATATGG |
| 66 | MREJ v Reverse amplification oligomer | TTAmeCGGmeCTGAAATAACmeCGC |
| 67 | MREJ vi Reverse amplification oligomer | CTGATTTTCACTCTTCATCTACTTACTC |

-continued

| TABLE OF SEQUENCES | | |
|---|---|---|
| SEQ ID NO | Description | Sequence[1] 5'→3' |
| 68 | MREJ vi Reverse amplification oligomer | GATATAGGTGTCACATCATATTTCGC |
| 69 | MREJ xiii Reverse amplification oligomer | CTCTTTCATAGTTCAATTCCTCAAGTTGTTGA |
| 70 | MREJ xiii Reverse amplification oligomer | GTTGAAGTAmeCTTmeCATTTTmeCTAATGC |
| 71 | MREJ xiii Reverse amplification oligomer | GCCATTCATTCACCCTAAACTTAATCTTTC |
| 72 | MREJ xiii Reverse amplification oligomer | CCATTCATTCACCCTAAAC |
| 73 | MREJ iii Reverse amplification oligomer | ATACACAACCTAATTTTTAG |
| 74 | MREJ iii Reverse amplification oligomer | GTATGATATTGCAAGGTATAATCC |
| 75 | MREJ iii Reverse amplification oligomer | CACTCTATAAACATCGTATGATATTGCAAG |
| 76 | MREJ vii Reverse amplification oligomer | TAATGGAAATTCTTAATCTTTACTTGTACC |
| 77 | MREJ vii Reverse amplification oligomer | GGAAATTmeCTTAATmeCTTTAmeCTTGTAmeCC |
| 78 | MREJ vii Reverse amplification oligomer | CAAAAAGAAGTCGATTTACACACCATG |
| 79 | MREJ vii Reverse amplification oligomer | CTTTACATCGCTTACTGCAAACATCTAATAC |
| 80 | MREJ xii Reverse amplification oligomer | AATGAGmeCTTTTTmeCmeCAmeCTmeCmeCmeCATTTC |
| 81 | MREJ xii Reverse amplification oligomer | TmeCmeCAmeCTmeCmeCmeCATTTmeCTTmeCC |

TABLE OF SEQUENCES

| SEQ ID NO | Description | Sequence¹ 5'→3' |
|---|---|---|
| 82 | MREJ xii Reverse amplification oligomer | ACTTAATGAGCTTTTTCCACTC |
| 83 | MREJ xv Reverse amplification oligomer | CAATTTmeCTAAGGTAGmeCTTmeCmeCmeCTTTC |
| 84 | MREJ xv Reverse amplification oligomer | CAATTTCTAAGGTAGCTTCCCTTTC |
| 85 | orfX/SCCmec junctiondetection oligomer core sequence | CCGAGGGAACCA |
| 86 | orfX/SCCmec junctiondetection oligomer core sequence | ccgaggCICAAG |
| 87 | mecA detection oligomer core sequence | CGGACGTCGATT |
| 88 | mecA detection oligomer core sequence | caacctGTTTTA |
| 89 | mecA detection oligomer core sequence | gcggagTCGATT |
| 90 | mecA detection oligomer core sequence | cggacgCGTAAC |
| 91 | mecA detection oligomer core sequence | cggacgCACCTT |
| 92 | mecC detection oligomer core sequence | gcggagCATCTA |
| 93 | mecC detection oligomer core sequence | gcggagTTCCCA |
| 94 | mecC detection oligomer core sequence | CGGACGCATCTA |
| 95 | GAPDH detection oligomer core sequence | GCGGAGGTGAAC |
| 96 | GAPDH detection oligomer core sequence | gcggagAGTTGA |

-continued

| TABLE OF SEQUENCES | | |
|---|---|---|
| SEQ ID NO | Description | Sequence¹ 5'→3' |
| 97 | orfX/SCCmec junctiondetection oligomer target-hybridizing sequence | GAACCAACGCATGACC |
| 98 | orfX/SCCmec junctiondetection oligomer target-hybridizing sequence | CICAAGAATTGAACCAACG |
| 99 | mecA detection oligomer target-hybridizing sequence | TCGATTTTATAACTTGTTTTATCGTC |
| 100 | mecA detection oligomer target-hybridizing sequence | TCGATTTTATAACTTGTTTTATCGTC |
| 101 | mecA detection oligomer target-hybridizing sequence | GTTTTAAGTCGATATTACCATTTACCAC |
| 102 | mecA detection oligomer target-hybridizing sequence | CGTAACCTGAATCAGCT |
| 103 | mecA detection oligomer target-hybridizing sequence | CACCTTGTCCGTAACC |
| 104 | mecC detection oligomer target-hybridizing sequence | CATCTATTATAGCCTTAAAAGAAAATAAACT |
| 105 | mecC detection oligomer target-hybridizing sequence | CATCTATTATAGCCTTAAAAGAAAATAAACT |
| 106 | mecC detection oligomer target-hybridizing sequence | TTCCCAAATCTTGCATAC |
| 107 | GAPDH detection oligomer target-hybridizing sequence | GTGAACCAGATGCAAGCA |

-continued

| TABLE OF SEQUENCES | | |
|---|---|---|
| SEQ ID NO | Description | Sequence<sup>1</sup> 5'→3' |
| 108 | GAPDH detection oligomer target-hybridizing sequence | AGTTGATGGTGGTTTCCG |
| 109 | mecC forward amplification oligomer | ATCTTTTTGCCAACCCTTACCAT |
| 110 | mecC reverse amplification oligomer | TCACCAGGTTCAACCCAAAAAATATTAAC |
| 111 | orfX/SCCmec junction detection oligomer | ACGGACGCGGAGGAACCAACGCATGACC |
| 112 | mecA detection oligomer | CGCGCCGAGGTCGATTTTATAACTTGTTTTATCGTC |
| 113 | mecC detection oligomer | CGCGCCGAGGCATCTATTATAGCCTTAAAAGAAAATAAACT |
| 114 | GAPDH detection oligomer | AGGCCACGGACGGTGAACCAGATGCAAGCA |
| 115 | orfX/SCCmec junction detection oligomer | AGGCCACGGACGGAACCAACGCATGACC |
| 116 | mecA detection oligomer | ACGGACGCGGAGTCGATTTTATAACTTGTTTTATCGTC |
| 117 | mecC detection oligomer | ACGGACGCGGAGCATCTATTATAGCCTTAAAAGAAAATAAACT |
| 118 | GAPDH detection oligomer | CGCGCCGAGGGTGAACCAGATGCAAGCA |
| 119 | orfX/SCCmec junction detection oligomer core sequence | GCGGAGGAACCA |
| 120 | mecA detection oligomer core sequence | CCGAGGTCGATT |
| 121 | mecC detection oligomer core sequence | CCGAGGCATCTA |
| 122 | GAPDH detection oligomer core sequence | CGGACGGTGAAC |
| 123 | orfX/SCCmec junction detection oligomer core sequence | CGGACGGAACCA |
| 124 | mecA detection oligomer core sequence | GCGGAGTCGATT |

TABLE OF SEQUENCES

| SEQ ID NO | Description | Sequence¹ 5'→3' |
|---|---|---|
| 125 | mecC detection oligomer core sequence | GCGGAGCATCTA |
| 126 | GAPDH detection oligomer core sequence | CCGAGGGTGAAC | mec = 5'-methyl-2'deoxycytosine,
Hdiol = Hexanediol,
HEX = Hexochloro-Fluorescein,
FAM = Fluorescein,
Cy5.5 = Cyanine 5.5,
Cal610 = Cal Fluor Red 610,
BBQdT = Blackberry Quencher 650 dT,
BHQ-2 dT = Black Hole Quencher 2 dT

---

What is claimed is:

1. A composition comprising:
at least one orfX amplification oligomer, at least a first SCCmec right extremity junction (MREJ) amplification oligomer and a second MREJ amplification oligomer, at least one detection oligomer comprising a non-nucleotide detectable label, a plurality of mec amplification oligomers, and at least first and second GAPDH amplification oligomers, wherein:
the orfX amplification oligomer comprises the sequence of SEQ ID NO: 59 or 60;
the first MREJ amplification oligomer comprises the sequence of SEQ ID NO: 83 including cytosine methylation or the sequence of SEQ ID NO: 84;
the orfX amplification oligomer and the first MREJ amplification oligomer are configured to produce a first orfX/SCCmec junction amplicon of a length ranging from about 200 nucleotides to about 2000 nucleotides from a MRSA of MREJ type xv;
the orfX amplification oligomer and the second MREJ amplification oligomer are configured to produce a second orfX/SCCmec junction amplicon of a length ranging from about 200 nucleotides to about 2000 nucleotides from a MRSA of one or more MREJ types different from MREJ type xv;
wherein the at least one detection oligomer comprises an orfX/SCCmec junction primary detection oligomer configured to hybridize specifically to one or more orf/SCCmec junction amplicons, including the first orfX/SCCmec junction amplicon;
the plurality of mec amplification oligomers comprises first and second mecA/mecC amplification oligomers;
the first mecA/mecC amplification oligomer is configured to specifically hybridize to a site in SEQ ID NO: 13 comprising position 1394 of SEQ ID NO: 13 and a site in SEQ ID NO: 14 comprising position 1285 of SEQ ID NO: 14, or to a site in SEQ ID NO: 13 comprising position 1484 of SEQ ID NO: 13 and a site in SEQ ID NO: 14 comprising position 1376 of SEQ ID NO: 14;
the second mecA/mecC amplification oligomer is configured to specifically hybridize to a site in SEQ ID NO: 13 comprising position 1312 of SEQ ID NO: 13 and a site in SEQ ID NO: 14 comprising position 1203 of SEQ ID NO: 14;
the first and second mecA/mecC amplification oligomers are configured to produce a mec amplicon;
the first GAPDH amplification oligomer is configured to specifically hybridize to a site in SEQ ID NO: 15 comprising position 169 or 212 of SEQ ID NO: 15;
the second GAPDH amplification oligomer is configured to specifically hybridize to a site in SEQ ID NO: 15 comprising position 279, 312, or 421 of SEQ ID NO: 15; and
the first and second GAPDH amplification oligomers are configured to produce a GAPDH amplicon.

2. A method of detecting MRSA nucleic acid comprising:
preparing a composition according to claim 1, wherein the composition further comprises a sample comprising or suspected of comprising MRSA nucleic acid;
subjecting the composition to amplification conditions; and
detecting the presence or absence of the first orfX/SCCmec junction amplicon, the second orfX/SCCmec junction amplicon, the mec amplicon, and the GAPDH amplicon.

3. The composition of claim 1, wherein the composition further comprises at least a third MREJ amplification oligomer configured to hybridize specifically to at least one of an SCCmec sequence of at least one of MREJ types i, ii, iii, iv, v, vi, vii, viii, ix, xii, xiii, xiv, or xxi which is different from the MREJ type to which the second MREJ amplification oligomer is configured to specifically hybridize to, wherein the third MREJ amplification oligomer is configured to produce an orfX/SCCmec junction amplicon of a length ranging from about 50 nucleotides to about 2000 nucleotides; or the composition further comprises a plurality of MREJ amplification oligomers configured to hybridize specifically to at least one of an SCCmec sequence of at least one of MREJ types i, ii, iii, iv, v, vi, vii, viii, ix, xii, xiii, xiv, xv, or xxi, wherein the at least one orfX amplification oligomer and the MREJ amplification oligomers of the composition collectively are configured to produce orfX/SCCmec junction amplicons from at least 7, 8, 9, 10, 11, 12, 13, or 14 of MREJ types i, ii, iii, iv, v, vi, vii, viii, ix, xii, xiii, xiv, xv, or xxi, wherein the orfX/SCCmec junction amplicons are of lengths ranging from about 200 nucleotides to about 2000 nucleotides.

4. The composition of claim 1, wherein the composition comprises:
(i) at least one MREJ amplification oligomer configured to specifically hybridize to an MREJ type i nucleic acid at a site in SEQ ID NO: 1 comprising at least one of positions 277, 287, or 293 of SEQ ID NO: 1;
(ii) at least one MREJ amplification oligomer configured to specifically hybridize to an MREJ type ii nucleic acid at a site in SEQ ID NO: 2 comprising at least one of positions 613, 622, 721, 731, or 737 of SEQ ID NO: 2;
(iii) at least one MREJ amplification oligomer configured to specifically hybridize to an MREJ type ix nucleic acid at a site in SEQ ID NO: 8 comprising position 473 or 654 of SEQ ID NO: 8;
(iv) at least one MREJ amplification oligomer configured to specifically hybridize to an MREJ type xiv nucleic acid at a site in SEQ ID NO: 11 comprising position 482, 584, or 765 of SEQ ID NO: 11; and/or (v) at least one MREJ amplification oligomer configured to specifically hybridize to at least one of MREJ types i, ii, viii, ix, and xiv, and comprising the sequence of one of SEQ ID NOs: 50-55 or 69-72, with up to two mismatches.

5. The composition of claim 1, wherein the composition comprises:
(i) at least one MREJ amplification oligomer comprising the sequence of one of SEQ ID NOs: 52, 53, or 55;
(ii) at least one MREJ amplification oligomer comprising the sequence of SEQ ID NO: 50;
(iii) at least one MREJ amplification oligomer comprising the sequence of SEQ ID NO: 51;
(iv) at least one MREJ amplification oligomer comprising the sequence of SEQ ID NO: 53 or 54;
(v) at least one MREJ amplification oligomer comprising the sequence of SEQ ID NO: 69-72;
(vi) at least one MREJ amplification oligomer comprising the sequence of one of SEQ ID NOs: 73-75;
(vii) at least one MREJ amplification oligomer comprising the sequence of one of SEQ ID NOs: 63-65;
(viii) at least one MREJ amplification oligomer comprising the sequence of SEQ ID NO: 66 including cytosine methylation or the sequence of SEQ ID NO: 56;
(ix) at least one MREJ amplification oligomer comprising the sequence of one of SEQ ID NOs: 67-68;
(x) at least one MREJ amplification oligomer comprising the sequence of one of SEQ ID NOs: 76-79;
(xi) at least one MREJ amplification oligomer comprising the sequence of one of SEQ ID NOs: 80-82;
(xii) at least one MREJ amplification oligomer comprising the sequence of one of SEQ ID NOs: 69-72; and/or
(xiii) at least one MREJ amplification oligomer comprising the sequence of SEQ ID NO: 57.

6. The composition of claim 1, wherein the composition comprises:
(i) an MREJ amplification oligomer configured to specifically hybridize to an MREJ type iv nucleic acid at a site in SEQ ID NO: 4 comprising at least one of positions 545, 551, or 559 of SEQ ID NO: 4;
(ii) at least one MREJ amplification oligomer configured to specifically hybridize to an MREJ type iii nucleic acid at a site in SEQ ID NO: 3 comprising at least one of positions 668, 738, or 750 of SEQ ID NO: 3;
(iii) an MREJ amplification oligomer configured to specifically hybridize to an MREJ type v nucleic acid at a site in SEQ ID NO: 5 comprising position 458 of SEQ ID NO: 5
(iv) an MREJ amplification oligomer configured to specifically hybridize to an MREJ type vi nucleic acid at a site in SEQ ID NO: 6 comprising position 498 or 611 of SEQ ID NO: 6;
(v) an MREJ amplification oligomer configured to specifically hybridize to an MREJ type vii nucleic acid at a site in SEQ ID NO: 7 comprising at least one of positions 563, 565, 601, or 629 of SEQ ID NO: 7;
(vi) an MREJ amplification oligomer configured to specifically hybridize to an MREJ type xii nucleic acid at a site in SEQ ID NO: 9 comprising at least one of positions 617, 624, or 630 of SEQ ID NO: 9;
(vii) an MREJ amplification oligomer is configured to specifically hybridize to an MREJ type xiii nucleic acid at a site in SEQ ID NO: 10 comprising at least one of positions 561, 568, 605, or 628 of SEQ ID NO: 10; and/or
(viii) at least one MREJ amplification oligomer configured to specifically hybridize to an MREJ type xxi nucleic acid at a site in SEQ ID NO: 12 comprising position 461 of SEQ ID NO: 12.

7. The composition of claim 1, wherein the orfX/SCCmec junction primary detection oligomer is non-extendable.

8. The composition of claim 7, wherein the orfX/SCCmec junction primary detection oligomer is configured to hybridize specifically to a site in SEQ ID NO: 16 comprising at least one of positions 201 and 211 of SEQ ID NO: 16; and/or the orfX/SCCmec junction primary detection oligomer is configured to hybridize specifically to a site in SEQ ID NO: 16 overlapping the site in SEQ ID NO: 16 to which the orfX amplification oligomer is configured to specifically hybridize.

9. The composition of claim 7, wherein the orfX/SCCmec junction primary detection oligomer comprises the sequence of at least one of SEQ ID NO: 85, 86, 97, 98, 61, 62, 111, or 115.

10. The composition of claim 1, wherein the first MREJ amplification oligomer comprises the sequence of SEQ ID NO: 83 including cytosine methylation.

11. The composition of claim 1, wherein the first and second mecA/mecC amplification oligomers comprise:
(i) a mec amplification oligomer that competes for hybridization under stringent conditions for binding to a mecA or mecC nucleic acid with an oligomer having a sequence consisting of SEQ ID NO: 30, 34, 36, 37, or 39;
(ii) a mec amplification oligomer that comprises the sequence of SEQ ID NO: 30, 34, 36, 37, or 39;
(iii) a mec amplification oligomer that competes for hybridization under stringent conditions for binding to a mecA or mecC nucleic acid with an oligomer having a sequence consisting of SEQ ID NO: 31 or 35; or
(iv) a mec amplification oligomer that comprises the sequence of SEQ ID NO: 31 or 35.

12. The composition of claim 1, wherein the composition comprises at least one pair of *S. aureus*-specific or *S. aureus*-indicative amplification oligomers configured to produce an *S. aureus*-specific or *S. aureus*-indicative amplicon, wherein:
(i) the pair of *S. aureus*-specific or *S. aureus*-indicative amplification oligomers is configured to hybridize specifically to one of nuc, rRNA, femB, Sa442, or Staphyloxanthin, in an *S. aureus* chromosome;
(ii) at least one *S. aureus*-specific or *S. aureus*-indicative amplification oligomer competes for binding to *S. aureus* GAPDH under stringent conditions with an oligomer having a sequence consisting of SEQ ID NO: 20 or 23 or at least one *S. aureus*-specific or *S. aureus*-indicative amplification oligomer comprises the sequence of SEQ ID NO: 20 or 23; or
(iii) at least one *S. aureus*-specific or *S. aureus*-indicative amplification oligomer competes for binding to *S. aureus* GAPDH under stringent conditions with an oligomer having a sequence consisting of SEQ ID NO: 21, 24, or 26 or comprises the sequence of SEQ ID NO: 21, 24, or 26;
optionally wherein the composition comprises at least one *S. aureus*-specific or *S. aureus*-indicative primary detection oligomer, further optionally wherein the *S. aureus*-specific or *S. aureus*-indicative primary detection oligomer competes for binding to *S. aureus* GAPDH under stringent conditions with an oligomer having a sequence consisting of SEQ ID NO: 22, 25, 114, or 118 or the *S. aureus*-specific or *S. aureus*- indicative primary detection oligomer comprises the sequence of at least one of SEQ ID NO: 95, 96, 107, 108, 22, 25, 114, or 118.

13. The composition of claim 1, wherein the at least one detection oligomer comprises a secondary detection oligomer that comprises a label and is configured to interact with a fragment of a primary detection oligomer, wherein the secondary detection oligomer comprises the sequence of SEQ ID NO: 58, the sequence of SEQ ID NO: 19, or the sequence of SEQ ID NO: 27, wherein the secondary detection oligomer is a FRET cassette.

14. The composition or kit of claim 1, wherein the composition comprises:
   (i) a nuclease with structure-specific activity toward a three-strand structure formed by 3'-end invasion, a cleavase or 5'-nuclease, or a FEN1 nuclease; and/or
   (ii) a polymerase which is optionally a DNA polymerase, a thermostable DNA polymerase, or a hot-start DNA polymerase.

15. The composition of claim 1, wherein the composition comprises:
   a mec primary detection oligomer that
   (i) competes for hybridization under stringent conditions for binding to a mecA nucleic acid with an oligomer having a sequence consisting of SEQ ID NO: 29, 33, 112, or 116;
   (ii) comprises the sequence of SEQ ID NO: 29, 33, 112, or 116;
   (iii) competes for hybridization under stringent conditions for binding to a mecC nucleic acid with an oligomer having a sequence consisting of SEQ ID NO: 28, 32, 113, or 117; or
   (iv) comprises the sequence of SEQ ID NO: 28, 32, 113, or 117.

16. The method of claim 2, wherein the presence of the first orf/SCCmec junction amplicon, the second orfX/SCCmec junction amplicon, the mec amplicon, and the GAPDH amplicon is dectecte and is indicative of MRSA nucleic acid in the sample.

* * * * *